US012558577B2

(12) United States Patent
Wang et al.

(10) Patent No.: US 12,558,577 B2
(45) Date of Patent: Feb. 24, 2026

(54) ANTI-HUMAN TROP-2 ANTIBODY AND APPLICATION THEREOF

(71) Applicant: MABWELL (SHANGHAI) BIOSCIENCE CO., LTD., Shanghai (CN)

(72) Inventors: Shuang Wang, Shanghai (CN); Rongjuan Wang, Shanghai (CN); Shasha Jiao, Shanghai (CN); Chang Zhang, Shanghai (CN); Jiao Zhang, Shanghai (CN); Dadi Zeng, Shanghai (CN); Jinchao Zhang, Shanghai (CN)

(73) Assignee: MABWELL (SHANGHAI) BIOSCIENCE CO., LTD., Shanghai (CN)

( * ) Notice: Subject to any disclaimer, the term of this patent is extended or adjusted under 35 U.S.C. 154(b) by 990 days.

(21) Appl. No.: 17/768,189

(22) PCT Filed: Oct. 12, 2020

(86) PCT No.: PCT/CN2020/120277
§ 371 (c)(1),
(2) Date: Apr. 11, 2022

(87) PCT Pub. No.: WO2021/068949
PCT Pub. Date: Apr. 15, 2021

(65) Prior Publication Data
US 2024/0092930 A1     Mar. 21, 2024

(30) Foreign Application Priority Data
Oct. 11, 2019   (CN) ......................... 201910962965.1

(51) Int. Cl.
| | |
|---|---|
| C07K 16/28 | (2006.01) |
| A61K 47/68 | (2017.01) |
| A61P 35/00 | (2006.01) |
| C07K 16/30 | (2006.01) |
| A61K 39/00 | (2006.01) |

(52) U.S. Cl.
CPC .... *A61K 47/6851* (2017.08); *A61K 47/68037* (2023.08); *A61P 35/00* (2018.01); *C07K 16/28* (2013.01); *C07K 16/2803* (2013.01); *C07K 16/30* (2013.01); *A61K 2039/505* (2013.01); *C07K 2319/00* (2013.01)

(58) Field of Classification Search
CPC .............. A61P 35/00; A61K 47/68037; A61K 47/6851; A61K 2039/505; A61K 2039/507; A61K 2039/545; A61K 47/6877; A61K 47/6803; C07K 16/2803; C07K 16/30; C07K 2319/00; C07K 2317/24; C07K 2317/77; C07K 2317/90; C07K 2317/92; C07K 2317/54; C07K 2317/55; C07K 2317/56; C12N 15/70
See application file for complete search history.

(56) References Cited

U.S. PATENT DOCUMENTS

| | | | |
|---|---|---|---|
| 2012/0052076 A1 | 3/2012 | Alberti | |
| 2013/0089872 A1 | 4/2013 | Nakamura et al. | |
| 2018/0237520 A1* | 8/2018 | Schendel | ............. C07K 16/085 |

FOREIGN PATENT DOCUMENTS

| | | | | |
|---|---|---|---|---|
| CN | 104114580 A | * 10/2014 | .......... | A61K 39/395 |
| CN | 105849126 A | 8/2016 | | |
| CN | 107446050 A | 12/2017 | | |
| TW | 201333036 A | * 8/2013 | ............. | A61K 38/08 |
| WO | WO 2011/145744 A1 | 11/2011 | | |
| WO | WO 2017/084763 A1 | 5/2017 | | |
| WO | WO 2017/139623 A1 | 8/2017 | | |
| WO | WO 2018/102212 A1 | 6/2018 | | |

OTHER PUBLICATIONS

Rudikoff et al. Proceedings of the National Academy of Sciences USA, vol. 79, p. 1979-1983, 1982 (Year: 1982).*
Kappell et al., Current Opinions in Biotechnology, vol. 3, p. 548-553, 1992 (Year: 1992).*
Paul, Fundamental Immunology, 3rd Edition, 1993, pp. 292-295 (Year: 1993).*
Houdebine et al., Journal of Biotechnology, vol. 34, p. 269-287, 1994 (Year: 1994).*
Bendig M. M. Methods: A Companion to Methods in Enzymology, 1995; 8:83-93 (Year: 1995).*
Wall et al., Theriogenology, vol. 45, p. 57-68, 1996 (Year: 1996).*
Evans et al. Q. J. Med 1999: 92: 299-307 (Year: 1999).*
Cuzick et al. The Lancet, vol. 361, p. 296-300, 2003 (Year: 2003).*
Komenaka et al., Clinics in Dermatology, 2004, vol. 22, p. 251-265 (Year: 2004).*
Schiffman et al., The New England Journal of Medicine, Vo. 353, No. 20, p. 2101-2104, 2005 (Year: 2005).*
Houdebine. Comparative Immunology, Microbiology, and Infectious Diseases, vol. 32, p. 107-121, 2009 (Year: 2009).*
Hernandez-Ledesma et al. Peptides, vol. 30, p. 426-430, 2009 (Year: 2009).*
Stepan et al. Journal of Histochemistry & Cytochemistry. 2011;59(7):701-710 (Year: 2011).*
Smith et al. Scientific Reports vol. 5, Article No. 17943, p. 1-12, Dec. 11, 2015 (Year: 2015).*

\*    cited    by    examiner

*Primary Examiner* — Sean E Aeder
*Assistant Examiner* — Yie Chia Lee
(74) *Attorney, Agent, or Firm* — Lewis Roca Rothgerber Christie LLP

(57) ABSTRACT

The present invention provides an antibody binding a human tumor-associated calcium signal sensor 2 (Trop-2) protein or fragments thereof, and use of the antibody or fragments thereof in preventing or treating diseases. The antibody or fragments thereof of the present invention can effectively bind to the human Trop-2 protein, and have internalization activity, and the internalization activity is enhanced after ADC drug labeling, and the in vivo efficacy and safety of a mouse model are not lower than those of a control antibody.

23 Claims, 13 Drawing Sheets

Specification includes a Sequence Listing.

4A

4B

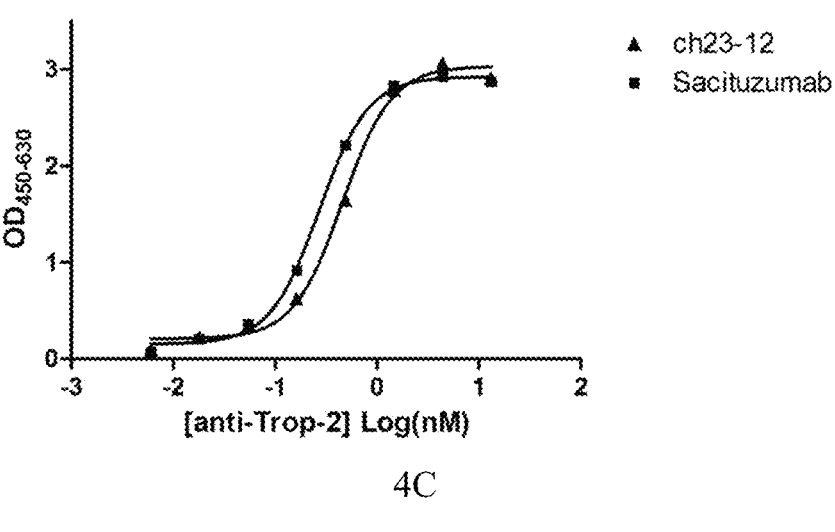
4C
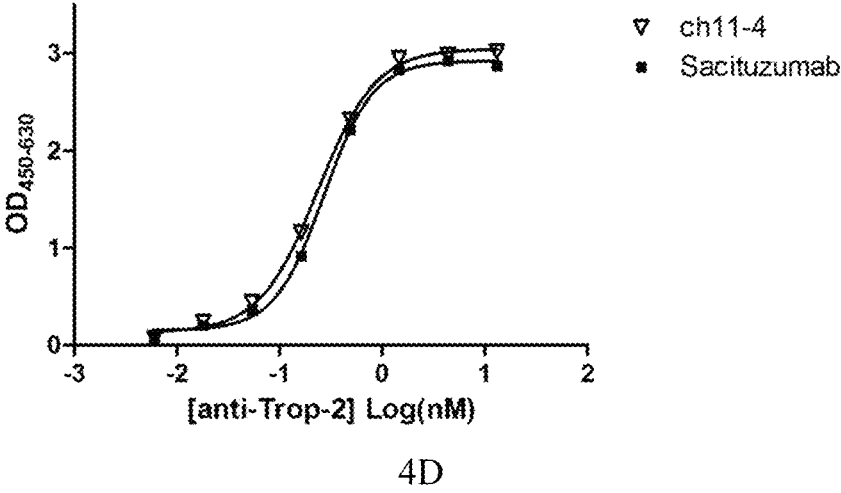
4D
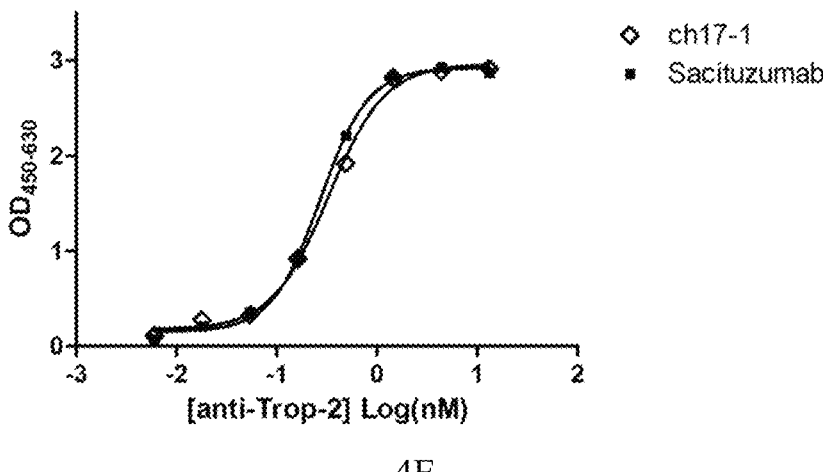
4E

5A

5B

5C

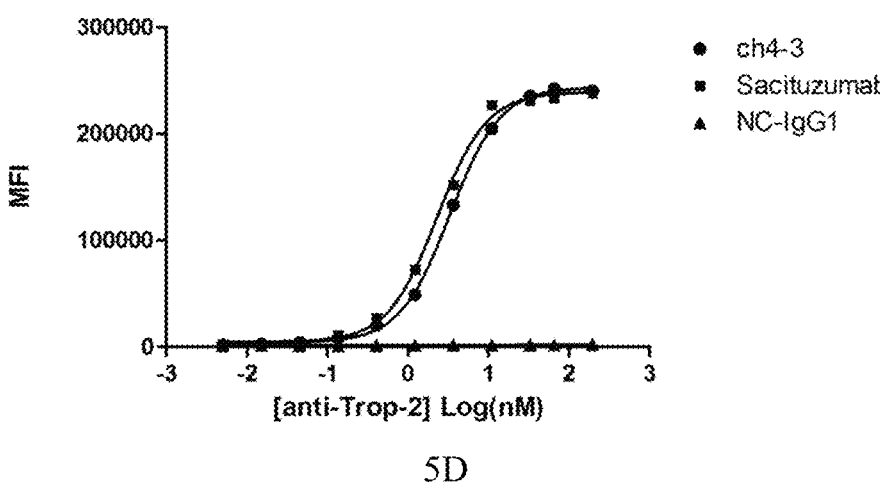
5D
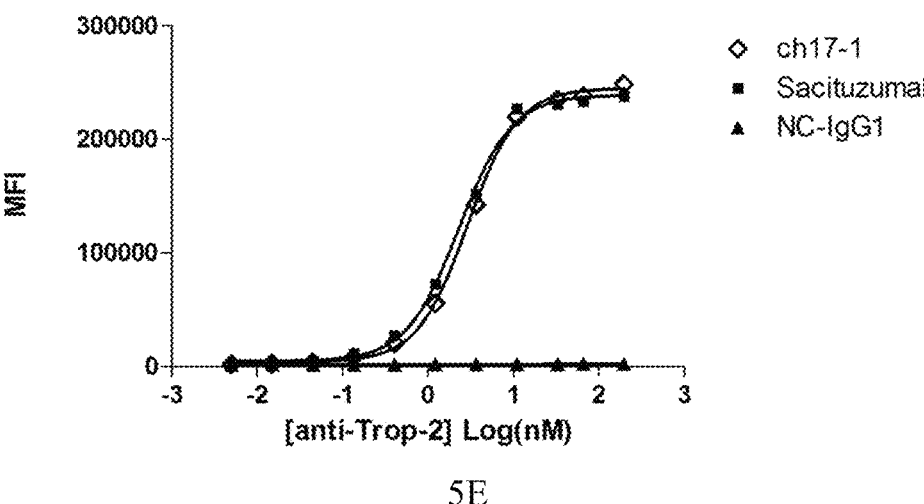
5E
FIG. 6
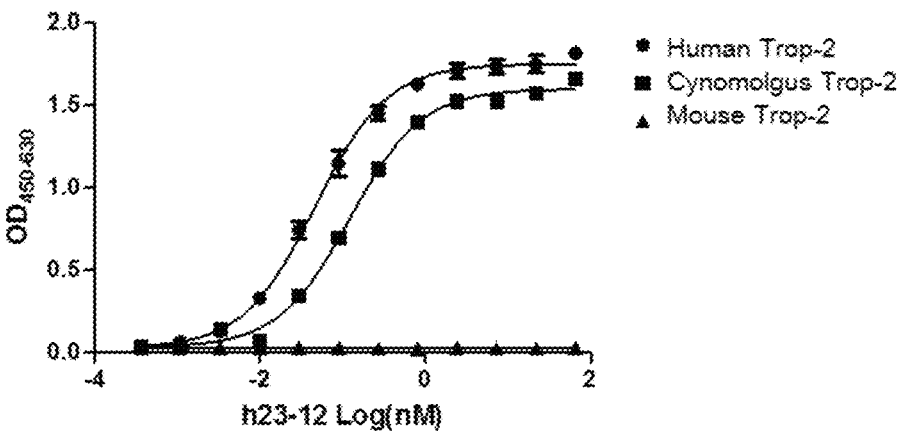
6A

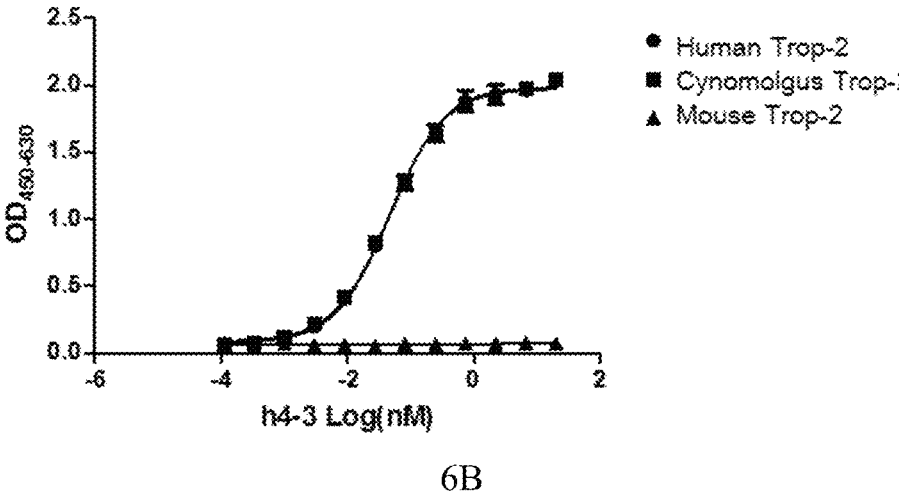
6B
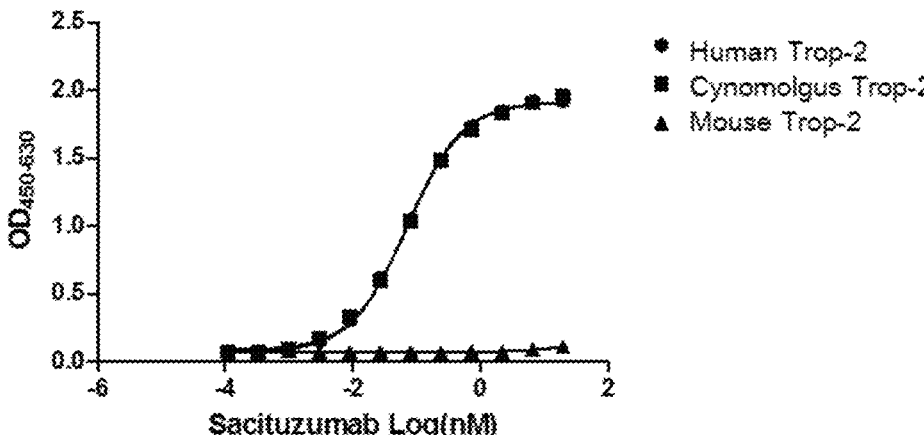
6C
FIG. 7
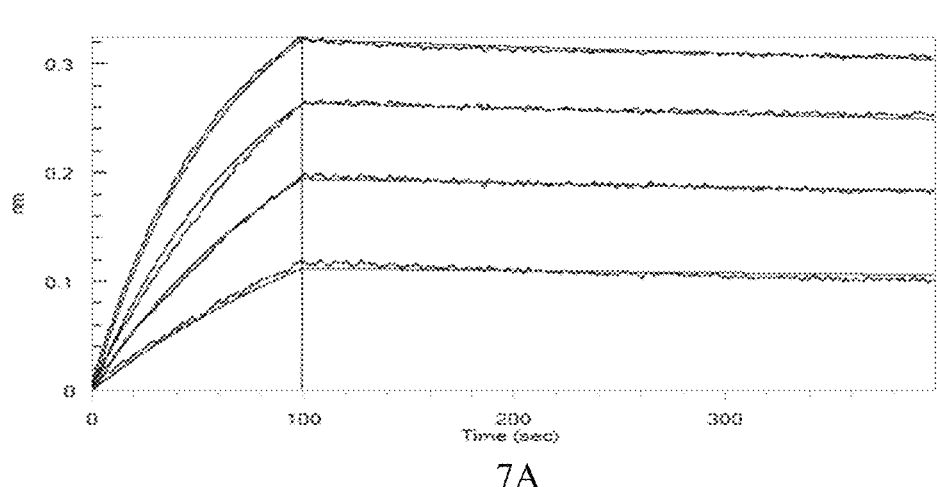
7A

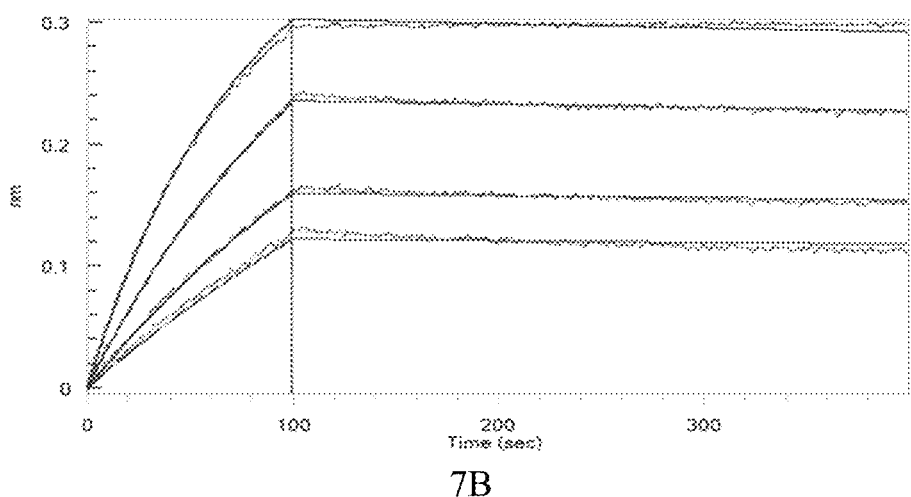
7B
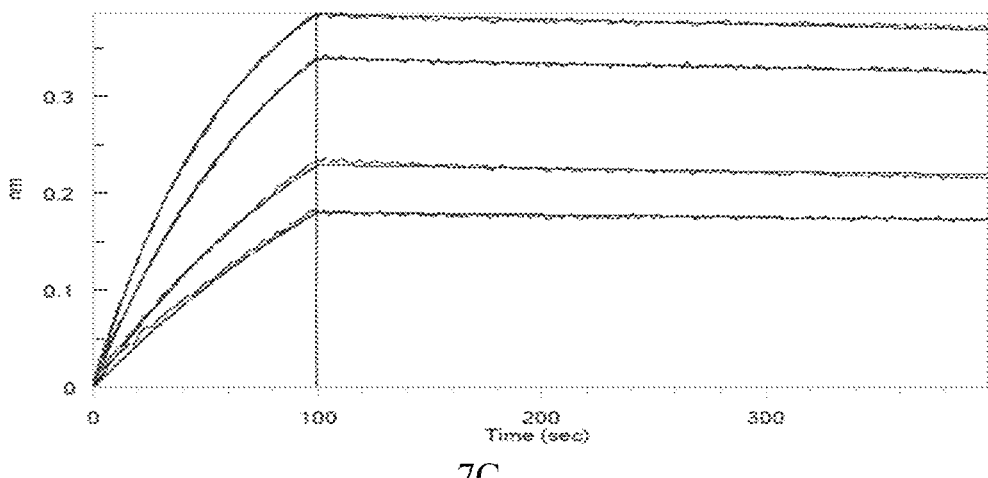
7C
FIG. 8
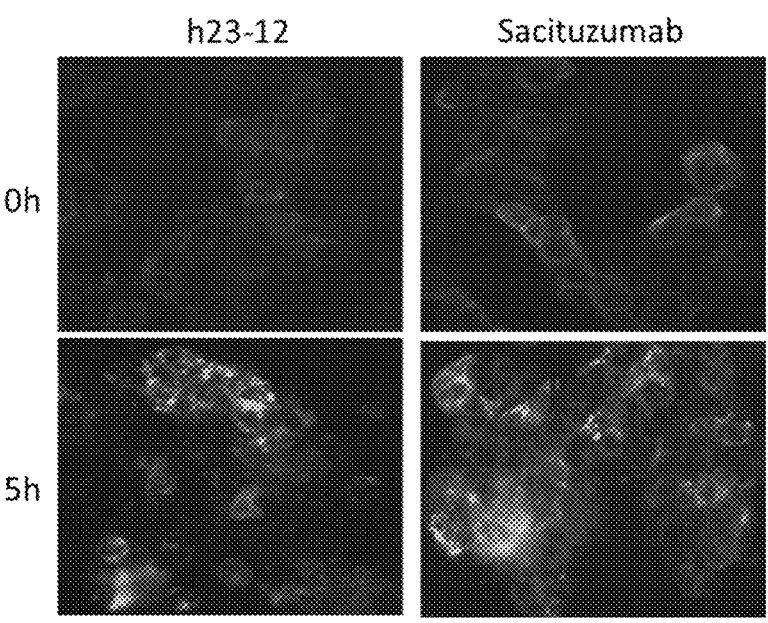

9A

9B

11A

11B

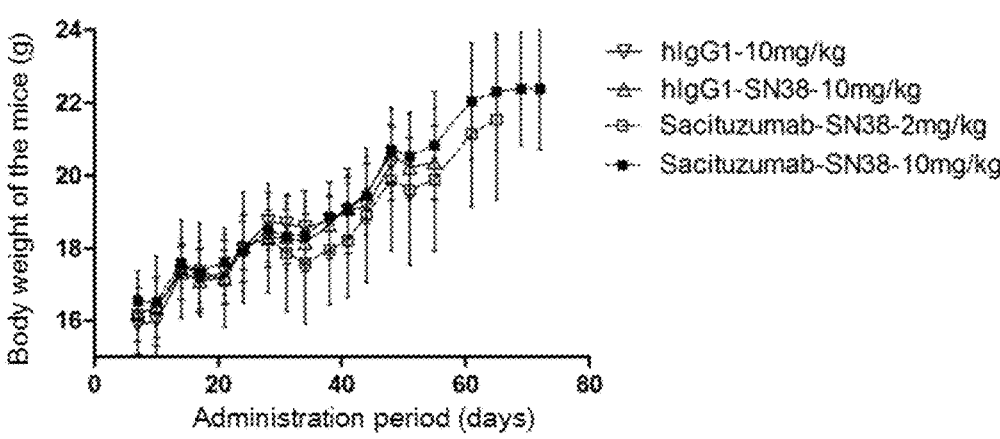
11C
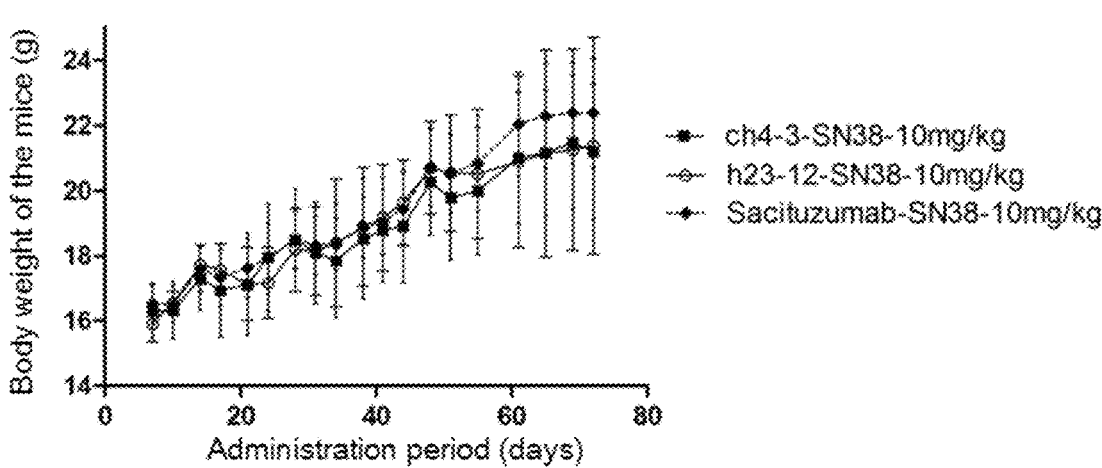
11D
FIG. 12
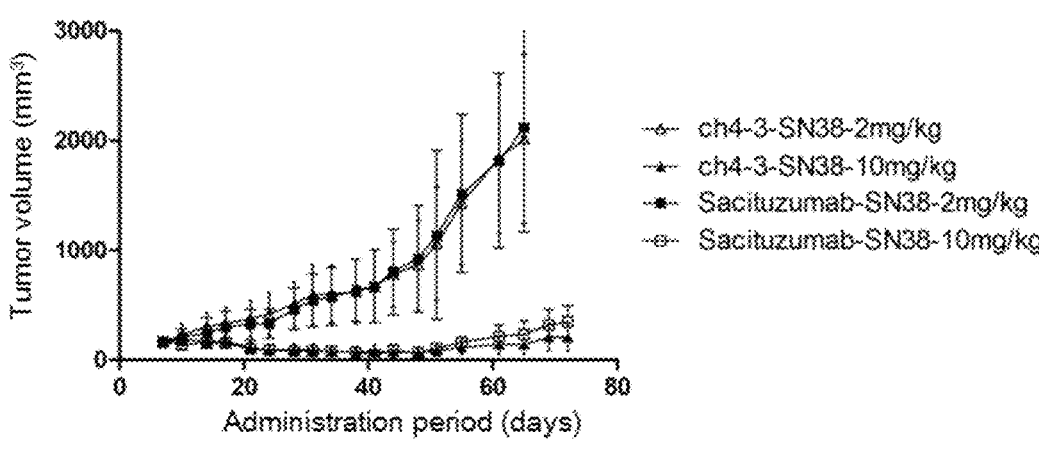
12A

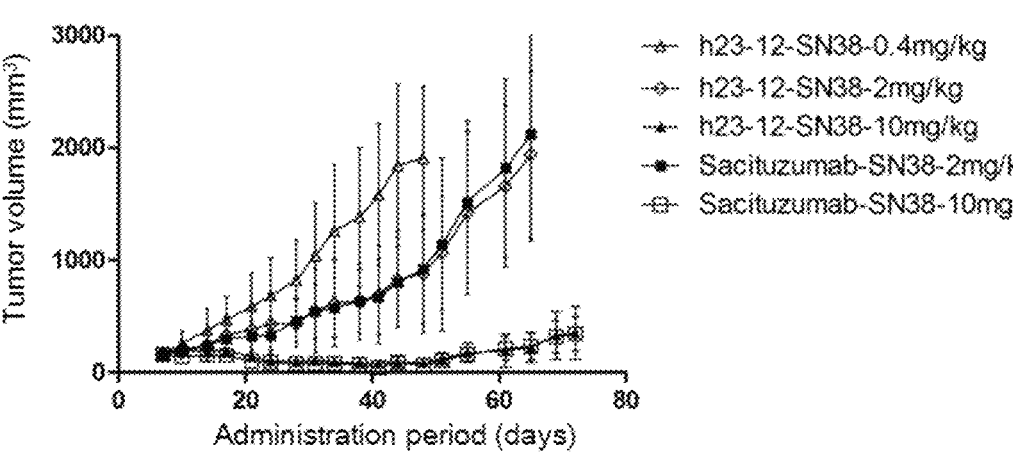
12B
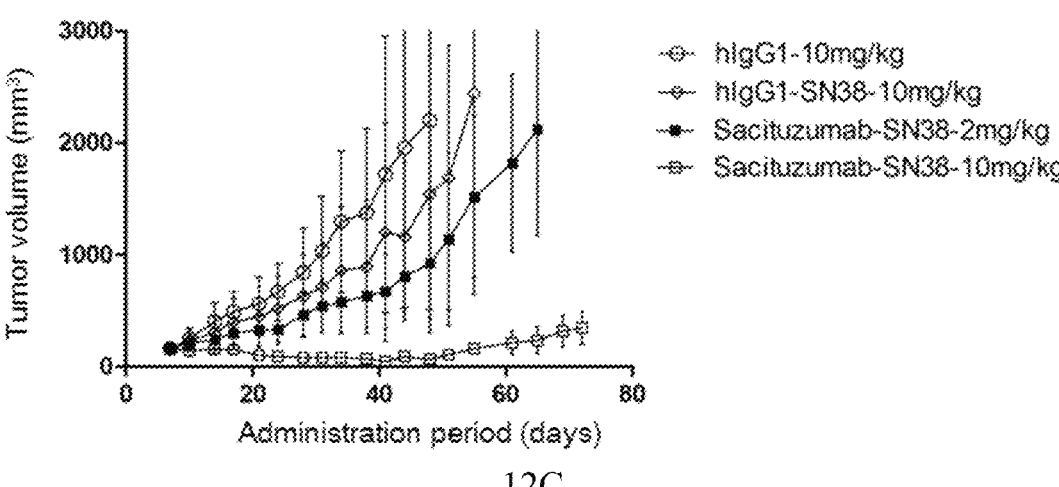
12C
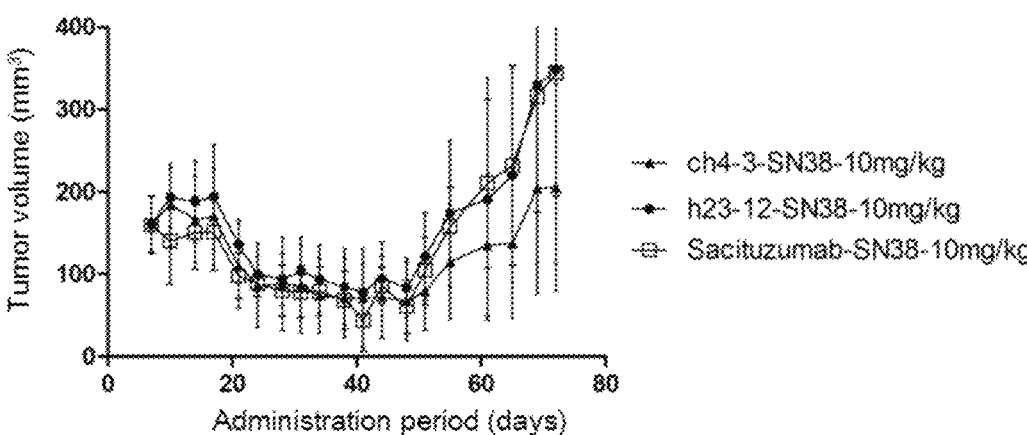
12D

ANTI-HUMAN TROP-2 ANTIBODY AND APPLICATION THEREOF

The present application claims the priority benefit of Chinese Patent Application No. CN201910962965.1 filed on 11 Oct. 2019, which is hereby incorporated by reference in its entirety.

CROSS-REFERENCE TO RELATED APPLICATIONS

The present application is a U.S. National Phase Patent Application of International Application Number PCT/CN2020/120277, filed on Oct. 12, 2020, which claims the priority benefit of Chinese Patent Application No. CN201910962965.1, filed on 11 Oct. 2019, the entire content of each of which is hereby incorporated by reference.

SEQUENCE LISTING

The instant application contains a Sequence Listing previously submitted to WIPO in ASCII format and the entire content of the electronic submission of the sequence listing is incorporated by reference in its entirety for all purposes. The ASCII file is named "LC20210009P-seq1.txt," was last modified on Apr. 15, 2021, and is 59.1 bytes in size. A substitute Sequence Listing is filed electronically herewith, the contents of which are incorporated by reference in their entirety. The electronic file was created on Aug. 25, 2025, is identical, 146,399 bytes in size, and titled "LC20210009Pseq1002.xml".

TECHNICAL FIELD

The present invention belongs to the field of biomedicine, and relates to a novel anti-human Trop-2 antibody or a functional fragment thereof. The present invention also relates to the use of the antibody or functional fragment thereof.

BACKGROUND OF THE INVENTION

Human trophoblast cell-surface antigen Trop-2, also known as Tumor-associated calcium signal transducer (TACSTD2), epithelial glycoprotein-1 antigen (EGP-1), gastrointestinal tumor-associated antigen 1 (GA733-1), is a cell surface glycoprotein encoded by TACSTD2 gene. Trop-2 has a full length of 323 amino acids, with an extracellular domain consisting of 3 regions, and is confirmed to exist in a dimer form.

Trop-2 is a transmembrane glycoprotein and unlike other proto-oncogenes, Trop-2 has no mutations, which means it has no genetic makeup alterations that lead to overexpression. Trop-2 stimulates cell growth through ERK/MAPK and cyclin D1 pathways, thereby promoting tumor invasion, angiogenesis, tumor progression, drug resistance and other mechanisms. Trop-2 has been found to be highly expressed in a variety of tumors, particularly triple negative breast cancer, non-small cell lung cancer, and the like, and is associated with prognosis. In contrast, Trop-2 has extremely low expression in normal tissues and is an ideal target for ADC medicines.

Antibody drugs targeting to Trop-2 currently developed are mainly antibody-drug conjugates (ADCs). According to incomplete statistics, more than 3 are clinically investigated, in which the small molecule drugs mainly comprise Irinotecan derivatives and Tubulin inhibitors. It is presently believed that it is desirable to use SN-38, a novel and low-toxicity metabolite of topoisomerase inhibitor. SN-38 has a different inhibition mechanism of tumors from existing microtubule inhibitors and DNA alkylating agents, and is particularly suitable for tumors with high heterogeneity and multi-drug resistance mechanism, such as three-negative breast cancer, pancreatic cancer, gastric cancer and the like. The most rapidly progressing ADC in clinic is IMMU-132 developed by Immunomedics, which has entered Phase III clinical trial for treatment of relapsed and metastatic triple-negative breast cancer (ASCENT-Study), phase II clinical trial for treatment of triple-negative breast cancer alone or in combination with carboplatin (NCT02161679), phase II clinical trial for treatment of urothelial cancer (NCT03547973), phase I/phase II clinical trial for treatment of solid tumors including gastric cancer, cervical cancer, small cell lung cancer (NCT01631552), and the like. Other antibody-drug conjugates with similar technologies are those developed by Daiichi Sankyo Company Limited, Pfizer Inc., and other pharmaceutical companies having ADC developing basis.

At present, there are less clinically investigated anti-Trop-2 antibodies. Therefore, there remains a need in the art to find new anti-Trop-2 antibodies that are particularly suitable for the development of ADCs. Trop-2 in early research shows a good application prospect as a tumor therapeutic target. However, the structure and the biological function of epitope sequence in Trop-2 are unclear, so high-affinity monoclonal antibodies obtained in earlier in-vitro screening in developing anti-Trop-2 monoclonal antibody drugs often show lower tumor targeting activity and inferior cytotoxin delivering capacity in in-vivo tests, which directly leads to a situation that yet no anti-Trop-2 monoclonal antibody drugs have completed clinical effectiveness trials so far.

SUMMARY OF THE INVENTION

Based on the mechanism of using Trop-2 as a target for tumor treatment in prior arts and the progress in clinical trials of anti-Trop-2 antibody drugs, the inventors found out through deep research and analysis, the reason that anti-Trop-2 antibodies do not get their theoretically expected effectiveness in preclinical tests and clinical trials not only purely lies in their insufficient affinity to Trop-2, but also in the fact that the best epitopes bound by the antibodies are typically in recombinant Trop-2 proteins or fragments thereof, rather than Trop-2 in its native conformation; accordingly, although high affinity antibodies against Trop-2 can be screened and obtained in vitro, their effective affinity for in vivo targeting Trop-2 extracellular domain in native conformation is still insufficient.

On one hand, there are many advantages if a recombinant protein is used as an immunogen and a coating antigen: easy purification of the immunogen, single structure of the exogenous antigen, and easy screening of a monoclonal antibody aiming at the recombinant protein. However, modification (e.g., glycosylation), folding pattern, etc. of the recombinantly expressed protein are often affected by the recombinant expression system. Even if a mammalian expression system is adopted, the purified free recombinant Trop-2 or the extracellular domain thereof is different from the Trop-2 extracellular domain combined in the cell membrane surface of native conformation. This difference in protein conformation or spatial structure results in differences in the specificity of antibodies produced by immunization and the effective affinities of the antibodies for the native conformation of Trop-2 extracellular domain in vivo.

On the other hand, if cells positive for Trop-2 on cell membrane surface are used as an immunogen and a screening antigen, advantages are that the Trop-2 extracellular domain has a native conformation, and a monoclonal antibody having a high affinity for the Trop-2 extracellular domain in vitro is expected to have a high affinity for the Trop-2 extracellular domain of native conformation in vivo. However, cells positive for Trop-2 on cell membrane surface are too complicated per se, and when such cells are used as an immunogen, the immunogenicity of the Trop-2 extracellular domain is susceptible to being shield; in addition, a flow cytometry-based screening if performed with cells positive for Trop-2 on cell membrane surface as a screening antigen is of high cost and low screening efficiency.

On the basis of previous research reports, the advantages and disadvantages of various technical routes for preparing monoclonal antibodies using recombinant Trop-2 protein and the Trop-2 positive cells were weighed, and a new technical route is proposed in the present invention, in which a recombinant Trop-2 protein is used as an immunogen to immunize animals to prepare hybridoma cells, so that the shielding effect on Trop-2 when a complicated antigen is used as an immunogen is avoided; the recombinant Trop-2 protein is used as a coating antigen and primary screening is carried out through ELISA screening, so that the screening is high throughout; and hybridomas which are positive in the primary screening are rescreened using cells positive for Trop-2 on membrane surface to ensure the obtained positive antibodies are able to bind the Trop-2 extracellular domain of native conformation.

The present invention further aims to solve the technical problem that how to make the performance of an anti-Trop-2 monoclonal antibody in preclinical phase of animal testing closer to the real in-vivo test result in a human body. For this purpose, in the technical route proposed in the present disclosure, monoclonal antibodies capable of specifically binding to the common structure of human Trop-2 extracellular domain and cynomolgus Trop-2 extracellular domain are obtained by species cross reactivity screening based on the common structure of human Trop-2 extracellular domain and cynomolgus Trop-2 extracellular domain; and to ensure high specificity of the anti-Trop-2 mabs, antibodies with specific binding ability to murine Trop-2 extracellular domain are excluded.

For the technical problems described above, the present disclosure provides an anti-Trop-2 antibody through hybridoma screening and humanization technologies, which has high affinity to human Trop-2 and specific killing effect on cancer cells; meanwhile, has high internalization ability, and is particularly suitable for developing ADC drugs.

Specifically, the present disclosure provides the following technical solutions.

In one aspect, the present disclosure provides a method for preparing an anti-Trop-2 monoclonal antibody, including steps as follows:

(1) preparing hybridoma cells by immunizing an animal with recombinant Trop-2 protein as an immunogen;

(2) screening positive hybridoma cells secreting anti-Trop-2 monoclonal antibodies using the recombinant Trop-2 protein as a coating antigen;

(3) rescreening the positive hybridoma cells obtained in step (2) using cells positive for Trop-2 on cell membrane surface;

wherein the anti-Trop-2 monoclonal antibody specifically recognizes and binds a natural epitope of Trop-2 extracellular domain.

Preferably, in the method for preparing an anti-Trop-2 monoclonal antibody according to the present disclosure, the cells positive for Trop-2 on cell membrane surface in step (3) are recombinant animal cells from the same species as the animal immunized when the hybridoma cells are prepared in step (1).

More preferably, in the method for preparing an anti-Trop-2 monoclonal antibody according to the present disclosure, in step (1) the hybridoma cells are prepared by immunizing a mouse, and in step (3) the cells positive for Trop-2 on cell membrane surface are recombinant mouse cells expressing exogenous Trop-2 protein.

Preferably, in the method for preparing an anti-Trop-2 monoclonal antibody according to the present disclosure, in step (2) the positive hybridoma cells secreting anti-Trop-2 monoclonal antibodies are screened using enzyme-linked immunosorbent assay (ELISA); and in step (3) the rescreening is performed by flow cytometry (FACS) analysis to obtain a hybridoma secreting an antibody specifically recognizing and binding a natural epitope of Trop-2 extracellular domain.

Preferably, the method for preparing an anti-Trop-2 monoclonal antibody according to the present disclosure further includes step (4): identifying the antibody specifically recognizing and binding a natural epitope of Trop-2 extracellular domain, wherein the identifying comprises affinity identification and specificity identification.

Preferably, in the method for preparing an anti-Trop-2 monoclonal antibody according to the disclosure, in step (4) a monoclonal antibody having a specific binding ability to human Trop-2 and cynomolgus Trop-2 but not to murine Trop-2 is selected.

In another aspect, the present disclosure provides an antibody or fragment thereof comprising a heavy chain variable region (VH) and a light chain variable region (VL), wherein the heavy chain variable region (VH) and the light chain variable region (VL) comprise a combination of CDRs (HCDR1, HCDR2, HCDR3; and LCDR1, LCDR2, LCDR3) selected from the group consisting of:

(1) HCDR1: SYWMY (SEQ ID NO: 61); HCDR2: EINPSNGRTNYNEKFKS (SEQ ID NO: 66); HCDR3: EGHNYDGSLGAMDH (SEQ ID NO: 74); LCDR1: RSSQSLTNSYGNTFLS (SEQ ID NO: 83); LCDR2: GISNRFS (SEQ ID NO: 92); and LCDR3: FQSTHQPYT (SEQ ID NO: 101);

(2) HCDR1: DYVIG (SEQ ID NO: 62); HCDR2: EIYLGSGTIYYTEKFKG (SEQ ID NO: 67); HCDR3: GSIFPFDY (SEQ ID NO: 75); LCDR1: SASSSVSYMY (SEQ ID NO: 84); LCDR2: DTST-LAS (SEQ ID NO: 93); and LCDR3: QQWSSYPYT (SEQ ID NO: 102);

(3) HCDR1: DYVIG (SEQ ID NO: 62); HCDR2: EIYLGSGTIYYAEKFKG (SEQ ID NO: 68); HCDR3: GSIFPFDY (SEQ ID NO: 75); LCDR1: SASSSVSYMY (SEQ ID NO: 84); LCDR2: DTST-LAS (SEQ ID NO: 93); and LCDR3: QQWSSYPYT (SEQ ID NO: 102);

(4) HCDR1: DYVIG (SEQ ID NO: 62); HCDR2: EIYLGSGTIYYTEKFKG (SEQ ID NO: 67); HCDR3: GSIFPFDY (SEQ ID NO: 75); LCDR1: RASSSVSYMY (SEQ ID NO: 85); LCDR2: DTST-LAS (SEQ ID NO: 93); and LCDR3: QQWSSYPYT (SEQ ID NO: 102);

(5) HCDR1: DYVIG (SEQ ID NO: 62); HCDR2: EIYLGSGTIYYAEKFKG (SEQ ID NO: 68); HCDR3: GSIFPFDY (SEQ ID NO: 75); LCDR1: RASSSVSYMY (SEQ ID NO: 85); LCDR2: DTST-LAS (SEQ ID NO: 93); and LCDR3: QQWSSYPYT (SEQ ID NO: 102);

(6) HCDR1: DYVIG (SEQ ID NO: 62); HCDR2: EIYLGSGTIYYTEKFKG (SEQ ID NO: 67); HCDR3: GSIFPFDY (SEQ ID NO: 75); LCDR1: SASSSVSYMY (SEQ ID NO: 84); LCDR2: DAST-LAS (SEQ ID NO: 94); and LCDR3: QQWSSYPYT (SEQ ID NO: 102);

(7) HCDR1: DYVIG (SEQ ID NO: 62); HCDR2: EIYLGSGTIYYTEKFKG (SEQ ID NO: 67); HCDR3: GSIFPFDY (SEQ ID NO: 75); LCDR1: SASSSVSYMY (SEQ ID NO: 84); LCDR2: DTSTLQS (SEQ ID NO: 95); and LCDR3: QQWSSY-PYT (SEQ ID NO: 102);

(8) HCDR1: SYWIN (SEQ ID NO: 63); HCDR2: NIYPSNSYTNYNQKFKD (SEQ ID NO: 69); HCDR3: YRSDGFAY (SEQ ID NO: 76); LCDR1: RASQNIGTSIH (SEQ ID NO: 86); LCDR2: FASESIS (SEQ ID NO: 96); and LCDR3: QQSNSWPFT (SEQ ID NO: 103);

(9) HCDR1: SYWIN (SEQ ID NO: 63); HCDR2: NIYPSNSYTNYNQKFKD (SEQ ID NO: 69); HCDR3: YRSDGFAY (SEQ ID NO: 76); LCDR1: RASQNIGTSIE (SEQ ID NO: 87); LCDR2: FASESIS (SEQ ID NO: 96); and LCDR3: QQSNSWPFT (SEQ ID NO: 103);

(10) HCDR1: SYWIN (SEQ ID NO: 63); HCDR2: NIYPSNSYTNYNQKFKD (SEQ ID NO: 69); HCDR3: YRSEGFAY (SEQ ID NO: 77); LCDR1: RASQNIGTSIE (SEQ ID NO: 87); LCDR2: FASESIS (SEQ ID NO: 96); and LCDR3: QQSNSWPFT (SEQ ID NO: 103);

(11) HCDR1: SYWIN (SEQ ID NO: 63); HCDR2: NIYPSNSYTNYNQKFKD (SEQ ID NO: 69); HCDR3: YRSGGFAY (SEQ ID NO: 78); LCDR1: RASQNIGTSIE (SEQ ID NO: 87); LCDR2: FASESIS (SEQ ID NO: 96); and LCDR3: QQSNSWPFT (SEQ ID NO: 103);

(12) HCDR1: SYWIN (SEQ ID NO: 63); HCDR2: NIYPSNSYTNYNQKFKD (SEQ ID NO: 69); HCDR3: YRSDAFAY (SEQ ID NO: 79); LCDR1: RASQNIGTSIE (SEQ ID NO: 87); LCDR2: FASESIS (SEQ ID NO: 96); and LCDR3: QQSNSWPFT (SEQ ID NO: 103);

(13) HCDR1: SYWIN (SEQ ID NO: 63); HCDR2: NIYPSNSYTNYNQKFKD (SEQ ID NO: 69); HCDR3: YRSDGFAY (SEQ ID NO: 76); LCDR1: RASQNIGTSIS (SEQ ID NO: 88); LCDR2: FASESIS (SEQ ID NO: 96); and LCDR3: QQSNSWPFT (SEQ ID NO: 103);

(14) HCDR1: SYWIN (SEQ ID NO: 63); HCDR2: NIYPSNSYTNYNQKFKD (SEQ ID NO: 69); HCDR3: YRSEGFAY (SEQ ID NO: 77); LCDR1: RASQNIGTSIS (SEQ ID NO: 88); LCDR2: FASESIS (SEQ ID NO: 96); and LCDR3: QQSNSWPFT (SEQ ID NO: 103);

(15) HCDR1: SYWIN (SEQ ID NO: 63); HCDR2: NIYPSNSYTNYNQKFKD (SEQ ID NO: 69); HCDR3: YRSGGFAY (SEQ ID NO: 78); LCDR1: RASQNIGTSIS (SEQ ID NO: 88); LCDR2: FASESIS (SEQ ID NO: 96); and LCDR3: QQSNSWPFT (SEQ ID NO: 103);

(16) HCDR1: SYWIN (SEQ ID NO: 63); HCDR2: NIYPSNSYTNYNQKFKD (SEQ ID NO: 69); HCDR3: YRSDAFAY (SEQ ID NO: 79); LCDR1: RASQNIGTSIS (SEQ ID NO: 88); LCDR2: FASESIS (SEQ ID NO: 96); and LCDR3: QQSNSWPFT (SEQ ID NO: 103);

(17) HCDR1: SYWIN (SEQ ID NO: 63); HCDR2: NIYPSNSYTNYNQKFKD (SEQ ID NO: 69); HCDR3: YRSDGFAY (SEQ ID NO: 76); LCDR1: RASQNIGTSIA (SEQ ID NO: 89); LCDR2: FASESIS (SEQ ID NO: 96); and LCDR3: QQSNSWPFT (SEQ ID NO: 103);

(18) HCDR1: SYWIN (SEQ ID NO: 63); HCDR2: NIYPSNSYTNYNQKFKD (SEQ ID NO: 69); HCDR3: YRSEGFAY (SEQ ID NO: 77); LCDR1: RASQNIGTSIA (SEQ ID NO: 89); LCDR2: FASESIS (SEQ ID NO: 96); and LCDR3: QQSNSWPFT (SEQ ID NO: 103);

(19) HCDR1: SYWIN (SEQ ID NO: 63); HCDR2: NIYPSNSYTNYNQKFKD (SEQ ID NO: 69); HCDR3: YRSGGFAY (SEQ ID NO: 78); LCDR1: RASQNIGTSIA (SEQ ID NO: 89); LCDR2: FASESIS (SEQ ID NO: 96); and LCDR3: QQSNSWPFT (SEQ ID NO: 103);

(20) HCDR1: SYWIN (SEQ ID NO: 63); HCDR2: NIYPSNSYTNYNQKFKD (SEQ ID NO: 69); HCDR3: YRSDAFAY (SEQ ID NO: 79); LCDR1: RASQNIGTSIA (SEQ ID NO: 89); LCDR2: FASESIS (SEQ ID NO: 96); and LCDR3: QQSNSWPFT (SEQ ID NO: 103);

(21) HCDR1: DSAMS (SEQ ID NO: 64); HCDR2: SISRGDDTYYPDSVKG (SEQ ID NO: 70); HCDR3: DRFGFAY (SEQ ID NO: 80); LCDR1: KSGQSLL-DSDGKTYFN (SEQ ID NO: 90); LCDR2: LVSMLDS (SEQ ID NO: 97); and LCDR3: WQGTHFPFT (SEQ ID NO: 104);

(22) HCDR1: SYWMH (SEQ ID NO: 65); HCDR2: EITPSDNYTSYNQKFKG (SEQ ID NO: 71); HCDR3: GHGNYVSFDY (SEQ ID NO: 81); LCDR1: RASQDISNYLN (SEQ ID NO: 91); LCDR2: YTSRLHS (SEQ ID NO: 98); and LCDR3: QQGTLPPYT (SEQ ID NO: 105);

(23) HCDR1: SYWMH (SEQ ID NO: 65); HCDR2: EITPSDNYTSYNQKFKG (SEQ ID NO: 71); HCDR3: GEGNYVSFDY (SEQ ID NO: 82); LCDR1: RASQDISNYLN (SEQ ID NO: 91); LCDR2: YTSRLHS (SEQ ID NO: 98); and LCDR3: QQGYTLPPYT (SEQ ID NO: 105);

(24) HCDR1: SYWMH (SEQ ID NO: 65); HCDR2: EITPSDNYGSYNQKFKG (SEQ ID NO: 72); HCDR3: GHGNYVSFDY (SEQ ID NO: 81); LCDR1: RASQDISNYLN (SEQ ID NO: 91); LCDR2: YTSR-LES (SEQ ID NO: 99); and LCDR3: QQGYTLPPYT (SEQ ID NO: 105);

(25) HCDR1: SYWMH (SEQ ID NO: 65); HCDR2: EITPSDNYTSYNQKFKG (SEQ ID NO: 71); HCDR3: GEGNYVSFDY (SEQ ID NO: 82); LCDR1: RASQDISNYLN (SEQ ID NO: 91); LCDR2: YTSR-LES (SEQ ID NO: 99); and LCDR3: QQGYTLPPYT (SEQ ID NO: 105);

(26) HCDR1: SYWMH (SEQ ID NO: 65); HCDR2: EITPSDNYGSYNQKFKG (SEQ ID NO: 72); HCDR3: GHGNYVSFDY (SEQ ID NO: 81); LCDR1: RASQDISNYLN (SEQ ID NO: 91); LCDR2: YTSRLQS (SEQ ID NO: 100); and LCDR3: QQGYTLPPYT (SEQ ID NO: 105);

(27) HCDR1: SYWMH (SEQ ID NO: 65); HCDR2: EITPSDNYGSYNQKFKG (SEQ ID NO: 72); HCDR3: GHGNYVSFDY (SEQ ID NO: 81); LCDR1: RASQDISNYLN (SEQ ID NO: 91); LCDR2: YTSRLHS (SEQ ID NO: 98); and LCDR3: QQYYTLPPYT (SEQ ID NO: 106);

(28) HCDR1: SYWMH (SEQ ID NO: 65); HCDR2: EITPGDNYTSYNQKFKG (SEQ ID NO: 73); HCDR3: GHGNYVSFDY (SEQ ID NO: 81); LCDR1: RASQDISNYLN (SEQ ID NO: 91); LCDR2: YTSRLHS (SEQ ID NO: 98); and LCDR3: QQGYS-LPPYT (SEQ ID NO: 107);

(29) HCDR1: SYWMH (SEQ ID NO: 65); HCDR2: EITPSDNYGSYNQKFKG (SEQ ID NO: 72); HCDR3: GHGNYVSFDY (SEQ ID NO: 81); LCDR1: RASQDISNYLN (SEQ ID NO: 91); LCDR2: YTSRLHS (SEQ ID NO: 98); and LCDR3: QQGYS-LPPYT (SEQ ID NO: 107); and

(30) HCDR1: SYWMH (SEQ ID NO: 65); HCDR2: EITPSDNYTSYNQKFKG (SEQ ID NO: 71); HCDR3: GEGNYVSFDY (SEQ ID NO: 82); LCDR1: RASQDISNYLN (SEQ ID NO: 91); LCDR2: YTSRLHS (SEQ ID NO: 98); and LCDR3: QQGYS-LPPYT (SEQ ID NO: 107).

The antibody or fragment thereof binds to human Trop-2.

Preferably, the heavy chain variable region comprises an amino acid sequence as shown in any one of SEQ ID NOs: 1 to 17 or an amino acid sequence having at least 75% identity to the amino acid sequence as shown; and/or, the light chain variable region comprises an amino acid sequence as shown in any one of SEQ ID NOs: 18 to 36 or an amino acid sequence having at least 75% identity to the amino acid sequence as shown.

According to a particular embodiment of the present disclosure, the heavy chain variable region and the light chain variable region comprised by the antibody or fragment thereof of the present disclosure comprise one of the following:

(1) an amino acid sequence as shown in SEQ ID NO: 1 or an amino acid sequence having at least 75% identity to the amino acid sequence as shown in SEQ ID NO: 1; and, an amino acid sequence as shown in SEQ ID NO: 18 or an amino acid sequence having at least 75% identity to the amino acid sequence as shown in SEQ ID NO: 18;

(2) an amino acid sequence as shown in SEQ ID NO: 2 or an amino acid sequence having at least 75% identity to the amino acid sequence as shown in SEQ ID NO: 2; and, an amino acid sequence as shown in SEQ ID NO: 19 or an amino acid sequence having at least 75% identity to the amino acid sequence as shown in SEQ ID NO: 19;

(3) an amino acid sequence as shown in SEQ ID NO: 3 or an amino acid sequence having at least 75% identity to the amino acid sequence as shown in SEQ ID NO: 3; and, an amino acid sequence as shown in SEQ ID NO: 20 or an amino acid sequence having at least 75% identity to the amino acid sequence as shown in SEQ ID NO: 20;

(4) an amino acid sequence as shown in SEQ ID NO: 4 or an amino acid sequence having at least 75% identity to the amino acid sequence as shown in SEQ ID NO: 4; and, an amino acid sequence as shown in SEQ ID NO: 20 or an amino acid sequence having at least 75% identity to the amino acid sequence as shown in SEQ ID NO: 20;

(5) an amino acid sequence as shown in SEQ ID NO: 3 or an amino acid sequence having at least 75% identity to the amino acid sequence as shown in SEQ ID NO: 3; and, an amino acid sequence as shown in SEQ ID NO: 21 or an amino acid sequence having at least 75% identity to the amino acid sequence as shown in SEQ ID NO: 21;

(6) an amino acid sequence as shown in SEQ ID NO: 4 or an amino acid sequence having at least 75% identity to the amino acid sequence as shown in SEQ ID NO: 4; and, an amino acid sequence as shown in SEQ ID NO: 21 or an amino acid sequence having at least 75% identity to the amino acid sequence as shown in SEQ ID NO: 21;

(7) an amino acid sequence as shown in SEQ ID NO: 3 or an amino acid sequence having at least 75% identity to the amino acid sequence as shown in SEQ ID NO: 3; and, an amino acid sequence as shown in SEQ ID NO: 22 or an amino acid sequence having at least 75% identity to the amino acid sequence as shown in SEQ ID NO: 22;

(8) an amino acid sequence as shown in SEQ ID NO: 3 or an amino acid sequence having at least 75% identity to the amino acid sequence as shown in SEQ ID NO: 3; and, an amino acid sequence as shown in SEQ ID NO: 23 or an amino acid sequence having at least 75% identity to the amino acid sequence as shown in SEQ ID NO: 23;

(9) an amino acid sequence as shown in SEQ ID NO: 5 or an amino acid sequence having at least 75% identity to the amino acid sequence as shown in SEQ ID NO: 5; and, an amino acid sequence as shown in SEQ ID NO: 24 or an amino acid sequence having at least 75% identity to the amino acid sequence as shown in SEQ ID NO: 24;

(10) an amino acid sequence as shown in SEQ ID NO: 6 or an amino acid sequence having at least 75% identity to the amino acid sequence as shown in SEQ ID NO: 6; and, an amino acid sequence as shown in SEQ ID NO: 25 or an amino acid sequence having at least 75% identity to the amino acid sequence as shown in SEQ ID NO: 25;

(11) an amino acid sequence as shown in SEQ ID NO: 7 or an amino acid sequence having at least 75% identity to the amino acid sequence as shown in SEQ ID NO: 7; and, an amino acid sequence as shown in SEQ ID NO: 26 or an amino acid sequence having at least 75% identity to the amino acid sequence as shown in SEQ ID NO: 26;

(12) an amino acid sequence as shown in SEQ ID NO: 7 or an amino acid sequence having at least 75% identity to the amino acid sequence as shown in SEQ ID NO: 7; and, an amino acid sequence as shown in SEQ ID NO: 27 or an amino acid sequence having at least 75% identity to the amino acid sequence as shown in SEQ ID NO: 27;

(13) an amino acid sequence as shown in SEQ ID NO: 8 or an amino acid sequence having at least 75% identity to the amino acid sequence as shown in SEQ ID NO: 8; and, an amino acid sequence as shown in SEQ ID NO: 27 or an amino acid sequence having at least 75% identity to the amino acid sequence as shown in SEQ ID NO: 27;

(14) an amino acid sequence as shown in SEQ ID NO: 9 or an amino acid sequence having at least 75% identity to the amino acid sequence as shown in SEQ ID NO: 9; and, an amino acid sequence as shown in SEQ ID NO: 27 or an amino acid sequence having at least 75% identity to the amino acid sequence as shown in SEQ ID NO: 27;

(15) an amino acid sequence as shown in SEQ ID NO: 10 or an amino acid sequence having at least 75% identity to the amino acid sequence as shown in SEQ ID NO: 10; and, an amino acid sequence as shown in SEQ ID NO: 27 or an amino acid sequence having at least 75% identity to the amino acid sequence as shown in SEQ ID NO: 27;

(16) an amino acid sequence as shown in SEQ ID NO: 7 or an amino acid sequence having at least 75% identity to the amino acid sequence as shown in SEQ ID NO: 7; and, an amino acid sequence as shown in SEQ ID NO: 28 or an amino acid sequence having at least 75% identity to the amino acid sequence as shown in SEQ ID NO: 28;

(17) an amino acid sequence as shown in SEQ ID NO: 8 or an amino acid sequence having at least 75% identity to the amino acid sequence as shown in SEQ ID NO: 8; and, an amino acid sequence as shown in SEQ ID NO: 28 or an amino acid sequence having at least 75% identity to the amino acid sequence as shown in SEQ ID NO: 28;

(18) an amino acid sequence as shown in SEQ ID NO: 9 or an amino acid sequence having at least 75% identity to the amino acid sequence as shown in SEQ ID NO: 9; and, an amino acid sequence as shown in SEQ ID NO: 28 or an amino acid sequence having at least 75% identity to the amino acid sequence as shown in SEQ ID NO: 28;

(19) an amino acid sequence as shown in SEQ ID NO: 10 or an amino acid sequence having at least 75% identity to the amino acid sequence as shown in SEQ ID NO: 10; and, an amino acid sequence as shown in SEQ ID NO: 28 or an amino acid sequence having at least 75% identity to the amino acid sequence as shown in SEQ ID NO: 28;

(20) an amino acid sequence as shown in SEQ ID NO: 7 or an amino acid sequence having at least 75% identity to the amino acid sequence as shown in SEQ ID NO: 7; and, an amino acid sequence as shown in SEQ ID NO: 29 or an amino acid sequence having at least 75% identity to the amino acid sequence as shown in SEQ ID NO: 29;

(21) an amino acid sequence as shown in SEQ ID NO: 8 or an amino acid sequence having at least 75% identity to the amino acid sequence as shown in SEQ ID NO: 8; and, an amino acid sequence as shown in SEQ ID NO: 29 or an amino acid sequence having at least 75% identity to the amino acid sequence as shown in SEQ ID NO: 29;

(22) an amino acid sequence as shown in SEQ ID NO: 9 or an amino acid sequence having at least 75% identity to the amino acid sequence as shown in SEQ ID NO: 9; and, an amino acid sequence as shown in SEQ ID NO: 29 or an amino acid sequence having at least 75% identity to the amino acid sequence as shown in SEQ ID NO: 29;

(23) an amino acid sequence as shown in SEQ ID NO: 10 or an amino acid sequence having at least 75% identity to the amino acid sequence as shown in SEQ ID NO: 10; and, an amino acid sequence as shown in SEQ ID NO: 29 or an amino acid sequence having at least 75% identity to the amino acid sequence as shown in SEQ ID NO: 29;

(24) an amino acid sequence as shown in SEQ ID NO: 11 or an amino acid sequence having at least 75% identity to the amino acid sequence as shown in SEQ ID NO: 11; and, an amino acid sequence as shown in SEQ ID NO: 30 or an amino acid sequence having at least 75% identity to the amino acid sequence as shown in SEQ ID NO: 30;

(25) an amino acid sequence as shown in SEQ ID NO: 12 or an amino acid sequence having at least 75% identity to the amino acid sequence as shown in SEQ ID NO: 12; and, an amino acid sequence as shown in SEQ ID NO: 31 or an amino acid sequence having at least 75% identity to the amino acid sequence as shown in SEQ ID NO: 31;

(26) an amino acid sequence as shown in SEQ ID NO: 13 or an amino acid sequence having at least 75% identity to the amino acid sequence as shown in SEQ ID NO: 13; and, an amino acid sequence as shown in SEQ ID NO: 32 or an amino acid sequence having at least 75% identity to the amino acid sequence as shown in SEQ ID NO: 32;

(27) an amino acid sequence as shown in SEQ ID NO: 16 or an amino acid sequence having at least 75% identity to the amino acid sequence as shown in SEQ ID NO: 16; and, an amino acid sequence as shown in SEQ ID NO: 32 or an amino acid sequence having at least 75% identity to the amino acid sequence as shown in SEQ ID NO: 32;

(28) an amino acid sequence as shown in SEQ ID NO: 14 or an amino acid sequence having at least 75% identity to the amino acid sequence as shown in SEQ ID NO: 14; and, an amino acid sequence as shown in SEQ ID NO: 33 or an amino acid sequence having at least 75% identity to the amino acid sequence as shown in SEQ ID NO: 33;

(29) an amino acid sequence as shown in SEQ ID NO: 16 or an amino acid sequence having at least 75% identity to the amino acid sequence as shown in SEQ ID NO: 16; and, an amino acid sequence as shown in SEQ ID NO: 33 or an amino acid sequence having at least 75% identity to the amino acid sequence as shown in SEQ ID NO: 33;

(30) an amino acid sequence as shown in SEQ ID NO: 14 or an amino acid sequence having at least 75% identity to the amino acid sequence as shown in SEQ ID NO: 14; and, an amino acid sequence as shown in SEQ ID NO: 34 or an amino acid sequence having at least 75% identity to the amino acid sequence as shown in SEQ ID NO: 34;

(31) an amino acid sequence as shown in SEQ ID NO: 14 or an amino acid sequence having at least 75% identity to the amino acid sequence as shown in SEQ ID NO: 14; and, an amino acid sequence as shown in SEQ ID NO: 35 or an amino acid sequence having at least 75% identity to the amino acid sequence as shown in SEQ ID NO: 35;

(32) an amino acid sequence as shown in SEQ ID NO: 15 or an amino acid sequence having at least 75% identity to the amino acid sequence as shown in SEQ ID NO: 15; and, an amino acid sequence as shown in SEQ ID NO: 36 or an amino acid sequence having at least 75% identity to the amino acid sequence as shown in SEQ ID NO: 36;

(33) an amino acid sequence as shown in SEQ ID NO: 14 or an amino acid sequence having at least 75% identity to the amino acid sequence as shown in SEQ ID NO: 14; and, an amino acid sequence as shown in SEQ ID NO: 36 or an amino acid sequence having at least 75% identity to the amino acid sequence as shown in SEQ ID NO: 36; and

(34) an amino acid sequence as shown in SEQ ID NO: 16 or an amino acid sequence having at least 75% identity to the amino acid sequence as shown in SEQ ID NO: 16; and, an amino acid sequence as shown in SEQ ID NO: 36 or an amino acid sequence having at least 75% identity to the amino acid sequence as shown in SEQ ID NO: 36.

Typically, the antibody or fragment thereof is in any form, e.g., a monoclonal antibody, a single chain antibody, a diabody, a single domain antibody, a nanobody, a fully or partially humanized antibody, or a chimeric antibody and the like; alternatively, the antibody or fragment thereof is a half-antibody or an antigen-binding fragment of the half-antibody, e.g., single-chain variable fragment (scFv), bivalent single-chain variable fragment (BsFv), disulfide-stabilized Fv fragment (dsFv), (disulfide-stabilized Fv fragment)$_2$ (dsFv)$_2$, antigen-binding fragment (Fab), Fab' fragment, F(ab')$_2$ fragment, or variable fragment (Fv); and the antibody or fragment thereof can be of mouse, rat, human or any other origin.

Preferably, the antibody or fragment thereof further comprises a human or murine constant region, preferably a human or murine light chain constant region (CL) and/or heavy chain constant region (CH); more preferably, the antibody or fragment thereof comprises a heavy chain constant region selected from the group consisting of IgG, IgA, IgM, IgD and IgE and/or a kappa or lambda type light chain constant region.

According to a particular embodiment of the present disclosure, the antibody is a monoclonal antibody, preferably a murine, chimeric, or humanized monoclonal antibody; more preferably, the heavy chain constant region of the monoclonal antibody is of IgG1 or IgG4 subtype and the light chain constant region of the monoclonal antibody is of kappa type.

According to a particular embodiment of the disclosure, the heavy chain constant region of the monoclonal antibody comprises an amino acid sequence as shown in SEQ ID NO: 37 or an amino acid sequence having at least 75% identity to the amino acid sequence as shown; and preferably, the light chain constant region of the monoclonal antibody comprises an amino acid sequence as shown in SEQ ID NO: 38 or an amino acid sequence having at least 75% identity to the amino acid sequence as shown.

The at least 75% identity described above in the present disclosure is any percent identity greater than or equal to 75%, such as at least 80%, preferably at least 85%, more preferably at least 90%, even more preferably at least 91%, 92%, 93%, 94%, 95%, 96%, 97%, 98%, or even 99% identity.

Based on the antibody or fragment thereof of the present disclosure, in a further aspect, the present disclosure provides a nucleic acid molecule comprising a nucleotide sequence encoding a heavy chain CDR, a light chain CDR, a heavy chain variable region, a light chain variable region, a heavy chain or a light chain comprised in the antibody or fragment thereof according to the present disclosure.

In yet another aspect, the present disclosure provides a vector comprising the nucleic acid molecule of the present disclosure. The vector can be a eukaryotic expression vector, a prokaryotic expression vector, an artificial chromosome, a phage vector and the like.

The vector or nucleic acid molecule of the present disclosure may be used to transform or transfect a host cell or in any way enter a host cell for antibody preservation or expression, etc.

Thus, in a further aspect, the present disclosure provides a host cell comprising the nucleic acid molecule and/or vector according to the present disclosure, or transformed or transfected with the nucleic acid molecule and/or vector according to the present disclosure. The host cell may be any prokaryotic or eukaryotic cell, such as a bacterial or insect, fungus, plant or animal cell.

According to the disclosure of the present embodiments, the antibody or fragment thereof, the nucleic acid molecule, the vector, and/or the host cell provided by the present disclosure can be obtained using any conventional techniques known in the art. The antibody or fragment thereof, the nucleic acid molecule, the vector, and/or the host cell provided by the present disclosure may be contained in a pharmaceutical composition, more particularly, a pharmaceutical preparation, to be used for various purposes as actually needed.

Thus, in still a further aspect, the present disclosure also provides a pharmaceutical composition comprising an antibody or fragment thereof, a nucleic acid molecule, a vector, and/or a host cell according to the present disclosure, and optionally a pharmaceutically acceptable excipient.

The antibody or fragment thereof of the present disclosure can be used in combination with other antibody-based drugs capable of inducing phagocytosis by macrophages. Therefore, preferably, the antibody-based drugs promote phagocytosis of cells by macrophages through binding to proteins expressed on surface of the cells. Therefore, the pharmaceutical composition provided by the present disclosure can comprise a further antibody-based drug, preferably an antibody against macrophage-related immune checkpoint. According to a particular embodiment of the disclosure, the antibody is an anti-CD47 antibody.

The disclosure also provides related uses of the subject matters described above according to the antibody binding to human Trop-2 or any portion thereof.

In particular, in a further aspect, the disclosure provides the use of the antibody or fragment thereof, the nucleic acid molecule, the vector, the host cell and/or the pharmaceutical composition in the manufacture of a medicament, preferably for treating a Trop-2 high expression cancer. Preferably, the Trop-2 high expression cancer is gastric cancer, pancreatic cancer, intestinal cancer, ovarian cancer, squamous lung cancer, non-small cell lung cancer, small cell lung cancer, urothelial cancer, triple negative breast cancer, or cervical cancer.

In this respect, the use encompasses the use of an antibody or fragment thereof of the present disclosure in combination with other antibody-based drugs as described above in the manufacture of the medicament.

The antibody or fragment thereof provided by the present disclosure may also be fused or conjugated to other moieties. For example, the disclosure provides a fusion protein or conjugate comprising an antibody or fragment thereof according to the present disclosure.

With respect to a fusion protein, the fusion protein may comprise any other moiety, such as an amino acid, polypeptide, or protein, which modifies the antibody or fragment thereof of the present disclosure.

With respect to a conjugate, the conjugate may comprise an antibody or fragment thereof of the present disclosure and a drug conjugated thereto, wherein the drug is, for example, a cytotoxic agent.

Preferably, the conjugate is an antibody drug conjugate (ADC) represented by the formula: (an antibody or fragment thereof according to the present disclosure)-(linker)-(a cytotoxic agent); preferably, the cytotoxic agent is a tubulin inhibitor (such as paclitaxel, docetaxel, etc.) or a DNA replication inhibitor (such as irinotecan or its active metabolite SN-38, etc.).

According to a particular embodiment of the disclosure, the conjugate is an "anti-TROP-2 antibody-linker-SN-38 antibody drug conjugate"

The present disclosure also provides the use of the antibody or fragment thereof, the nucleic acid molecule, the vector, the host cell and/or the pharmaceutical composition in the manufacture of an antibody drug conjugate (ADC), preferably for treating a Trop-2 high expression cancer. Preferably, the Trop-2 high expression cancer is gastric cancer, pancreatic cancer, intestinal cancer, ovarian cancer, squamous lung cancer, non-small cell lung cancer, small cell lung cancer, urothelial cancer, triple negative breast cancer, or cervical cancer.

In addition, the present disclosure provides a method for preventing and/or treating a disease, including administering to a subject in need thereof an antibody or fragment thereof, a nucleic acid molecule, a vector, a host cell, a pharmaceutical composition, a fusion protein, or a conjugate according to the present disclosure, and optionally other drug or means. The optional other drug or means refers to other drug or means that can be administered in combination with the antibody or fragment thereof, the nucleic acid molecule, the vector, the host cell, the pharmaceutical composition, the fusion protein or the conjugate of the present disclosure, such as a small molecule drug, a targeted drug, a recombinant protein drug such as an antibody, a vaccine, an ADC, an oncolytic virus, a gene or nucleic acid therapy drug and radiotherapy. The co-administration of the two may be in any way, including simultaneously, sequentially or at intervals.

Preferably, the disease is a Trop-2 high expression cancer; further preferably, the Trop-2 high expression cancer is gastric cancer, pancreatic cancer, intestinal cancer, ovarian cancer, squamous lung cancer, non-small cell lung cancer, small cell lung cancer, urothelial cancer, triple negative breast cancer or cervical cancer. The subject is a mammal; preferably, the subject is a human.

Unless otherwise indicated, term "immunoglobulin sequence" is used as a general term encompassing full-size antibodies, individual chains thereof, and all portions, domains or fragments thereof (including but not limited to antigen-binding domains or fragments such as VHH domains or VH/VL domains, respectively).

Term "antibody" is understood to encompass an antibody molecule comprising two immunoglobulin heavy chains and two immunoglobulin light chains (i.e., "a full antibody molecule") as well as an antigen-binding fragment thereof. Terms "antigen-binding portion" of an antibody, "antigen-binding fragment" of an antibody, and the like, as used herein, encompass any naturally occurring, enzymatically obtainable, synthetic, or genetically engineered polypeptide or glycoprotein that specifically binds an antigen to form a complex. Terms "antigen-binding fragment" of an antibody, or "antibody fragment", as used herein, refers to one or more fragments of an antibody that retain the ability to specifically bind to Trop-2. An antibody fragment may include a Fab fragment, a F(ab') 2 fragment, a Fv fragment, a dAb fragment, a fragment containing a CDR, or an isolated CDR. An antigen-binding fragment of an antibody may be derived, e.g., from a full antibody molecule using any suitable standard techniques such as proteolytic digestion or recombinant genetic engineering techniques involving the manipulation and expression of a DNA encoding antibody variable and (optionally) constant domain. Such DNA is known and/or is readily available from, e.g., a commercial source, a DNA library (including, e.g., a phage-antibody library), or can be synthesized. The DNA may be sequenced and manipulated chemically or by using molecular biology techniques, for example, to arrange one or more variable and/or constant domains into a suitable configuration, or to introduce codons; create cysteine residues; modify, add or delete amino acids, etc.

Non-limiting examples of an antigen-binding fragment include: (i) Fab fragment; (ii) $F(ab')_2$ fragment; (iii) Fd fragment; (iv) Fv fragment; (v) single-chain Fv (scFv) molecule; (vi) dAb fragment; and (vii) minimal recognition unit consisting of the amino acid residues that mimic the hypervariable region of an antibody (e.g., an isolated complementarity determining region (CDR) such as a CDR3 peptide), or a constrained FR3-CDR3-FR4 peptide. Other engineered molecules, such as a domain-specific antibody, a single-domain antibody, a domain-deleted antibody, a chimeric antibody, a CDR-grafted antibody, a diabody, a triabody, a tetrabody, a minibody, a nanobody (e.g. a monovalent nanobody, a bivalent nanobody, etc.), a small modular immunopharmaceutical (SMIP), and a shark variable IgNAR domain, are also encompassed within the expression "antigen-binding fragment" as used herein.

An antigen-binding fragment of an antibody will typically comprise at least one variable domain. The variable domain may be of any size or amino acid composition and will generally comprise at least one CDR, which is adjacent to or in frame with one or more framework sequences. In an antigen-binding fragment having a VH domain associated with a VL domain, the VH and VL domains may be situated relative to one another in any suitable arrangement. For example, the variable region may be dimeric and contain VH-VH, VH-VL or VL-VL dimers. Alternatively, the antigen-binding fragment of an antibody may contain a monomeric VH or VL domain.

In certain embodiments, an antigen-binding fragment of an antibody may contain at least one variable domain covalently linked to at least one constant domain. Non-limiting, exemplary configurations of variable and constant domains that may be found within an antigen-binding fragment of an antibody according to the present disclosure include: (i) VH-CH1; (ii) VH-CH2; (iii) VH-CH3; (iv) VH-CH1-Ch2; (v) VH-CH1-CH2-CH3; (vi) VH-CH2-CH3; (vii) VH-CL; (viii) VL-CH1; (ix) VL-CH2; (x) VL-CH3; (xi) VL-CH1-CH2; (xii) VL-CH1-CH2-CH3; (xiii) VL-CH2-CH3; and (xiv) VL-CL. In any configuration of variable and constant domains, including any of the exemplary configurations listed above, the variable and constant domains may be either directly linked to one another or may be linked by a full or partial hinge or linker region. A hinge region may consist of at least 2 (e.g., 5, 10, 15, 20, 40, 60, or more) amino acids, which result in a flexible or semi-flexible linkage between adjacent variable and/or constant domains in a single polypeptide molecule. Moreover, an antigen-binding fragment of an antibody of the present disclosure may comprise a homodimer or heterodimer (or other multimer) of any of the variable and constant domain configurations listed above in non-covalent association with one another and/or with one or more monomeric VH or VL domain (e.g., by disulfide bonds).

As with a full antibody molecule, an antigen-binding fragment may be monospecific or multispecific (e.g., bispecific). A multispecific antigen-binding fragment of an antibody will typically comprise at least two different variable domains, in which each variable domain is capable of specifically binding to a separate antigen or to a different epitope on the same antigen. Any multispecific antibody format, including the exemplary bispecific antibody format disclosed herein, may be adapted for use in the context of an antigen-binding fragment of an antibody according to the present disclosure using routine techniques available in the art.

Term "chimeric antibody" refers to an antibody in which (a) the constant region or a portion thereof is altered, replaced or exchanged so that the antigen binding site (variable region, CDR, or portion thereof) is linked to a constant region of a different or altered class, effector function and/or species; or (b) the variable region or a portion thereof is altered, replaced or exchanged with a variable region having a different or altered antigen specificity (e.g., a CDR and framework region from different species). A chimeric antibody can comprise a variable region fragment, e.g., a recombinant antibody comprising two Fab or Fv regions or an scFv. As indicated above, a chimeric antibody can also comprise an Fc region from a different source than the attached Fv region. In some cases, a chimeric antibody comprises a chimeric region within the Fv region. An example of such a chimeric antibody is a humanized antibody in which the Fvs and CDRs are from different sources.

Term "humanized antibody" refers to an antibody in which the antigen binding loops, i.e., CDRs, obtained from the VH and VL regions of a non-human antibody are grafted to a human framework sequence. Humanization, i.e., substitution of non-human CDR sequences for the corresponding sequences of a human antibody, can be performed following the methods described in, e.g., U.S. Pat. Nos. 5,545,806; 5,569,825; 5,633,425; 5,661,016; Riechmann et al., Nature 332:323-327 (1988); Marks et al, Bio/Technology 10:779-783 (1992); Morrison, Nature 368:812-13 (1994); and Fishwild et al., Nature Biotechnology 14:845-51 (1996). Transgenic mice, or other organisms such as other mammals, may also be used to express humanized or human antibodies, as disclosed in U.S. Pat. No. 6,673,986.

As used herein, term "percent (%) identity" refers to the percentage of amino acid residues (or nucleic acid bases) of a candidate sequence, e.g., an isolated anti-Trop-2 antibody of the present disclosure, that are identical to the amino acid residues (or nucleic acid bases) of a reference sequence, after aligning the sequences and introducing gaps, if necessary, to achieve the maximum percent identity (i.e., gaps can be introduced in one or both of the candidate and reference sequences for optimal alignment and non-homologous sequences can be disregarded for comparisons). Alignment for determining percent identity can be achieved using BLAST 2.0 software with standard settings. Alignment can be performed to achieve maximal alignment over the full length of the sequences being compared. In some embodiments, the percent amino acid (or nucleic acid) sequence identity of a given candidate sequence to, with, or against a given reference sequence (which can alternatively be phrased as a given candidate sequence that has or comprises a certain percent amino acid (or nucleic acid) sequence identity to, with, or against a given reference sequence) is calculated as follows:

$$100 \times (\text{fraction of } A/B),$$

in which A is the number of amino acid residues (or nucleic acid bases) scored as identical in the alignment of the candidate sequence and the reference sequence, and B is the total number of amino acid residues (or nucleic acid bases) in the reference sequence. In some embodiments where the length of the candidate sequence does not equal to the length of the reference sequence, the percent amino acid (or nucleic acid) sequence identity of the candidate sequence to the reference sequence will not equal to the percent amino acid (or nucleic acid) sequence identity of the reference sequence to the candidate sequence.

In a particular embodiment, a reference sequence aligned for comparison with a candidate sequence may show that the candidate sequence exhibits from 50% to 100% identity across the full length of the candidate sequence or a selected portion of contiguous amino acid residues (or nucleic acid bases) of the candidate sequence. The length of the candidate sequence aligned for comparison is at least 30%, e.g., at least 40%, e.g., at least 50%, 60%, 70%, 80%, 90%, or 100% of the length of the reference sequence. When a position in the candidate sequence is occupied by the same amino acid residue (or nucleic acid base) as the corresponding position in the reference sequence, then the molecules are identical at that position.

Terms "antigen", "immunogen", "antibody target, "target analyte" and the like as used herein refer to a molecule, compound, or complex that is recognized by an antibody, i.e., can be specifically bound by the antibody. Those term can refer to any molecule that can be specifically recognized by an antibody, e.g., a polypeptide, polynucleotide, carbohydrate, lipid, chemical moiety, or combinations thereof (e.g., phosphorylated or glycosylated polypeptides, etc.). Those skilled will understand mat those term do not indicate that the molecule is immunogenic in every context, but simply indicate that it can be targeted by an antibody.

As used herein, term "isolated" refers to a state obtained from natural state by artificial means. If a certain "isolated" substance or component is present in nature, it is possible because its natural environment changes, or the substance is isolated from natural environment, or both. For example, a certain unisolated polynucleotide or polypeptide naturally exists in a certain living animal body, and the same polynucleotide or polypeptide with a high purity isolated from such a natural state is called isolated polynucleotide or polypeptide. Term "isolated" does not exclude mixed artificial or synthesized substance or other unpure substance that does not affect the activity of the isolated substance.

Term "host cell" refers to a cell into which a vector can be introduced, including but not limited to prokaryotic cells such as *Escherichia coli* cells, fungal cells such as yeast cells, insect cells such as *Drosophila melanogaster* (S2) cells or *Spodoptera frugiperda* (Sf9) cells, or animal cells such as fibroblasts, CHO cells, COS cells, NSO cells, HeLa cells, BHK cells, HEK293 cells or human cells, etc.

Term "KD" refers to the equilibrium dissociation constant (KD) of a specific antibody-antigen interaction, which is used to describe the binding affinity between the antibody and the antigen. The smaller the equilibrium dissociation constant, the closer the antibody-antigen binding, and the higher the affinity between the antibody and the antigen. In general, an antibody binds to an antigen at an equilibrium dissociation constant less than about $10^{-5}$ M, for example, less than about $10^{-6}$ M, $10^{-7}$ M, $10^{-8}$ M, $10^{-9}$ M or $10^{-10}$ M or less, for example, as determined by surface plasmon resonance (SPR) in a BIACORE instrument. For example, the affinity of an antibody with a cell is detected on a KINEXA 400 instrument using KINEXA method.

Term "Specific binding" means that an antibody reacts with one or more antigenic determinants of an antigen but does not react with other polypeptides, or it binds to other polypeptides with very low affinity (Kd>$10^{-6}$). The antibody include but is not limited to polyclonal, monoclonal, chimeric, dAb (domain antibody), single chain, Fab, Fab' and F(ab')$_2$ fragment, Fv, scFv and Fab expression library. A monoclonal antibody (mAb) is an antibody obtained from a monoclonal cell line, and the cell line is not limited to eukaryotic, prokaryotic or phage clonal cell lines. A monoclonal antibody or antigen-binding fragment thereof can be obtained by recombination using, for example, hybridoma technology, recombination technology, phage display technology, and synthesis techniques such as CDR grafting, or other known techniques.

Term "Trop-2" refers to TROP2, which belongs to the TACSTD family, and is a cell surface glycoprotein encoded and expressed by the TACSTD2 gene. It is also known as tumor-associated calcium signal transducer 2 (TACSTD2), epidermal glycoprotein 1 (EGP-1), gastrointestinal tumor associated antigen (GA733-1), and surface marker 1 (M1S1). Trop-2 is overexpressed in a variety of malignant tumors and is an oncogene related to the occurrence, invasion and metastasis of malignant tumors.

The Trop-2 gene is located on the short arm of chromosome 1. The specific location is 1p32.1. The full length of the gene is 9072 bp, no intron, only one exon. The similarity of mouse Trop-2 to human homologous gene sequence was 87.4%. The primary structure of the Trop-2 protein is a 36 kDa polypeptide consisting of 323 amino acids, a single transmembrane surface glycoprotein. Trop-2 is composed of hydrophobic precursor peptide (AA1-26), extracellular domain (AA27-274), one transmembrane domain (AA275-297) and one cytoplasmic tail (AA298-323). The N-terminus of the Trop-2 protein is the extracellular domain (ECD), which is linked to the intracellular short tail (IC) by a unidirectional transmembrane helix (TM), thereby being immobilized on the membrane. The cytoplasmic tail of Trop-22 contains a highly conserved phosphatidylinositol 4,5-bisphosphate (PIP2) binding sequence, suggesting that PIP2 plays an important role in signal transduction of Trop-2. In addition to the PIP2 binding motif, it also contains conserved tyrosine and serine phosphorylation sites. Mutation of the serine residue at position 303 abolished the ability of Trop-2 to stimulate tumor growth. Phosphorylation of this residue is the responsibility of protein kinase C (PKC).

Term "antibody-drug conjugate (ADC)" refers to a conjugate in which a biologically active small-molecule drug is linked to, via a chemical linker, a monoclonal antibody which is acted as a carrier for targeting transport of the small-molecule drug to target cells.

The antibody molecule in an ADC drug is usually a humanized monoclonal antibody, and its fragment crystallizable (Fc) region is modified to reduce antibody-dependent cell-mediated cytotoxicity (ADCC) and complement-dependent cytotoxicity (CDC), etc. Firstly, since the antibody molecule is a biological macromolecule, toxicity risks of a biological macromolecule in general exist for the antibody molecule, such as immunogenicity and immunotoxicity, as well as possibly ADCC, CDC and kidney basement membrane immune complex deposition in case of a monoclonal antibody. Secondly, in an ADC drug, the most important role of the antibody molecule is targeting, i.e. targeted delivering a small molecule compound to the antigen-antibody binding site. If the antibody is less selective or the antigen is present in normal tissue, the cytotoxic drug will be delivered into normal cells, resulting in targeting toxicity. Thirdly, in addition to targeting toxicity, shedding of small molecules in circulation may result in some degree of off-target toxicity. The Fc in the antibody molecule, if has an activity of binding to Fc receptors on immune cells such as FcγRs/FcRN, will readily bind immune cells, thereby causing killing of the immune cells. Finally, an ADC drug, as an exogenous biomacromolecule, may also be engulfed in circulation and enter cells via pinocytosis, resulting in cell death.

Linkers commonly used in ADC drugs mainly include hydrazone, disulfide and peptide bonds. Hydrazone bonds are relatively unstable linkages that undergo hydrolysis under acidic conditions. A hydrazone linker is used in Mylotarg® and is considered by researchers to be a significant cause for the failure of Mylotarg®. Disulfide bonds are hydrolyzed by intracellular high concentration of glutathione, and are less easily broken up extracellularly. Peptide bonds are the tightest linkages and are cleaved only by lysosomal proteolytic enzymes. The stability of the linker directly affects the unintended dissociation of the cytotoxic drug, and the cleavage results in exposure of the small molecule cytotoxic drug in vivo, i.e., off-target toxicity.

Cytotoxic drugs commonly used in ADC drugs are chemotherapy drugs conventionally used in clinic, and determine the main toxic effect profiles of the ADC drugs. Because those drugs have been widely used clinically, they generally have clear toxicity characteristics. The risk of toxicity can be well ascertained depending on the type of the drugs, e.g., tubulin polymerization inhibitors or DNA damaging agents/DNA replication inhibitors. Among the drugs, the tubulin inhibitor comprises dolastatin and auristatin derivatives thereof (MMAE, MMAF, and MMAD), maytansine and maytansinoid derivatives (DM1, DM2, DM3, and DM4), paclitaxel and paclitaxel derivatives (docetaxel), docetaxel, vincristine and the like, and the DNA damaging agent/DNA replication inhibitor comprises irinotecan or its active metabolite SN-38, etc.

"Optional", "optionally", "any", or "any one" means that the following event or situation may but not necessarily occur, and the description includes the instances in which the event or situation does or does not occur. For example, "optionally contains 1 antibody heavy chain variable region" means the antibody heavy chain variable region with a specific sequence may be, but not necessarily be, present.

Term "pharmaceutical composition" refers to a mixture containing one or more compounds of the present disclosure or a physiologically/pharmaceutically acceptable salt or prodrug thereof together with other chemical components, as well as other components such as a physiologically/pharmaceutically acceptable carrier and excipient. The pharmaceutical composition is used to facilitate administration to an organism, and facilitate absorption of the active ingredient to exert biological activities. A therapeutic composition should generally be sterile and stable under conditions of manufacture and storage. The composition can be formulated as a solution, a microemulsion, a dispersion, a liposome or other ordered structure suitable for a high antibody concentration. A sterile injectable solution can be prepared by incorporating the active compound (i.e., the antibody or antibody portion) in a required amount in an appropriate solvent with one ingredient or a combination of ingredients as listed above, and as required followed by being filtered for sterilization.

The method, composition, and combination therapy according to the present disclosure can be combined with other active agents or therapeutic methods. The method includes the administration of the anti-Trop-2 antibody molecule of the present disclosure to a subject in an amount effective for treatment or prevention of a disease (e.g., a cancer), optionally, in combination with one or more inhibitors selected from PD-1, PD-L1, PD-L2, LAG-3, CTLA-4, or Tim-3 antibody (immunotherapy) or other tumor therapeutic antibodies, such as Her-2, EGFR, VEGF, VEGFR antibodies, etc., as well as ADC (antibody drug conjugate, such as T-DM1), bispecific antibody, chemotherapy drug, etc. The method also includes the administration of additional active agents or all can be administered in such amount or dose that is higher, lower, or equal to the amount or dose of each active agent used alone (e.g., as a monotherapy). The administered amount or dose of the additional active agents or all of them is lower (e.g., at least 20%, at least 30%, at least 40%, or at least 50%) than the amount or dose of each active agent used alone (e.g., as a monotherapy).

The present disclosure provides novel antibodies against human Trop-2, which have good biological activities: the antibodies provided by the present disclosure (including chimeric antibodies and humanized antibodies) could effectively bind both recombinant Trop-2 protein or the Trop-2 antigen expressed on the surface of cells, similar to control antibody Sacituzumab. Meanwhile, the antibodies provided by the present disclosure have high affinity to human Trop-2: compared with control antibody Sacituzumab, the humanized antibodies of the disclosure exhibited even higher binding ability specific for human Trop-2 protein and higher affinity than Sacituzumab. Therefore, the antibodies of the present disclosure have good therapeutic effects.

Experiments proved that the antibodies of the present disclosure had good internalization ability: the humanized antibodies had an internalization rate similar to that of control antibody Sacituzumab, and when prepared into ADCs, their internalization ability was significantly enhanced. Thus, the antibodies of the present disclosure have potential for developing ADC drugs. The anti-Trop-2 antibodies of the present disclosure may also have a synergistic effect with other antibodies. For example, the antibodies of the present disclosure could be used in combination with anti-CD47 antibody to further promote phagocytosis of tumor cells by macrophages.

In addition, the antibodies of the present disclosure have been demonstrated to have good in vivo therapeutic efficacy. ADCs were prepared with the antibodies of the present disclosure, and the anti-Trop2-ADCs had dose-dependent inhibitory effect on tumor growth, and with a high dosage (10 mg/kg), the therapeutic effect of each ADC was equivalent to that of control antibody Sacituzumab; and no obvious toxic effect of the small molecule SN38 in the ADCs was observed, and the body weight of animals in each experiment group steadily increased, without obvious difference from controls.

BRIEF DESCRIPTION OF THE DRAWINGS

Embodiments of the present invention are described in detail below with reference to the attached figures, in which:

FIG. 6 shows the detection results via ELISA of species-specific binding of anti-human Trop-2 antibodies to Trop-2, in which panel 6A: h23-12; panel 6B: h4-3; panel 6C: Sacituzumab.

FIG. 7 shows the analysis results of affinity of anti-human Trop-2 antibodies for recombinant human Trop-2 extracellular domain, in which panel 7A: Sacituzumab; panel 7B: h23-12; panel 7C: h4-3.

FIG. 8 shows the observations of internalization of anti-Trop-2 humanized antibodies after binding to Trop-2 on the surface of N87 cells.

FIG. 12 shows the curves of changes in tumor volume of BALB/c nu mice bearing tumors in a mouse model of N87 gastric cancer, in which panel 12A: after the administration of ch4-3-SN38; panel 12B: after the administration of h23-12-SN38; panel 12C: after the administration of isotype control antibody; panel 12D: after the high dosage administration of ch4-3-SN38 and h23-12-SN38.

DETAILED DESCRIPTION OF PREFERRED EMBODIMENTS

Figure 1:
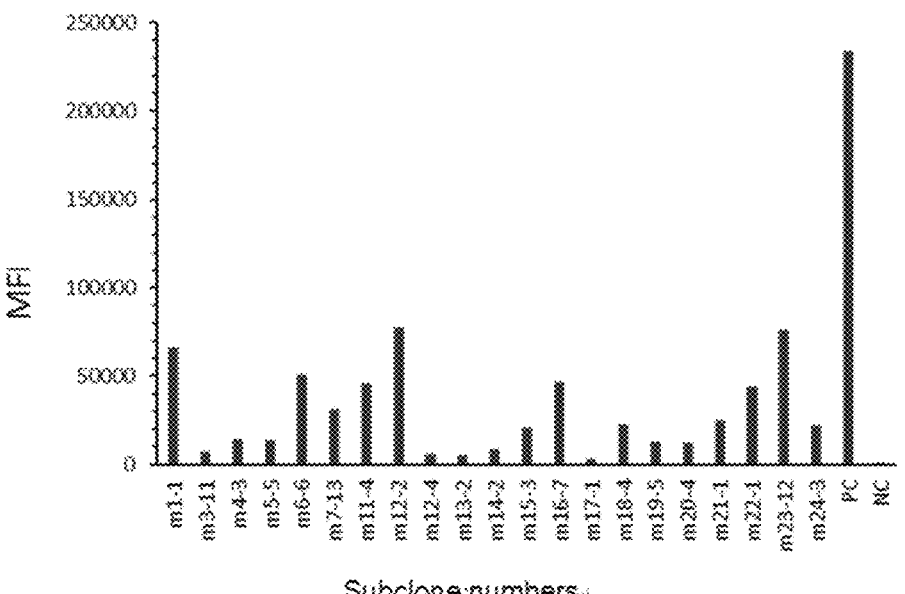
FIG. 1 shows the screening results of binding of positive hybridoma supernatants to Trop-2 on the surface of CHO cells.

The present invention is illustrated below with reference to specific examples. It will be understood by those skilled in the art that these examples are merely illustrative of the present invention and do not limit the scope of the present invention in any way.

Experimental procedures in the following examples are all conventional ones, unless otherwise specified. Raw materials and reagents used in the following examples are all commercially available products, unless otherwise specified.

Example 1 Preparation of Hybridoma Cells Secreting Anti-Human Trop-2 Antibodies Immunization: Balb/c mice were immunized with recombinant human Trop-2 protein (ACCESSION NO.: NP_002344.2, AA 1-274), and serum titers were detected via ELISA in 96-well ELISA plates coated with recombinant human Trop-2-his protein (ACCESSION NO.: NP 002344.2, AA 1-274). Mice with serum titers meeting the requirements for cell fusion were used for cell fusion of the next step.

Cell fusion and hybridoma preparation: mice with required titers were selected to perform rush immunization, and spleens were collected aseptically from the mice 3 days later. B lymphocyte suspensions were prepared and mixed with SP2/0 myeloma cells at a ratio of 4:1, to make the cells fuse in the presence of PEG. The fused cells were resuspended in HAT medium, inoculated into 96-well cell culture plates, and cultured in an incubator at 37° C., 5% $CO_2$.

Example 2 Screening of Positive Hybridoma Cell Lines Secreting Anti-Human Trop-2 Antibodies 1. Screening of Binding of Positive Hybridomas 10-14 days after fusion, ELISA plates were coated with recombinant human Trop-2-his protein (ACCESSION NO.: NP_002344.2, AA 1-274) (20 ng/ml) overnight at 4° C.; washed with PBS 3 times, the plates were blocked with 4% skimmed milk powder-PBS at room temperature for 1 h; then the plates were washed with PBS 3 times, and culture supernatants of hybridoma clones were added into the plates and incubated at room temperature for 1 h. Controls as follows were set: (1) Positive Control (PC): serum from mice post immunization (1:1000 diluted in PBS); (2) Negative Control (NC): fusion well without cell growth. The plates were washed with PBST (0.05% Tween-PBS) 3 times, and washed with PBS 2 times, and then HRP-goat anti-mouse IgG (Fc gamma) was added into the plates for incubation at 37° C. for 0.5 h. Afterwards, the plates were washed with PBST (0.05% Tween 20-PBS) 3 times again, and TMB substrate was added for color development in dark for 15-30 min. Then ELISA stop solution was added to stop reaction; and A450 values were read using a microplate reader.

The clones were ordered from highest reading to lowest reading, and the top 95 clones with high readings were selected for double-checking via ELISA, and a pool of 25 positive cells secreting antibodies was subcloned by limiting dilution. 10 days after plating, culture supernatants of monoclonal cells were selected for further screening for positive clones via ELISA which was performed as above described. The clones were ordered from highest reading to lowest reading again, and the top 21 clones with high readings, i.e., m1-1, m3-11, m4-3, m5-5, m6-6, m7-13, m11-4, m12-2, m12-4, m13-2, m14-2, m15-3, m16-7, m17-1, m18-4, m19-5, m20-4, m21-1, m22-1, m23-12 and m24-3, were selected for the next step screening of binding via FACS.
2. Screening of Binding of Positive Hybridomas to Trop-2 on the Surface of CHO Cells The reading frame of Trop-2 gene was cloned from a vector containing Trop-2 cDNA (Cat.: HG10428-M, Beijing Yiqiao Shenzhou Science and Technology Co., Ltd.) by PCR, and cloned into a stable expression vector containing Glutamine Synthetase (GS) gene by enzyme digestion for screening. Suspension cultured CHO-K1 cells were electrotransfected (Nucleofector IIb, Lonza) and the transfected cells were transferred into CD CHO AGT™ medium (Cat.: 12490-025, Gibco) containing 50 μM MSX (Cat.: M5379, Sigma), and inoculated in 96-well cell culture plates. After being allowed to stand at 37° C., 5% $CO_2$ for 2-3 weeks, 22 wells containing cells were obtained through prescreening with MSX pressure screening, and the cells were expanded in 24-well cell culture plates, and finally the clone No. 1-T-21 (CHO/Trop-2 cells) was selected via flow cytometry (FACS) analysis. Scale-up culture of the clone was performed and the cells were cryopreserved and used for FACS detection.

According to the above ELISA results, supernatants of the 21 hybridoma clones selected were diluted 100 times and incubated with suspensions of the constructed CHO cells (CHO/Trop-2 cells) at 37° C. for 30 min. Controls as follows were set: (1) Positive Control (PC): Sacituzumab, a version having murine IgG constant region, 1 g/ml; (2) Negative Control (NC): irrelevant murine antibody, 1 μg/ml. The cells were washed 3 times with PBS, and 1:200 dilution of goat anti-mouse IgG-FITC (Cat.: F9006, Sigma) was added into the cells which then were incubated for 30 min. Then the cells were washed 3 times with PBS, and the Mean Fluorescence Intensity (MFI) of the cells was measured by a flow cytometer (model no. B49007AD, SNAW31211, BECKMAN COULTER) to verify whether the antibody secreted by each hybridoma could bind Trop-2 on the surface of CHO cells. The results are shown in FIG. 1.

Figure 2:
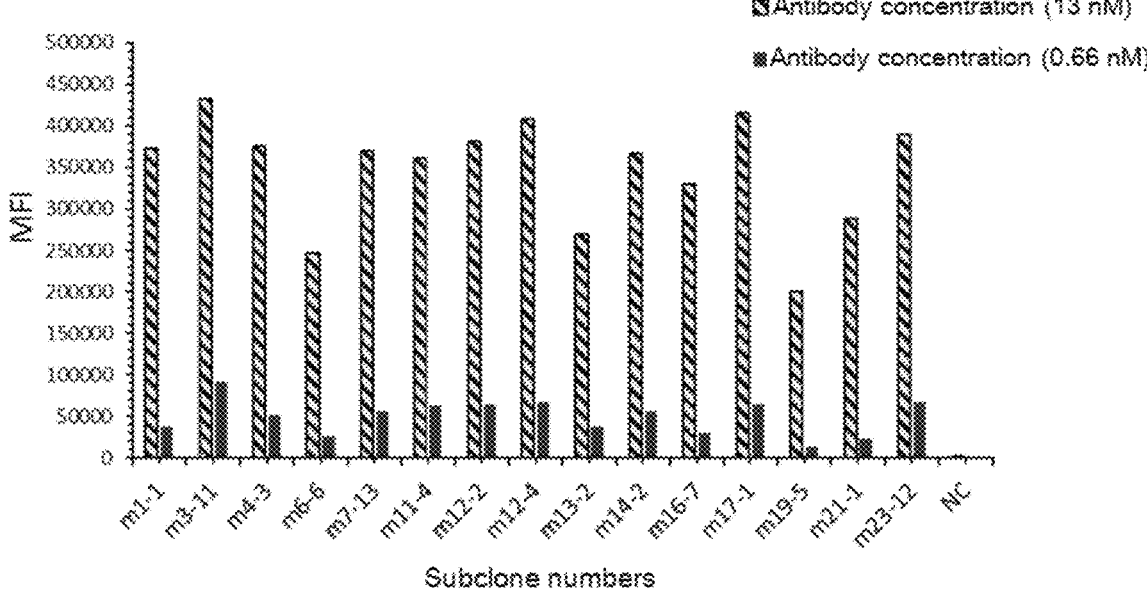
FIG. 2 shows the screening results of binding of positive hybridoma supernatants to Trop-2 on the surface of CHO cells.
Figure 3:
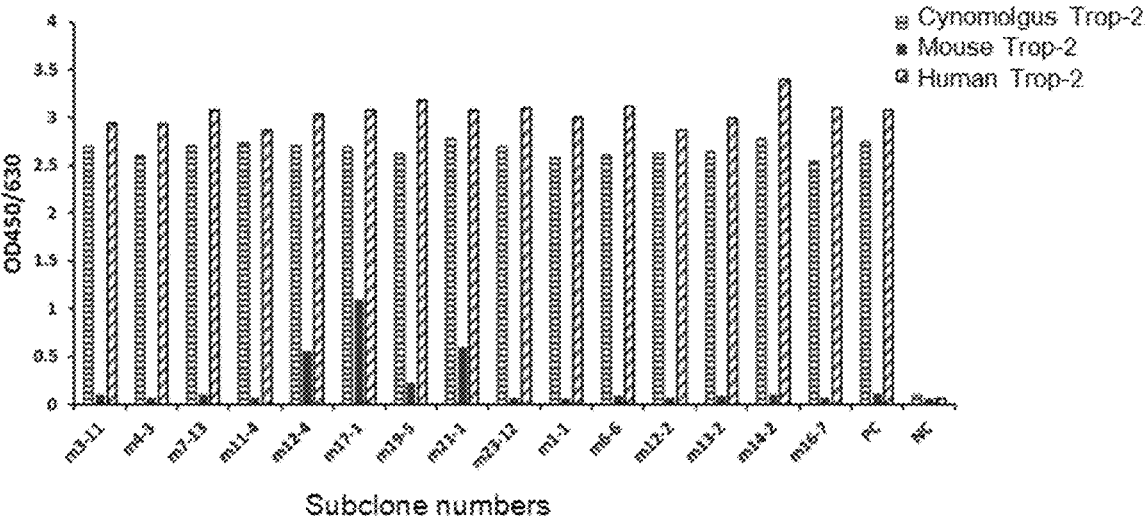
FIG. 3 shows the detection results via ELISA of cross-reactivity of positive hybridoma supernatants with recombinant Trop-2 proteins of different species.

Based on FIG. 1 and states of the cells, clones ml-1, m3-11, m4-3, m6-6, m7-13, m11-4, m12-2, m12-4, m13-2, m14-2, m16-7, m17-1, m19-5, m21-1, and m23-12 were selected, supernatants of those hybridomas were purified through ProA affinity chromatography column, and binding of the purified murine antibodies was confirmed again. The antibodies were diluted to 13 nM and 0.66 nM respectively, and then incubated with a suspension of CHO cells recombinantly expressing human Trop-2 (CHO/Trop-2 cells) for 30 min at 37° C. Controls as follows were set: (1) Positive Control (PC): Sacituzumab, a version having murine IgG constant region, 1 μg/ml; (2) Negative Control (NC): irrelevant murine antibody, 1 μg/ml. The cells were washed 3 times with PBS, and 1:200 dilution of goat anti-mouse IgG-FITC (Cat.: F9006, Sigma) was added into the cells which then were incubated for 30 min. Then, the cells were washed 3 times with PBS, and the Mean Fluorescence Intensity (MFI) of the cells was measured by a flow cytometer (model no. B49007AD, SNAW31211, BECKMAN COULTER) to verify whether the antibody secreted by each hybridoma could bind Trop-2 on the surface of CHO cells. As shown in FIG. 2, all the antibodies from the supernatants of 15 clones bound to Trop-2 on the surface of CHO cells well. Clones m3-11, m4-3, m11-4, m17-1, and m23-12 were selected as candidate clones for further screening.
3. Screening Via ELISA of Cross-Reactivity of Positive Hybridoma Clones Plates were coated with recombinant human Trop-2-his protein (ACCESSION NO.: NP_002344.2, AA 1-274), recombinant cynomolgus Trop-2-his protein (ACCESSION NO.: UniProtKB-A0A2K5UE71, AA 1-272), and recombinant mouse Trop-2-his protein (Cat.: 50922-M08H, Beijing Yiqiao Shenzhou Science and Technology Co., Ltd.) respectively overnight at 4° C., each protein having a coating concentration of 0.2, and 1 μg/ml respectively. Washed with PBS 3 times, the plates were blocked with the added 5% BSA PBS at 37° C. for 60 min, and then washed 3 times with PBST. The 15 purified murine antibodies were diluted to 1

μg/ml with PBS. Controls as follows were set: (1) Positive Control (PC): Sacituzumab (WHO Drug Information (Vol. 31, No. 1, 2017), SEQ ID NO: 39 and SEQ ID NO: 40), a version having murine IgG constant region, 1 μg/ml; (2) Negative Control (NC): an antibody from an irrelevant hybridoma, 1 μg/ml; (3) blank control: PBS. After incubation at 37° C. for 60 min, the plates were washed 4 times with PBST. 1:5000 dilution of HRP-goat anti-mouse IgG (Fc gamma) (Cat: 115-035-071; Jackson ImmunoResearch) was added into the plates for incubation at 37° C. for 30 min. Afterwards, the plates were washed with PBST 4 times, and TMB substrate was added for color development at 37° C. for 10 min. Then 2M HCl was added to stop reaction; and absorbances at 450 nm and at 630 nm (as reference wavelength) were read, and A450 nm-630 nm values of the wells in the plates were recorded. Except that the antibodies from clones m12-4, m17-1, m19-5, and m21-1 exhibited cross-reactivity with mouse Trop-2, other antibodies exhibited no cross-reactivity with mouse Trop-2; and all the antibodies of the hybridomas could specifically bind recombinant human and cynomolgus Trop-2 (FIG. 3).

Example 3 Sequencing of Murine Anti-Human
Trop-2 Antibodies

After expanded culture of hybridomas m3-11, m4-3, m11-4, m17-1, and m23-12 secreting anti-human Trop-2 antibodies, subtypes of the antibodies were detected using Mouse Monoclonal Antibody IgG Subclass Test Card (Cat.: A12403, VicNovo) and Mouse Monoclonal Antibody Light/ Heavy Chain Test Card (Cat.: A12401, VicNovo) according to Reagent Protocol. Subtypes were identified as: the antibodies were IgG1 for heavy chains, and were Kappa for light chains. The results provided a basis for gene cloning of the antibodies from m3-11, m4-3, m11-4, m17-1, and m23-12.

Total RNA was extracted from the hybridoma cells m3-11, m4-3, m11-4, m17-1, and m23-12 using TRIzol™ reagent (a phenol-guanidine isothiocyanate based solution; Cat: 15596026, Invitrogen) following the steps described in the instructions. The total RNA of the hybridoma cells was reversely transcribed into cDNA using M-MuLV reverse transcriptase (Cat: M0253S, NEB). The sequences of light chain variable region IgVL (κ) and heavy chain variable region VH of the antibodies were amplified using degenerate primers (see Zhiwei DONG and Yan Wang, Antibody Engineering (2nd Edition), Peking University Medical Press, 2001, pages 313-314) and Phusion™ High-Fidelity DNA Polymerase (Cat: E0553L, NEB). PCR products were purified with gel extraction kit (Cat: AP-GX-250, Axygen) and the purified PCR products were ligated to T vector following the instructions of a T vector cloning Kit (Cat: ZC205, Beijing Zoman Biotechnology Co., Ltd.) and then the obtained vectors were transformed into competent E. coli cells for amplification. The plasmids were then extracted for DNA sequencing to obtain variable region sequences of the monoclonal antibodies.

Sequencing Results Showed:

The nucleotide sequence (DNA) of the heavy chain variable region of the murine antibody from clone m3-11 is as shown in SEQ ID NO: 41, and the amino acid sequence of the heavy chain variable region of the murine antibody from clone m3-11 deduced from the nucleotide sequence is as shown in SEQ ID NO: 1; and the nucleotide sequence (DNA) of the light chain variable region of the murine antibody from clone m3-11 is as shown in SEQ ID NO: 42, and the amino acid sequence of the light chain variable region of the murine antibody from clone m3-11 deduced from the nucleotide sequence is as shown in SEQ ID NO: 18.

SEQ ID NO: 1:
QVQLQQPGAELVKPGSSVKLSCKASGYTFT<u>SYWMY</u>WVKQRPGQGLEWIG

<u>EINPSNGRTNYNEKFK</u>SKATLTVDKSSSTAYMQFSSLTSEDSAVYYCTR

<u>EGHNYDGSLGAMDH</u>WGQGTSVTVSS

SEQ ID NO: 18:
DVVVTQTPLSLPVSFGDQVSISC<u>RSSQSLTNSYGNTFLS</u>WYLHKPGQSP

QLLL<u>YGISNRF</u>SGVPDRFSGSGSGTDFTLKINTIKPEDLGMYYC

<u>FQSTHQPYT</u>FGGGTKLEIK

The nucleotide sequence (DNA) of the heavy chain variable region of the murine antibody from clone m4-3 is as shown in SEQ ID NO: 43, and the amino acid sequence of the heavy chain variable region of the murine antibody from clone m4-3 deduced from the nucleotide sequence is as shown in SEQ ID NO: 2; and the nucleotide sequence (DNA) of the light chain variable region of the murine antibody from clone m4-3 is as shown in SEQ ID NO: 44, and the amino acid sequence of the light chain variable region of the murine antibody from clone m4-3 deduced from the nucleotide sequence is as shown in SEQ ID NO: 19.

SEQ ID NO: 2:
QVQLQQSGPELVKPGASVKMSCKASGFTFT<u>DYVIG</u>WVKQRTGQGLEWIG

<u>EIYLGSGTIYYTEKFKG</u>KATLTADTSSNTAYMQLSSLTSEDSAVYFCAR

<u>GSIFPFDY</u>WGQGTTLTVSS

SEQ ID NO: 19:
QIVLTQSPAIMSASPGEKVTMTC<u>SASSSVSYMY</u>WYQQKPGSSPRLLIY

<u>DTSTLAS</u>GVPVRFSGSGSGTSYSLTISRMEAEDAATYYC

<u>QQWSSYPYT</u>FGGGTKLEIK

The nucleotide sequence (DNA) of the heavy chain variable region of the murine antibody from clone m11-4 is as shown in SEQ ID NO: 47, and the amino acid sequence of the heavy chain variable region of the murine antibody from clone m11-4 deduced from the nucleotide sequence is as shown in SEQ ID NO: 5; and the nucleotide sequence (DNA) of the light chain variable region of the murine antibody from clone m11-4 is as shown in SEQ ID NO: 48, and the amino acid sequence of the light chain variable region of the murine antibody from clone m11-4 deduced from the nucleotide sequence is as shown in SEQ ID NO: 24.

SEQ ID NO: 5:
QVQLQQPGAELVRPGASVNLSCKASGYTFT<u>SYWIN</u>WVKQRPGQGLEWIG

<u>NIYPSNSYTNYNQKFK</u>DTATLTVDKSSSTAYMQLSSPTSEDSAVYFCSS

<u>YRSDGFAY</u>WGQGTLVTVSA

SEQ ID NO: 24:
DILLTQSPAILSVSPGEKVSFSC<u>RASQNIGTSIH</u>WYQQRINGSPRLLIE

<u>FASESIS</u>GIPSRFSGSGSGTDFTLTINSVESEDIADYYC

<u>QQSNSWPFT</u>FGGGTKLEIK

The nucleotide sequence (DNA) of the heavy chain variable region of the murine antibody from clone m17-1 is as shown in SEQ ID NO: 51, and the amino acid sequence of the heavy chain variable region of the murine antibody from clone m17-1 deduced from the nucleotide sequence is as shown in SEQ ID NO: 11; and the nucleotide sequence (DNA) of the light chain variable region of the murine antibody from clone m17-1 is as shown in SEQ ID NO: 52, and the amino acid sequence of the light chain variable region of the murine antibody from clone m17-1 deduced from the nucleotide sequence is as shown in SEQ ID NO: 30.

```
SEQ ID NO: 11:
EVKLVESGGVLVKPGGSLKLSCAASGFTFSDSAMSWVRQTPEKRLEWVA

SISRGDDTYYPDSVKGRITISRDFARNILYLQMTSLRSEDTAMYYCTR

DRFGFAYWGQGTLVTVSA

SEQ ID NO: 30:
DIVMTQSPLTLSVTIGQPASISCKSGQSLLDSDGKTYFNWLLQRPGQSP

KRLIYLVSMLDSGVPDRFTGSGSGTDFTLKISRVETEDLGVYYC

WQGTHFPFTFGSGTKLEIK
```

The nucleotide sequence (DNA) of the heavy chain variable region of the murine antibody from clone m23-12 is as shown in SEQ ID NO: 53, and the amino acid sequence of the heavy chain variable region of the murine antibody from clone m23-12 deduced from the nucleotide sequence is as shown in SEQ ID NO: 12; and the nucleotide sequence (DNA) of the light chain variable region of the murine antibody from clone m23-12 is as shown in SEQ ID NO: 54, and the amino acid sequence of the light chain variable region of the murine antibody from clone m23-12 deduced from the nucleotide sequence is as shown in SEQ ID NO: 31.

```
SEQ ID NO: 12:
QVQLQQPGAELVKPGASVKLSCKADGYIFTSYWMHWVKQRPGQGLEWIG

EITPSDNYTSYNQKFKGKATLTVDKSSSTAYMQLSSLTSEDSAVYYCTR

GHGNYVSFDYWGQGTTLTVSS

SEQ ID NO: 31:
DIQMTQITSSLSASLGDRVTITCRASQDISNYLNWYQQKPDGTVKLLIY

YTSRLHSGVPSRFSGSGSGTDYSLTISNLEQEDIATYFC

QQGYTLPPYTFGGGTKLEIK
```

Example 4 Preparation of Anti-Human Trop-2 Chimeric Antibodies and Control Antibody The light and heavy chain sequences of control antibody (Sacituzumab) were fully synthesized, and cloned into a eukaryotic transient-expression vector respectively to obtain expression plasmids expressing the light chain and heavy chain of the control antibody. The expression plasmids were transformed into E. coli cells for amplification, and a large number of plasmids containing the light chain and heavy chain of the control antibody respectively were obtained through plasmid recovery. The plasmids containing the light chain and heavy chain of the control antibody were in turn transfected into HEK293 cells respectively using 293fectin (Cat.: 12347019, Gibco) transfection reagent following the manufacturer's instructions for recombinant expression. 5-6 days after cell transfection, culture supernatant was taken and purified through ProA affinity chromatography column to obtain the control antibody. The amino acid sequences of the control antibody Sacituzumab were derived from WHO Drug Information (Vol. 31, No. 1, 2017), and the amino acid sequence of the heavy chain is as shown in SEQ ID NO: 39, and the amino acid sequence of the light chain is as shown in SEQ ID NO: 40.

The light chain variable region and heavy chain variable region genes of the murine antibodies 3-11, 4-3, 11-4, 17-1 and 23-12 obtained from the clones as above, with cleavage sites of restriction enzymes introduced by PCR, were respectively cloned into the upstream of gene encoding human-kappa light chain constant region and the upstream of gene encoding human IgG1 heavy chain constant region carried in eukaryotic transient-expression vectors. The obtained expression plasmids expressing human-murine chimeric light chain (pKN019-ch3-11L, pKN019-ch4-3L, pKN019-ch11-4L, pKN019-ch17-1L, pKN019-ch23-12L) and expression plasmids expressing human-murine chimeric heavy chain (pKN 041-ch3-11H, pKN019-ch4-3H, pKN019-ch11-4H, pKN019-ch17-1H, pKN019-ch23-12H) were transformed into E. coli cells for amplification, and a large number of plasmids containing human-murine chimeric light chain and heavy chain respectively were obtained through plasmid recovery. The plasmids containing the light chains and heavy chains of chimeric antibodies ch3-11, ch4-3, ch11-4, ch17-1 and ch23-12 were in turn transfected into HEK293 cells respectively using 293fectin (Cat.: 12347019, Gibco) transfection reagent following the manufacturer's instructions for recombinant expression. 5-6 days after cell transfection, culture supernatants were taken and purified through ProA affinity chromatography columns to obtain chimeric antibodies ch3-11, ch4-3, ch11-4, ch17-1 and ch23-12.

Example 5 Detection Via ELISA of Binding Activity of Anti-Human Trop-2 Chimeric Antibodies to Recombinant Trop-2 Protein Plates were coated with recombinant human Trop-2-his protein (ACCESSION NO.: NP_002344.2, AA 1-274) at a concentration of 0.2 ug/ml overnight at 4° C. and then blocked with 5% BSA for 60 min in a constant temperature incubator at 37° C. Chimeric antibodies ch3-11, ch4-3, ch17-1, ch11-4, and ch23-12 and control antibody Sacituzumab (serial dilutions of 8 concentrations in total obtained through 3-fold serially diluting a solution with an initial concentration of 2 µg/ml) were added into the plates which were then incubated in a constant temperature incubator at 37° C. for 60 min. The plates were washed with PBST 4 times, and 1:5000 dilution of HRP-anti-human Fc (Cat.: 109-035-098, Jackson ImmunoResearch) was added into the plates for reaction for 45 min. TMB (Cat.: ME142, GalaxyBio, Beijing) substrate was added for color development for 15 min, and then 2M HCl was added to stop reaction. Absorbances at 450 nm and at 630 nm (as reference wavelength) were read, and A450 nm-630 nm values of the wells in the plates were recorded.

Figure 4:
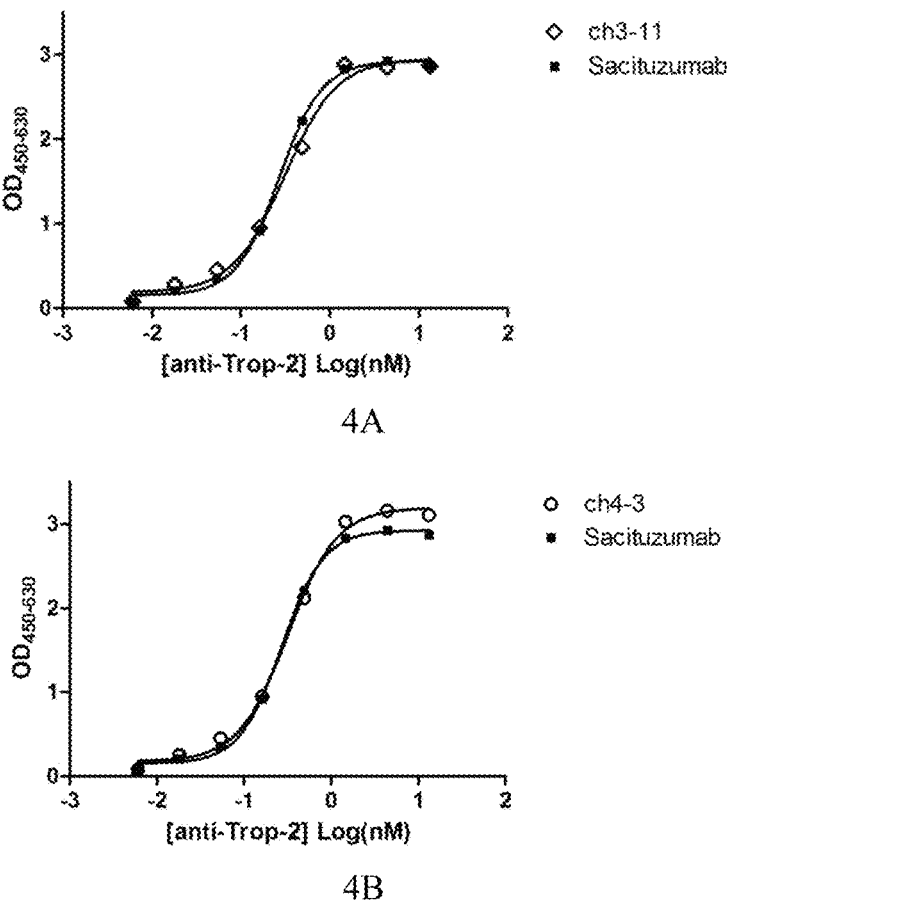
FIG. 4 shows the detection results via ELISA of binding activity of anti-human Trop-2 chimeric antibodies to recombinant Trop-2 protein, in which panel 4A: ch3-11; panel 4B: ch4-3; panel 4C: ch23-12; panel 4D: ch11-4; panel 4E: ch17-1.

The binding ability of each of ch3-11, ch4-3, ch17-1, ch11-4, and ch23-12 and control antibody Saituzumab to recombinant human Trop-2 protein was determined by ELISA, and the half maximal effective concentration (EC50) values about the binding of the antibodies were 0.3147 nM, 0.3195 nM, 0.3278 nM, 0.2366 nM, 0.4581 nM and 0.271 nM, respectively (FIG. 4), which were roughly equivalent. The results showed that chimeric antibodies ch3-11, ch4-3, ch17-1, ch11-4 and ch23-12 had high affinity to recombinant human Trop-2 protein, and the sequences of the murine antibodies 3-11, 4-3, 11-4, 17-1 and 23-12 were correctly cloned.

Example 6 Detection Via FACS of Binding
Activity of Anti-Human Trop-2 Chimeric
Antibodies to Recombinant Human Trop-2 Protein
on the Surface of CHO Cells Suspensions of CHO cells recombinantly expressing human Trop-2 (CHO/Trop-2 cells) were incubated with chimeric antibodies ch3-11, ch4-3, ch17-1, ch11-4, and ch23-12 (dilutions at concentrations of 30 µg/ml and 10 g/ml, and serial dilutions of 9 concentrations obtained through 3-fold serially diluting a solution with an initial concentration of 5 µg/ml, 11 concentrations in total) for 30 min at 37° C. Controls as follows were set: (1) Positive Control (PC): control antibody Sacituzumab; (2) Negative Control (NC): IgG1 isotype control antibody NC-IgG1. The cells were washed 3 times with PBS, and 1:100 dilution of goat anti-human IgG-FITC (Cat.: F9512, Sigma) was added into the cell which then were incubated for 30 min. Then the cells were washed 3 times with PBS again, and the Mean Fluorescence Intensity (MFI) of the cells was measured by a flow cytometer (model B49007AD, SNAW31211, BECK-MAN COULTER) to detect binding ability of the chimeric antibodies to human Trop-2 on the surface of CHO cells.

Figure 5:
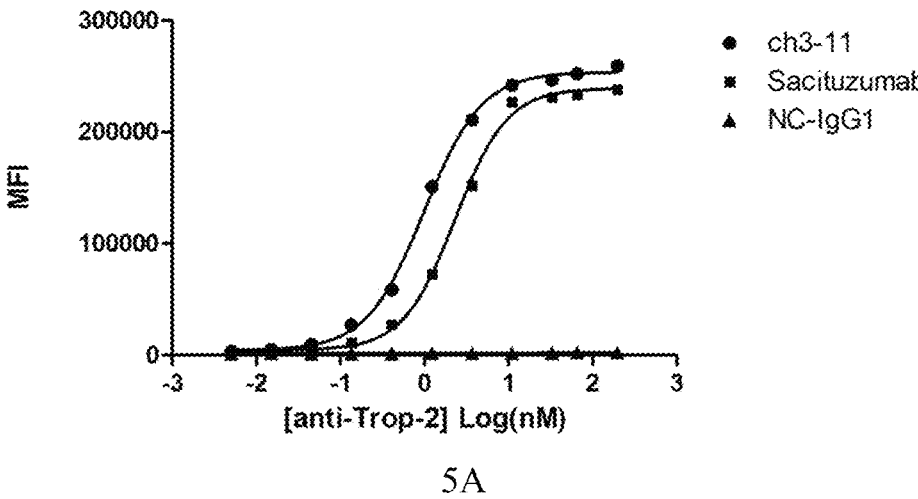
FIG. 5 shows the detection results via FACS of binding activity of anti-human Trop-2 chimeric antibodies to recombinant Trop-2 protein on the surface of cells, in which panel 5A: ch3-11; panel 5B: ch23-12; panel 5C: ch11-4; panel 5D: ch4-3; panel 5E: ch17-1.
Figure 5:
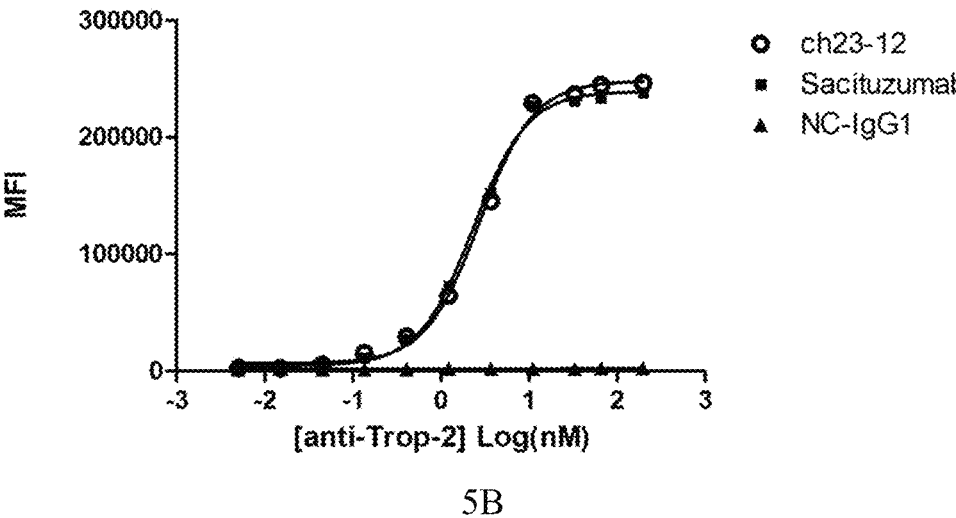
Figure 5:
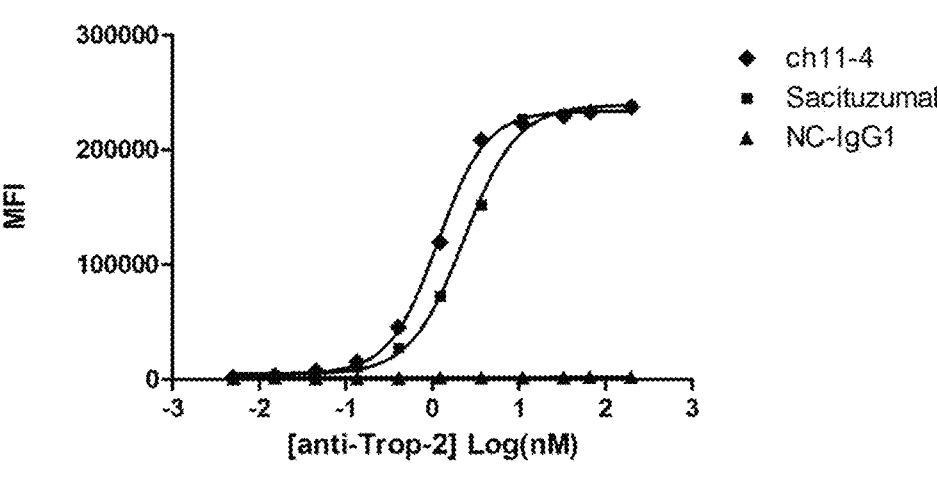
Figure 9:
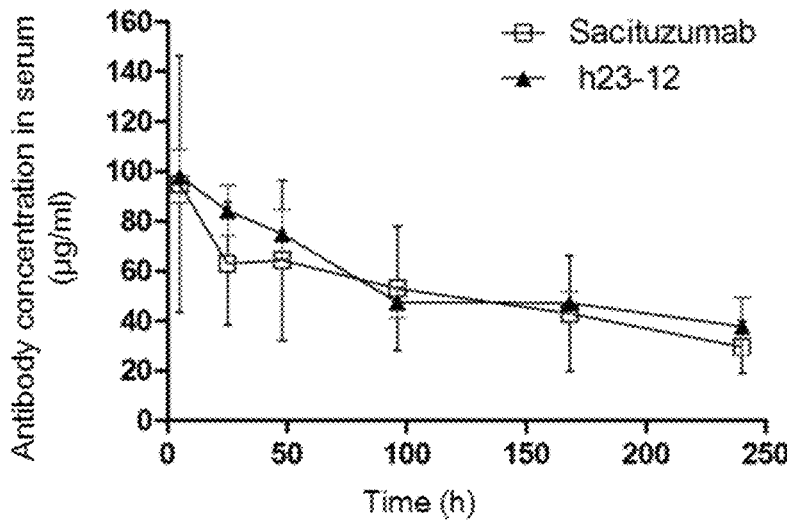
FIG. 9 shows the drug concentration versus time curves after single doses of anti-Trop-2 humanized antibodies in nude mice (detected with Trop-2), in which panel 9A: h23-12; panel 9B: h4-3.
Figure 9:
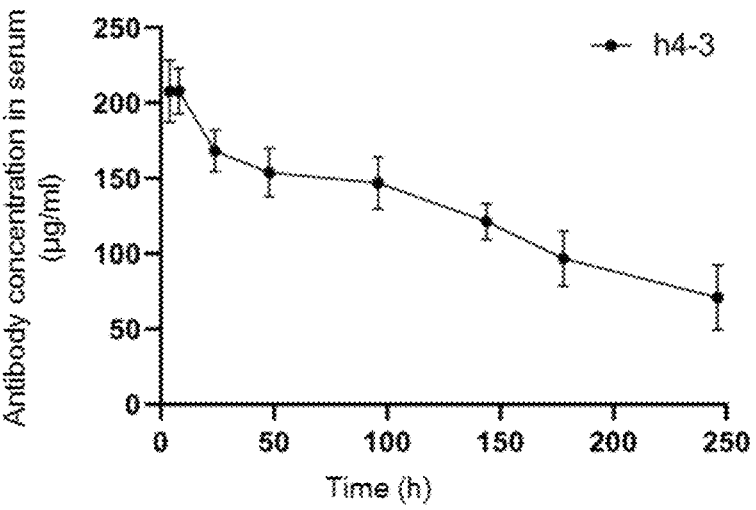

The binding ability of each of ch3-11, ch4-3, ch17-1, ch11-4, and ch23-12 and control antibody Sacituzumab to recombinant human Trop-2 protein on the surface of CHO cells was determined by FACS, and the half maximal effective concentration (EC50) values about binding of the antibodies were 0.993 nM, 3.326 nM, 2.918 nM, 1.154 nM, 2.748 nM, and 2.316 nM, respectively (FIG. 5).Compared with control antibody Sacituzumab, ch3-11 and ch11-4 had a better binding activity, and ch4-3, ch17-1 and ch23-12 had similar binding activity. The results showed that anti-human Trop-2 chimeric antibodies ch3-11, ch4-3, ch17-1, ch11-4, and ch23-12 could effectively bind recombinant human Trop-2 protein on the surface of CHO cells.

Example 7 Internalization Activity of Anti-Human
Trop-2 Chimeric Antibodies to Trop-2 on the
Surface of Cells BxPC-3 human pancreatic cancer cells were added in an amount of 5×10⁵ cell/tube into tubes containing chimeric antibodies ch3-11, ch4-3, ch11-4, ch23-12, and positive control antibody Sacituzumab respectively, and each of the antibodies was diluted to 10 µg/ml. Four groups were set for each antibody (experiment groups incubated for 1 h, 3 h, and 5 h respectively and control group) and each group included two tubes. The experimental groups were placed into an electric heating constant temperature incubator at 37° C., incubated for 1 h, 3 h, and 5 h respectively, and then placed on ice; and the control group was incubated always on ice as a negative control. When the incubation of all samples was completed, centrifugation was performed at 1,500 rpm at 4° C. for 3 min, and the supernatants were discarded. Cell pellets were washed with ice-cold PBS once, a secondary antibody, anti-human IgG (Fc-specific)-FITC antibody (Cat.: F9512, Sigma) was added into the cell which then were incubated on ice for 30 min. Afterwards, centrifugation was performed at 1,500 rpm for 3 min, and the supernatants were discarded. Cell pellets were washed with ice-cold PBS, and resuspended in 200 µl of ice-cold PBS, and then FACS was performed to detect the mean fluorescence intensity (MFI). Internalization efficiency was calculated by the formula: % of MFI tx=MFI of sample incubated at 37° C./MFI of control sample incubated at 4° C.×100; and Internalization percentage (% tx)=100-% of MFI tx.

The results are shown in Table 1, and as shown, ch4-3 and ch23-12 had internalization percentages similar to that of control antibody Sacituzumab, while no obvious internalization was observed for ch3-11 and ch11-4.

TABLE 1

| Internalization percentages of anti-human Trop-2 chimeric antibodies mediated by Trop-2 on the surface of cells | | | |
|---|---|---|---|
| | Internalization percentage (%) | | |
| | 1 h | 3 h | 5 h |
| ch3-11 | 1.12 | −5.13 | −8.48 |
| ch11-4 | −2 | −7.4 | −9.38 |
| ch23-12 | 16.24 | 21.12 | 27.15 |
| ch4-3 | 17.05 | 23.15 | 28.1 |
| Sacituzumab | 17.16 | 21.84 | 20.35 |

Example 8 Stability of Intolerance of Anti-Human
Trop-2 Chimeric Antibodies to Disruption Chimeric antibodies ch3-11, ch4-3, ch11-4 and ch23-12 were placed in PBS, PBS containing 10% N,N-Dimethylacetamide (DMA) (Cat.: ARK2190, Shanghai Feibo Chemical Technology Co., Ltd.) and PBS containing 20% DMA, at a concentration of 5 mg/ml respectively, at 37° C. for 2 h. Afterwards, the samples were freed from DMA using an ultrafiltration centrifuge tube with PBS used for buffer exchange. The samples were analyzed for purity by size exclusion-high-performance liquid chromatography (SEC-HPLC) using G3000WXL liquid chromatography column (Cat.: SEC-0046, Tosoh Corporation). The analysis results of purity are shown in Table 2.

The results showed that all the four antibodies could well tolerate DMA, with purity less obviously reduced in 10% DMA and slightly reduced in 20% DMA, suggesting the antibodies will be possibly well tolerant to the subsequent ADC conjugation process.

TABLE 2

| Purity of the antibodies analyzed by HPLC before and after DMA treatment | | | |
|---|---|---|---|
| | ch23-12 | ch3-11 | ch4-3 | ch11-4 |
| PBS | 97.52% | 97.57% | 99.47% | 99.25% |
| 10% DMA | 97.18% | 96.29% | 98.44% | 99.18% |
| 20% DMA | 93% | 96.27% | 94% | 98.96% |

Example 9 Humanization and Recombinant
Expression of Anti-Human Trop-2 Monoclonal
Antibodies 1. Humanization of Murine Monoclonal Antibody 23-12
(1) CDR Grafting Firstly, the heavy chain sequence of the murine antibody was comprehensively analyzed, and complementarity-determining regions (CDRs) of the antibody accounting for antigen binding and framework regions of the antibody supporting the conserved three-dimensional conformation of the antibody were determined. Subsequently, the most similar human template was searched for in the human antibody germline library (www2.mrc-lmb.cam.ac.uk/vbase/alignments2.php #VHEX) based on homology alignment results, CDR grafting was performed according to full-sequence BLAST results in combination with sequence characteristics of the heavy chain CDR3, and the heavy chain variable region (VH) of the murine antibody 23-12 was fully humanized in the framework regions. The most similar human template was searched for in the human antibody germline library (www2.mrc-lmb.cam.ac.uk/vbase/alignments2.php #VHEX) based on homology alignment results, CDR grafting was performed according to full-sequence BLAST results in combination with sequence characteristics of the light chain CDR3, and the light chain variable region (VL) of the murine antibody 23-12 was highly humanized in the framework regions.

The nucleotide sequence and the amino acid sequence of the humanized heavy chain variable region (h23-12_VH1) of CDR grafted antibody 23-12 are as shown in SEQ ID NO: 55 and SEQ ID NO: 13 respectively; and the nucleotide sequence and the amino acid sequence of the humanized light chain variable region (h23-12_VL1) of CDR grafted antibody 23-12 are as shown in SEQ ID NO: 56 and SEQ ID NO: 32 respectively.

```
SEQ ID NO: 13:
QVQLVQSGAEVKKPGASVKVSCKASGYTFTSYWMHWVRQAPGQGLEWMG

EITPSDNYTSYNQKFKGRVTITRDTSTSTAYMELSSLRSEDTAVYYCAR

GHGNYVSFDYWGQGTLVTVSS

SEQ ID NO: 32:
DIQMTQSPSSLSASVGDRVTITCRASQDISNYLNWYQQKPGKAPKLLIY

YTSRLHSGVPSRFSGSGSGTDFTLTISSLQPEDFATYFC

QQGYTLPPYTFGQGTKLEIKRTVAAP
```

(2) Mutation Design in CDRs

According to sequence characteristics of the murine antibody 23-12, mutations in CDR sequences in the CDR grafted humanized light and heavy chain variable regions were designed and the mutation sites are shown in Table 3.

TABLE 3

Design of humanized sequences of murine antibody 23-12

| Mutations relative to h23-12_VL1 | | Mutations relative to h23-12_VH1 | |
|---|---|---|---|
| h23-12_VL2 | T51A | h23-12_VH2 | S54G |
| h23-12_VL3 | R53S | h23-12_VH3 | N56G |
| h23-12_VL4 | H55E | h23-12_VH4 | T58G |

TABLE 3-continued

Design of humanized sequences of murine antibody 23-12

| Mutations relative to h23-12_VL1 | | Mutations relative to h23-12_VH1 | |
|---|---|---|---|
| h23-12_VL5 | H55Q | h23-12_VH5 | N61A |
| h23-12_VL6 | G91Y | h23-12_VH6 | H100E |
| h23-12_VL7 | T93S | h23-12_VH7 | H100Q |

Note:
amino acid residue positions were numbered according to the Kabat numbering system.

2. Recombinant Expression of Humanized Monoclonal Antibody 23-12

The light chain variable region and heavy chain variable region (h23-12_VL1 and h23-12_VH1) genes of CDR grafted antibody 23-12 were fully synthesized. The humanized h23-12_VH1 gene was cloned by enzyme digestion into eukaryotic transient-expression vector pKN041 at the upstream of the coding gene of the heavy chain constant region of human IgG1, and the nucleotide sequence and the amino acid sequence of the heavy chain constant region are as shown in SEQ ID NO: 59 and SEQ ID NO: 37 respectively. The humanized h23-12_VL1 gene was cloned by enzyme digestion into eukaryotic transient-expression vector pKN019 at the upstream of the coding gene of human Ck light chain, and the nucleotide sequence and the amino acid sequence of the light chain constant region are as shown in SEQ ID NO: 60 and SEQ ID NO: 38 respectively. As described, expression plasmids containing light and heavy chains of the CDR grafted antibody 23-12 were constructed and the obtained expression plasmids expressing light chain (pKN019-h23-12L1) and heavy chain (pKN019-h23-12H1) were transformed into *E. coli* cells for amplification, and then plasmids expressing the light chain h23-12L1 and the heavy chain h23-12H1 of the CDR grafted antibody 23-12 were isolated and obtained.

According to the mutation design shown in Table 3, site-directed mutagenesis was performed in the expression plasmids expressing light chain (pKN019-h23-12L1) and heavy chain (pKN019-h23-12H1) respectively using StarMut™ Gene Site-directed Mutagenesis Kit (Cat.: T111-01, GenStar). The mutated plasmids were transformed into *E. coli* cells for amplification, and expression plasmids expressing the light and the heavy chains of the humanized monoclonal antibodies with CDR mutations (h23-12H2 . . . h23-12H7; h23-12L2 . . . h23-12L7) were obtained, corresponding to the humanized sequences of murine antibody 23-12 shown in Table 3. All the plasmids containing various humanized heavy and light chain sequences of murine antibody 23-12 were combined as shown in Table 4 and transfected into HEK293 cells using 293fectin (Cat.: 12347019, Gibco) transfection reagent following the manufacturer's instructions for recombinant expression.

TABLE 4

Combinations of humanized heavy and light chain sequences of murine antibody 23-12

| | h23-12H1 | h23-12H2 | h23-12H3 | h23-12H4 | h23-12H5 | h23-12H6 | h23-12H7 |
|---|---|---|---|---|---|---|---|
| h23-12L1 | h23-12-1 | h23-12-2 | h23-12-3 | h23-12-4 | h23-12-5 | h23-12-6 | h23-12-7 |
| h23-12L2 | h23-12-8 | h23-12-9 | h23-12-10 | h23-12-11 | h23-12-12 | h23-12-13 | h23-12-14 |
| h23-12L3 | h23-12-15 | h23-12-16 | h23-12-17 | h23-12-18 | h23-12-19 | h23-12-20 | h23-12-21 |
| h23-12L4 | h23-12-22 | h23-12-23 | h23-12-24 | h23-12-25 | h23-12-26 | h23-12-27 | h23-12-28 |
| h23-12L5 | h23-12-29 | h23-12-30 | h23-12-31 | h23-12-32 | h23-12-33 | h23-12-34 | h23-12-35 |
| h23-12L6 | h23-12-36 | h23-12-37 | h23-12-38 | h23-12-39 | h23-12-40 | h23-12-41 | h23-12-42 |
| h23-12L7 | h23-12-43 | h23-12-44 | h23-12-45 | h23-12-46 | h23-12-47 | h23-12-48 | h23-12-49 |

Note:

Table 4 shows antibodies obtained from the combinations of various heavy and light chains derived from murine antibody 23-12. For example, h23-12-1 refers to an antibody composed of the humanized light chain h23-12L1 and humanized heavy chain h23-12H1 of the murine antibody 23-12, and so on.

5-6 days after cell transfection, culture supernatants were purified through ProA affinity chromatography column to obtain different humanized antibodies. Affinities of the obtained antibodies were determined by an assay including capturing Fc fragments of the antibodies with anti-human IgG Fc capture (AHC) biosensors using Octet® QKe Bio-Layer Interferometry (BLI) system instrument from Fortebio. For the assay, each of the humanized antibodies and control antibody Sacituzumab was diluted to 4 μg/ml in PBS, and was allowed to flow through the surface of an AHC biosensor (Cat.: 18-0015, PALL) for 120 s. Recombinant human Trop-2-his protein (ACCESSION NO.: NP_002344.2, AA 1-274) was used as a mobile phase, and its concentration was 60 nM. The binding time was 100 s and the dissociation time was 300 s. When the assay was finished, data from which the response values of blank control had been deducted were fitted to a 1:1 Langmuir binding model using software, and then kinetic constants for antigen-antibody binding were calculated.

Affinities of the antibodies obtained from the combinations of mutants of murine antibody 23-12, chimeric antibody ch23-12 and control antibody Sacituzumab to recombinant human Trop-2-his protein were determined by ForteBio (Table 5).

TABLE 5

Detection results of the affinities of the antibodies to recombinant human Trop-2 extracellular domain

| Antibody | KD value (M) |
|---|---|
| Sacituzumab | 7.23E-10 |
| ch23-12 | 7.15E-12 |
| h23-12-1 | 2.72E-10 |
| h23-12-2 | 8.93E-10 |
| h23-12-3 | 1.50E-08 |
| h23-12-4 | 8.27E-10 |
| h23-12-5 | 3.20E-09 |
| h23-12-6 | 2.98E-10 |
| h23-12-7 | 6.80E-09 |
| h23-12-8 | 9.00E-10 |
| h23-12-9 | 1.10E-09 |
| h23-12-10 | 9.62E-09 |
| h23-12-11 | 8.81E-10 |
| h23-12-12 | 2.62E-08 |
| h23-12-13 | 9.16E-10 |
| h23-12-14 | 2.39E-08 |
| h23-12-15 | 1.43E-09 |
| h23-12-16 | 2.87E-09 |
| h23-12-17 | 2.80E-08 |
| h23-12-18 | 9.91E-10 |
| h23-12-19 | 1.00E-08 |
| h23-12-20 | 1.46E-09 |
| h23-12-21 | 2.28E-08 |
| h23-12-22 | 1.30E-09 |
| h23-12-23 | 7.70E-10 |
| h23-12-24 | 5.21E-09 |
| h23-12-25 | 5.02E-10 |
| h23-12-26 | 5.43E-09 |
| h23-12-27 | 4.96E-10 |
| h23-12-28 | 4.13E-09 |
| h23-12-29 | 6.72E-09 |
| h23-12-30 | 9.76E-09 |
| h23-12-31 | 6.39E-08 |
| h23-12-32 | 6.01E-10 |
| h23-12-33 | 8.91E-09 |
| h23-12-34 | 5.57E-09 |
| h23-12-35 | 9.77E-09 |
| h23-12-36 | 8.81E-09 |
| h23-12-37 | 8.93E-10 |
| h23-12-38 | 7.86E-09 |
| h23-12-39 | 4.92E-10 |
| h23-12-40 | 2.16E-09 |
| h23-12-41 | 7.82E-10 |
| h23-12-42 | 3.09E-09 |

32

TABLE 5-continued

Detection results of the affinities of the antibodies to recombinant human Trop-2 extracellular domain

| Antibody | KD value (M) |
|---|---|
| h23-12-43 | 9.80E-10 |
| h23-12-44 | 7.17E-10 |
| h23-12-45 | 4.09E-09 |
| h23-12-46 | 3.12E-10 |
| h23-12-47 | 2.31E-09 |
| h23-12-48 | 4.05E-10 |
| h23-12-49 | 2.99E-09 |

Antibody h23-12-25 having an affinity measured by a KD value of 5.02E-10M was selected and was named as h23-12, which was used for further functional verification. The nucleotide sequence and the amino acid sequence of the heavy chain variable region of the antibody are as shown in SEQ ID NO: 57 and SEQ ID NO: 14 respectively; and the nucleotide sequence and the amino acid sequence of the light chain variable region of the antibody are as shown in SEQ ID NO: 58 and SEQ ID NO: 33 respectively.

SEQ ID NO: 14:
QVQLVQSGAEVKKPGASVKVSCKASGYTFTSYWMHWVRQAPGQGLEWMG

EITPSDNYGSYNQKFKGRVTITRDTSTSTAYMELSSLRSEDTAVYYCAR

GHGNYVSFDYWGQGTLVTVSS

SEQ ID NO: 33:
DIQMTQSPSSLSASVGDRVTITCRASQDISNYLNWYQQKPGKAPKLLIY

YTSRLESGVPSRFSGSGSGTDFTLTISSLQPEDFATYFC

QQGYTLPPYTFGQGTKLEIK

3. Humanization of Murine Monoclonal Antibody 4-3
(1) CDR grafting

Firstly, the heavy chain sequence of the murine antibody was comprehensively analyzed, and complementarity-determining regions (CDRs) of the antibody accounting for antigen binding and framework regions of the antibody supporting the conserved three-dimensional conformation of the antibody were determined. Subsequently, the most similar human template was searched for in the human antibody germline library (www2.mrc-lmb.cam.ac.uk/vbase/alignments2.php #VHEX) based on homology alignment results, CDR grafting was performed according to full-sequence BLAST results in combination with sequence characteristics of the heavy chain CDR3, and the heavy chain variable region (VH) of the murine antibody 4-3 was fully humanized in the framework regions. The most similar human template was searched for in the human antibody germline library (www2.mrc-lmb.cam.ac.uk/vbase/alignments2.php #VHEX) based on homology alignment results, CDR grafting was performed according to full-sequence BLAST results in combination with sequence characteristics of the light chain CDR3, and the light chain variable region (VL) of the murine antibody 4-3 was fully humanized in the framework regions.

The nucleotide sequence and the amino acid sequence of the humanized heavy chain variable region (h4-3_VH1) of CDR grafted antibody 4-3 are as shown in SEQ ID NO: 45 and SEQ ID NO: 3 respectively; and the nucleotide sequence and the amino acid sequence of the humanized light chain variable region (h4-3_VL1) of CDR grafted antibody 4-3 are as shown in SEQ ID NO: 46 and SEQ ID NO: 20 respectively.

SEQ ID NO: 3:
EVQLVQSGPEVKKPGASVKVSCKASGFTFT<u>DYVIG</u>WVRQAPGQGLEWIG

<u>EIYLGSGTIYYTEKFKG</u>RVTMTADTSTSTAYMELSSLRSEDTAVYYCAR

<u>GSIFPFDYW</u>GQGTLVTVSS

SEQ ID NO: 20:
DIQLTQSPSSLSASVGDRVTITC<u>SASSSVSYMY</u>WYQQKPGKAPKLLIY

<u>DTSTLAS</u>GVPSRFSGSGSGTDFTLTISSLQPEDFATYYC

<u>QQWSSYPYT</u>FGQGTKLEIK (2) Mutation Design in CDRs

According to sequence characteristics of the murine antibody 4-3, mutations in CDR sequences in the CDR grafted humanized light and heavy chain variable regions were designed and the mutation sites are shown in Table 6.

TABLE 6

| Design of humanized sequences of murine antibody 4-3 | | | |
|---|---|---|---|
| Mutations relative to h4-3_VL1 | | Mutations relative to h4-3_VH1 | |
| h4-3_VL2 | S24R | h4-3_VH2 | T61A |
| h4-3_VL3 | T50A | h4-3_VH3 | E62Q |
| h4-3_VL4 | A54Q | h4-3_VH4 | P103Y |
| h4-3_VL5 | S91N | | |

Note:
amino acid residue positions were numbered according to the Kabat numbering system.

4. Recombinant Expression of Humanized Monoclonal Antibody 4-3

The light chain variable region and heavy chain variable region (h4-3_VL1 and h4-3_VH1) genes of CDR grafted antibody 4-3 were fully synthesized. The humanized h4-3_VH1 gene was cloned by enzyme digestion into eukaryotic transient-expression vector pKN041 at the upstream of the coding gene of the heavy chain constant region of human IgG1, and the nucleotide sequence and the amino acid sequence of the heavy chain constant region are as shown in SEQ ID NO: 59 and SEQ ID NO: 37 respectively. The humanized h4-3_VL1 gene was cloned by enzyme digestion into eukaryotic transient-expression vector pKN019 at the upstream of the coding gene of human Cκ light chain, and the nucleotide sequence and the amino acid sequence of the light chain constant region are as shown in SEQ ID NO: 60 and SEQ ID NO: 38 respectively. As described, expression plasmids containing light and heavy chains of the CDR grafted antibody 4-3 were constructed and the obtained expression plasmids expressing light chain (pKN019-h24-3L1) and heavy chain (pKN019-h4-3H1) were transformed into *E. coli* cells for amplification, and then plasmids expressing the light chain h4-3L1 and the heavy chain h4-3H1 of the CDR grafted antibody 4-3 were isolated and obtained.

According to the mutation design shown in Table 6, site-directed mutagenesis was performed in the expression plasmids expressing light chain (pKN019-h4-3L1) and heavy chain (pKN019-h4-3H1) respectively using StarMut™ Gene Site-directed Mutagenesis Kit (Cat.: T111-01, GenStar). The mutated plasmids were transformed into *E. coli* cells for amplification, and obtained expression plasmids expressing the light and the heavy chains of the humanized monoclonal antibodies with CDR mutations (h4-3H2 . . . h4-3H4; h4-3L2 . . . h4-3L5), corresponding to the humanized sequences of murine antibody 4-3 shown in Table 6. All the plasmids containing various humanized heavy and light chain sequences of murine antibody 4-3 were combined as shown in Table 7 and transfected into HEK293 cells using 293fectin (Cat.: 12347019, Gibco) transfection reagent following the manufacturer's instructions for recombinant expression.

TABLE 7

| Combinations of humanized heavy and light chain sequences of murine antibody 4-3 | | | | |
|---|---|---|---|---|
| | h4-3 H1 | h4-3 H2 | h4-3 H3 | h4-3 H4 |
| h4-3 L1 | h4-3-1 | h4-3-2 | h4-3-3 | h4-3-4 |
| h4-3 L2 | h4-3-5 | h4-3-6 | h4-3-7 | h4-3-8 |
| h4-3 L3 | h4-3-9 | h4-3-10 | h4-3-11 | h4-3-12 |
| h4-3 L4 | h4-3-13 | h4-3-14 | h4-3-15 | h4-3-16 |
| h4-3 L5 | h4-3-17 | h4-3-18 | h4-3-19 | h4-3-20 |

Note:
Table 7 shows antibodies obtained from the combinations of various heavy and light chains derived from murine antibody 4-3. For example, h4-3-1 refers to an antibody composed of the humanized light chain h4-3L1 and humanized heavy chain h4-3H1 of the murine antibody 4-3, and so on.

5-6 days after cell transfection, culture supernatants were purified through ProA affinity chromatography column to obtain different humanized antibodies. Affinities of the obtained antibodies were determined by an assay including capturing Fc fragments of the antibodies with anti-human IgG Fc capture (AHC) biosensors using Octet® QKe Bio-Layer Interferometry (BLI) system instrument from Fortebio. For the assay, each of the humanized antibodies and control antibody Sacituzumab was diluted to 4 μg/ml in PBS, and was allowed to flow through the surface of an AHC biosensor (Cat.: 18-0015, PALL) for 120 s. Recombinant human Trop-2-his protein (ACCESSION NO.: NP_002344.2, AA 1-274) was used as a mobile phase, and its concentration was 60 nM. The binding time was 100 s and the dissociation time was 300 s. When the assay was finished, data from which the response values of blank control had been deducted were fitted to a 1:1 Langmuir binding model using software, and then kinetic constants for antigen-antibody binding were calculated.

Affinities of the antibodies obtained from the combinations of mutants of murine antibody 23-12, chimeric antibody ch4-3 and control antibody Sacituzumab to recombinant human Trop-2-his protein were determined by ForteBio (Table 8).

TABLE 8

| Detection results of the affinities of the antibodies to recombinant human Trop-2 extracellular domain | |
|---|---|
| Antibody | KD value (M) |
| Sacituzumab | 7.23E−10 |
| ch4-3 | 3.00E−10 |
| h4-3-1 | 3.04E−10 |
| h4-3-2 | 4.11E−10 |
| h4-3-3 | 5.01E−10 |
| h4-3-4 | 6.36E−10 |
| h4-3-5 | 2.73E−10 |
| h4-3-6 | 3.97E−10 |
| h4-3-7 | 4.66E−10 |
| h4-3-8 | 8.62E−10 |
| h4-3-9 | 3.17E−10 |
| h4-3-10 | 7.63E−10 |
| h4-3-11 | 8.02E−10 |
| h4-3-12 | 1.03E−09 |
| h4-3-13 | 2.81E−10 |
| h4-3-14 | 5.71E−10 |
| h4-3-15 | 6.87E−10 |
| h4-3-16 | 1.53E−09 |

TABLE 8-continued

| Detection results of the affinities of the antibodies to recombinant human Trop-2 extracellular domain | |
| --- | --- |
| Antibody | KD value (M) |
| h4-3-17 | 5.42E-10 |
| h4-3-18 | 6.71E-10 |
| h4-3-19 | 5.99E-10 |
| h4-3-20 | 8.92E-10 |

Antibody h4-3-1 having an affinity measured by a KD value of 3.04E-10M was selected and was named as h4-3, which was used for further functional verification. The nucleotide sequence and the amino acid sequence of the heavy chain variable region of the antibody are as shown in SEQ ID NO: 45 and SEQ ID NO: 3 respectively; and the nucleotide sequence and the amino acid sequence of the light chain variable region of the antibody are as shown in SEQ ID NO: 46 and SEQ ID NO: 20 respectively.

SEQ ID NO: 3:
EVQLVQSGPEVKKPGASVKVSCKASGFTFTDYVIGWVRQAPGQGLEWIG

EIYLGSGTIYYTEKFKGRVTMTADTSTSTAYMELSSLRSEDTAVYYCAR

GSIFPFDYWGQGTLVTVSS

SEQ ID NO: 20:
DIQLTQSPSSLSASVGDRVTITCSASSSVSYMYWYQQKPGKAPKLLIY

DTSTLASGVPSRFSGSGSGTDFTLTISSLQPEDFATYYC

QQWSSYPYTFGQGTKLEIK

5. Humanization of Murine Monoclonal Antibody 11-4

(1) CDR Grafting

Firstly, the heavy chain sequence of the murine antibody was comprehensively analyzed, and complementarity-determining regions (CDRs) of the antibody accounting for antigen binding and framework regions of the antibody supporting the conserved three-dimensional conformation of the antibody were determined. Subsequently, the most similar human template was searched for in the human antibody germline library (www2.mrc-lmb.cam.ac.uk/vbase/alignments2.php #VHEX) based on homology alignment results, CDR grafting was performed according to full-sequence BLAST results in combination with sequence characteristics of the heavy chain CDR3, and the heavy chain variable region (VH) of the murine antibody 11-4 was fully humanized in the framework regions. The most similar human template was searched for in the human antibody germline library (www2.mrc-lmb.cam.ac.uk/vbase/alignments2.php #VHEX) based on homology alignment results, CDR grafting was performed according to full-sequence BLAST results in combination with sequence characteristics of the light chain CDR3, and the light chain variable region (VL) of the murine antibody 11-4 was fully humanized in the framework regions.

The nucleotide sequence and the amino acid sequence of the humanized heavy chain variable region (h11-4_VH1) of CDR grafted antibody 11-4 are as shown in SEQ ID NO: 49 and SEQ ID NO: 50 respectively; and the nucleotide sequence and the amino acid sequence of the humanized light chain variable region (h11-4_VL1) of CDR grafted antibody 4-3 are as shown in SEQ ID NO: 50 and SEQ ID NO: 25 respectively.

SEQ ID NO: 6:
QVQLVQSGAEVKKPGASVKVSCKASGYTFTSYWINWVRQAPGQGLEWMG

NIYPSNSYTNYNQKFKDRVTMTRDTSTSTVYMELSSLRSEDTAVYYCAR

YRSDGFAYWGQGTLVTVSS

SEQ ID NO: 25:
EIVLTQSPATLSLSPGERATLSCRASQNIGTSIHWYQQKPGQAPRLLIY

FASESISGIPARFSGSGSGTDFTLTISSLEPEDFAVYYC

QQSNSWPFTFGGGTKVEIK (2) Mutation Design in CDRs

According to sequence characteristics of the murine antibody 11-4, mutations in CDR sequences in the CDR grafted humanized light and heavy chain variable regions were designed and the mutation sites are shown in Table 9.

TABLE 9

| Design of humanized sequences of murine antibody 11-4 | | | |
| --- | --- | --- | --- |
| Mutations relative to h11-4_VL1 | | Mutations relative to h11-4_VH1 | |
| h11-4_VL2 | Y49E | h11-4_VH2 | A97S |
| h11-4_VL3 | H34E, Y49E | h11-4_VH3 | R98S |
| h11-4_VL4 | H34S, Y49E | h11-4_VH4 | Q1E, A97S, R98S |
| h11-4_VL5 | H34A, Y49E | h11-4_VH5 | Q1E, A97S, R98S, D102E |
| | | h11-4_VH6 | Q1E, A97S, R98S, D102G |
| | | h11-4_VH7 | Q1E, A97S, R98S, G103A |

Note:
amino acid residue positions were numbered according to the Kabat numbering system.

6. Recombinant Expression of Humanized Monoclonal Antibody 11-4

The light chain variable region and heavy chain variable region (h11-4_VL1 and h11-4_VH1) genes of CDR grafted antibody 11-4 were fully synthesized. The humanized h11-4_VH1 gene was cloned by enzyme digestion into eukaryotic transient-expression vector pKN041 at the upstream of the coding gene of the heavy chain constant region of human IgG1, and the nucleotide sequence and the amino acid sequence of the heavy chain constant region are as shown in SEQ ID NO: 59 and SEQ ID NO: 37 respectively. The humanized h11-4_VL1 gene was cloned by enzyme digestion into eukaryotic transient-expression vector pKN019 at the upstream of the coding gene of human CK light chain, and the nucleotide sequence and the amino acid sequence of the light chain constant region are as shown in SEQ ID NO: 60 and SEQ ID NO: 38 respectively. As described, expression plasmids containing light and heavy chains of the CDR grafted antibody 11-4 were constructed and the obtained expression plasmids expressing light chain (pKN019-h11-4L1) and heavy chain (pKN019-h11-4H1) were transformed into E. coli cells for amplification, and then plasmids expressing the light chain h11-4L1 and the heavy chain h11-4H1 of the CDR grafted antibody 11-4 were isolated and obtained.

According to the mutation design shown in Table 9, site-directed mutagenesis was performed in the expression plasmids expressing light chain (pKN019-h11-4L1) and heavy chain (pKN019-h11-4H1) respectively using StarMut™ Gene Site-directed Mutagenesis Kit (Cat.: T111-01, GenStar). The mutated plasmids were transformed into E. coli cells for amplification, and expression plasmids expressing the light and the heavy chains of the humanized monoclonal antibodies with CDR mutations (h11-4H2 . . .

h11-4H7; h11-4L2 . . . h11-4L5), corresponding to the humanized sequences of murine antibody 4-3 shown in Table 9. All the plasmids containing various humanized heavy and light chain sequences of murine antibody antibody 11-4 were combined as shown in Table 10 and transfected into HEK293 cells using 293fectin (Cat.: 12347019, Gibco) transfection reagent following the manufacturer's instructions for recombinant expression.

TABLE 10

Combinations of humanized heavy and light chain sequences of murine antibody 11-4

|          | h11-4 H1 | h11-4 H2 | h11-4 H3 | h11-4 H4 | h11-4 H5 | h11-4 H6 | h11-4 H7 |
|----------|----------|----------|----------|----------|----------|----------|----------|
| h11-4 L1 | h11-4-1  | h11-4-2  | h11-4-3  | h11-4-4  |          |          |          |
| h11-4 L2 | h11-4-5  | h11-4-6  | h11-4-7  | h11-4-8  |          |          |          |
| h11-4 L3 |          |          |          | h11-4-9  | h11-4-10 | h11-4-11 | h11-4-12 |
| h11-4 L4 |          |          |          | h11-4-13 | h11-4-14 | h11-4-15 | h11-4-16 |
| h11-4 L5 |          |          |          | h11-4-17 | h11-4-18 | h11-4-19 | h11-4-20 |

Note: Table 10 shows antibodies obtained from the combinations of various heavy and light chains derived from murine antibody 11-4. For example, h11-4-1 refers to an antibody composed of the humanized light chain h11-4L1 and humanized heavy chain h11-4H1 of the murine antibody 11-4, and so on.

5-6 days after cell transfection, culture supernatants were purified through ProA affinity chromatography column to obtain different humanized antibodies. Affinities of the obtained antibodies were determined by an assay including capturing Fc fragments of the antibodies with anti-human IgG Fc capture (AHC) biosensors using Octet® QKe Bio-Layer Interferometry (BLI) system instrument from Fortebio. For the assay, each of the humanized antibodies and control antibody Sacituzumab was diluted to 4 μg/ml in PBS, and was allowed to flow through the surface of an AHC biosensor (Cat.: 18-0015, PALL) for 120 s. Recombinant human Trop-2-his protein (ACCESSION NO.: NP_002344.2, AA 1-274) was used as a mobile phase, and its concentration was 60 nM. The binding time was 100 s and the dissociation time was 300 s. When the assay was finished, data from which the response values of blank control had been deducted were fitted to a 1:1 Langmuir binding model using software, and then kinetic constants for antigen-antibody binding were calculated.

Affinities of the antibodies obtained from the combinations of mutants of murine antibody 11-4, chimeric antibody ch11-4 and control antibody Sacituzumab to recombinant human Trop-2-his protein were determined by ForteBio (Table 11).

TABLE 11

Detection results of the affinities of the antibodies to recombinant human Trop-2 extracellular domain

| Antibody    | KD value (M) |
|-------------|--------------|
| Sacituzumab | 7.84E−10     |
| ch11-4      | 2.64E−10     |
| h11-4-1     | 2.16E−09     |
| h11-4-2     | 9.91E−10     |
| h11-4-3     | 8.68E−10     |
| h11-4-4     | 8.11E−10     |
| h11-4-5     | 1.08E−09     |
| h11-4-6     | 9.52E−10     |
| h11-4-7     | 8.03E−10     |
| h11-4-8     | 2.22E−10     |
| h11-4-9     | 3.01E−10     |
| h11-4-10    | 3.51E−10     |
| h11-4-11    | 3.75E−10     |
| h11-4-12    | 2.82E−10     |
| h11-4-13    | 2.11E−10     |
| h11-4-14    | 3.52E−10     |

TABLE 11-continued

Detection results of the affinities of the antibodies to recombinant human Trop-2 extracellular domain

| Antibody  | KD value (M) |
|-----------|--------------|
| h11-4-15  | 3.89E−10     |
| h11-4-16  | 2.31E−10     |

TABLE 11-continued

Detection results of the affinities of the antibodies to recombinant human Trop-2 extracellular domain

| Antibody  | KD value (M) |
|-----------|--------------|
| h11-4-17  | 2.38E−10     |
| h11-4-18  | 3.94E−10     |
| h11-4-19  | 2.54E−10     |
| h11-4-20  | 2.10E−10     |

Example 10 Detection Via ELISA of Species-Specific Binding of Anti-Trop-2 Humanized Antibodies to Trop-2

Plates were coated with recombinant human Trop-2-his protein (ACCESSION NO.: NP_002344.2, AA 1-274), recombinant cynomolgus Trop-2-his protein (ACCESSION NO.: UniProtKB-A0A2K5UE71, AA 1-272), and recombinant mouse Trop-2-his protein (Cat.: 50922-M08H, Beijing Yiqiao Shenzhou Science and Technology Co., Ltd.) respectively overnight at 4° C., each protein having a coating concentration of 1 μg/ml respectively. Washed with PBS 3 times, the plates were blocked with the added 5% BSA PBS at 37° C. for 60 min, and then washed 3 times with PBST. Different concentrations of h23-12 (serial dilutions of 14 concentrations obtained through 3-fold serially diluting a solution with an initial concentration of 10 μg/ml), h4-3 (serial dilutions of 12 concentrations obtained through 3-fold serially diluting a solution with an initial concentration of 3 μg/ml), and Sacituzumab (serial dilutions of 12 concentrations obtained through 3-fold serially diluting a solution with an initial concentration of 3 μg/ml) were added into the plates, with each concentration provided in a parallel well. The plates were incubated at 37° C. for 60 min, and then were washed 4 times with PBST. 1:5000 dilution of HRP-anti-human Fc (Cat.: 109-035-098, Jackson ImmunoResearch) was added into the plates for incubation at 37° C. for 30 min. Afterwards, the plates were washed with PBST 4 times, and TMB substrate was added for color development at 37° C. for 10 min. Then 2M HCl was added to stop reaction; and absorbances at 450 nm and at 630 nm (as reference wavelength) were read, and A450 nm-630 nm values of the wells in the plates were recorded.

The experiment results showed that h23-12, h4-3, and control antibody Sacituzumab could specifically bind recombinant human and cynomolgus Trop-2, but had no binding activity to mouse Trop-2 (FIG. 6, and Table 12), which provided a basis for pharmacological and toxicological experiments of the humanized antibodies.

TABLE 12

| EC50 of binding of anti-Trop-2 humanized antibodies to Trop-2 of different species | | |
|---|---|---|
| | EC50 (nM) | |
| Antibody | human Trop-2 | cynomolgus Trop-2 |
| h23-12 | 0.04729 | 0.1245 |
| h4-3 | 0.0469 | 0.04615 |
| Sacituzumab | 0.07032 | 0.07262 |

Example 11 Analysis of Affinities of Anti-Human Trop-2 Humanized Antibodies

Affinities of the antibodies were determined by an assay including capturing Fc fragments of the antibodies with anti-human IgG Fc capture (AHC) biosensors using Octet® QKe Bio-Layer Interferometry (BLI) system instrument from Fortebio.

For the assay, each of the antibodies (h23-12, h4-3, and control antibody Sacituzumab) was diluted to 4 µg/ml in PBS, and was allowed to flow through the surface of an AHC biosensor (Cat.: 18-0015, PALL) for 120 s. Recombinant human Trop-2-his protein (ACCESSION NO.: NP_002344.2, AA 1-274) was used as a mobile phase. The Trop-2-his protein was used in following concentrations which corresponded to different antibodies: in case of h23-12, the Trop-2 was used in concentrations of 23, 30, 45, and 75 nM; in case of h4-3, it was used in concentrations of 23, 30, 45, and 60 nM; and in case of Sacituzumab, it was used in concentrations of 23, 30, 45, and 75 nM. The binding time was 100 s and the dissociation time was 300 s. When the assay was finished, data from which the response values of blank control had been deducted were fitted to a 1:1 Langmuir binding model using software, and then kinetic constants for antigen-antibody binding were calculated.

Reaction curves of h23-12, h4-3, and control antibody Sacituzumab with the recombinant human Trop-2 protein are shown in FIG. 7. The curves were fitted and the affinities were calculated, and it was shown that h23-12 had an affinity measured by a KD value of 6.40E-10M, h4-3 had an affinity measured by a KD value of 5.45E-10M, and Sacituzumab had an affinity measured by a KD value of 9.41E-10M. Kinetic parameters in detail are shown in Table 13. The results showed that h23-12 and h4-3 had high affinities to human Trop-2, equivalent to that of control antibody Sacituzumab, and h23-12 had a dissociation value superior to that of Sacituzumab.

TABLE 13

| Detection results of the affinities of the anti-human Trop-2 humanized antibodies to recombinant human Trop-2 extracellular domain | | | |
|---|---|---|---|
| | KD value (M) | kon (1/Ms) | kdis (1/s) |
| h23-12 | 6.40E-10 | 1.78E+05 | 1.14E-04 |
| h4-3 | 5.45E-10 | 2.67E+05 | 1.46E-04 |
| Sacituzumab | 9.41E-10 | 2.08E+05 | 1.94E-04 |

Example 12 Internalization Activities of Anti-Human Trop-2 Humanized Antibodies Binding to Trop-2 on the Surface of Cells NCI-N87 human gastric cancer cells naturally expressing human Trop-2 were inoculated at a density of $2\times10^3$ cells/well into 96-well cell culture plates and cultured for 24 h. The cells were washed once with PBS and the supernatants were discarded. H23-12 and control antibody Sacituzumab labeled with Mix-n-Stain™ CF™ 488A Antibody Labeling Kit (Cat.: MX488AS100, Sigma) were diluted to 15 µg/ml with RPMI 1640 (containing 10% FBS), and added to the NCI-N87 cells. The plates were divided into two groups, and one group was placed in an electric heating constant temperature incubator at 37° C., and one group was placed in a refrigerator at 4° C. as negative control. The plates as negative control were incubated for 30 min, washed with PBS 3 times, and observed and photographed with a fluorescence microscope. The plates of experiment groups were incubated at 37° C. for 5 h, and then observed and photographed with a fluorescence microscope.

Experimental results (FIG. 8) showed that both the humanized h23-12 and control antibody Sacituzumab were able to be endocytosed through Trop-2 mediated endocytosis and distributed as spots in cytoplasm, suggesting that the internalization activities are maintained after antibody humanization.

Internalization rate on BxPC cells at 3 h was measured via FACS using the procedure described in Example 7, and the results are shown in Table 14, suggesting that the internalization rates after humanization are comparable to that of Sacituzumab.

TABLE 14

| Internalization percentages of anti-human Trop-2 antibodies mediated by Trop-2 on the surface of BxPC cells | | | |
|---|---|---|---|
| | Fluorescence intensity (MFI) | | Internalization |
| Antibody | 4° C. | 37° C. | percentage (%) |
| h23-12 | 57771.6 | 30444.1 | 47.3 |
| Sacituzumab | 60612 | 31793.8 | 47.55 |
| NC-IgG1 | 739.4 | 715.1 | 3.29 |

Example 13 Pharmacokinetic Study in Balb/C Nude Mice Administered with Single Doses Healthy female 5 weeks old Balb/C nude mice were grouped, 2 in each group. The mice were intraperitoneally injected once with a single dose of h23-12 (15 mg/kg), and sera were collected respectively at 5 h, 25 h, 48 h, 96 h, 168 h and 240 h and stored at −20° C. A control group was set, and the mice in the control group were intraperitoneally injected with control antibody Sacituzumab of the same dosage as h23-12 for comparison. Pharmacokinetic characteristics of the antibodies were observed.

Healthy female 5 weeks old Balb/C nude mice were grouped, 4 in each group. The mice were intraperitoneally injected one time with a single dose of h4-3 (20 mg/kg), and sera were collected respectively at 4 h, 8 h, 24 h, 48 h, 96 h, 144 h, 192 h and 240 h and stored at −20° C. Pharmacokinetic characteristics of the antibody were observed.

Drug concentrations in serum were measured via ELISA using coated human Trop-2-his (ACCESSION NO.: NP_002344.2, AA 1-274); and in the meanwhile a standard curve was established. A linear curve was fitted by plotting the concentrations of standard antibody (Y axis) against OD values (X axis), and the content of an antibody in serum was obtained by substituting the OD value of the detected serum into the formula, and the half-life $T_{1/2}$ of the antibody drug was calculated according to the formula $T_{1/2}=|0.693/k|$.

The results of drug concentration versus time curves showed that h23-12, h4-3, and control antibody Sacituzumab all had relatively long half-lives and exhibited comparable half-lives of drug metabolism (panel 9A, panel 9B, and Table 15), suggesting that the antibodies have no obvious inactivation phenomenon in vivo, and have good structural stability. The metabolism of the antibodies meets the basic characteristics of a monoclonal antibody drug, and $T_{1/2}$ is about 170 h.

TABLE 15

Pharmacokinetic parameters of anti-Trop-2 antibodies in nude mice administered with single doses

| | $T_{1/2}$ (detected by Trop-2) |
|---|---|
| Sacituzumab (n = 2) | 168 ± 14 |
| h23-12(n = 2) | 174 ± 12 |
| h4-3 (n = 4) | 180 ± 57 |

Example 14 Analysis of Affinities of Anti-Trop-2 Naked Antibodies and ADCs Thereof Affinities of the antibodies were determined by an assay including capturing Fc fragments of the antibodies with anti-human IgG Fc capture (AHC) biosensors using Octet® QKe Bio-Layer Interferometry (BLI) system instrument from Fortebio.

Firstly, an antibody labeled with SN38 used in ADC drugs was prepared. The antibody was reduced for 2 h in a sodium phosphate buffer, pH 7.0±0.5, using 20 equivalents of Dithiothreitol (DTT), and the reduced antibody was purified using an ultrafiltration centrifuge tube to remove excess DTT and exchanged into a sodium phosphate buffer, pH 7.0±0.5. The reduced antibody was incubated with CL2A-SN-38 for 30 min at ambient temperature using 7-15% (v/v) DMSO as a co-solvent. Finally, excess small molecules were removed through an ultrafiltration centrifuge tube. Molecular weight of the obtained antibody-drug conjugate was analyzed by mass spectrometry, and drug to antibody ratio (DAR) value of the ADC was calculated. It was confirmed eventually that 7.5 SN38 molecules were linked to one antibody.

For the assay, SN38-labeled antibodies prepared as described above: h23-12-SN38, ch4-3-SN38, ch11-4-SN38, and positive control antibody Sacituzumab-SN38, as well as naked antibodies h23-12, ch4-3, ch11-4, and positive control antibody Sacituzumab were diluted to 4 µg/ml with PBS and allowed to flow through the surface of an AHC biosensor (Cat.: 18-0015, PALL) for 120 s. Recombinant human Trop-2-his protein (ACCESSION NO.: NP_002344.2, AA 1-274) was used as a mobile phase, and its concentration was 60 nM. The binding time was 300 s and the dissociation time was 300 s. When the assay was finished, data from which the response value of blank control had been deducted were fitted to a 1:1 Langmuir binding model using software, and then kinetic constants for antigen-antibody binding were calculated.

As shown in Table 16, no significant changes in the affinities of the antibodies were observed when the antibodies were labeled with SN38 thereby forming ADCs, as compared with the affinities when they were naked.

TABLE 16

Detection results of the affinities of the anti-Trop-2 naked antibodies and ADCs thereof

| | KD value (M) | |
|---|---|---|
| Antibody | Naked | Labeled with SN38 |
| h23-12 | 5.07E−10 | 4.41E−10 |
| ch4-3 | 3.23E−10 | 1.77E−10 |
| ch11-4 | 1.76E−10 | 7.34E−11 |
| Sacituzumab | 5.83E−10 | 4.31E−10 |

Example 15 Detection Via FACS of Internalization of Anti-Trop-2 Naked Antibodies and ADCs Thereof Mediated by BXPC-3 Cells Internalization rates on BXPC-3 human pancreatic cancer cells and NCI-N87 human gastric cancer cell were detected respectively according to the procedure as described in Example 7. Antibodies to be detected included ADC drugs i.e. SN38 labeled antibodies prepared as described above: h23-12-SN38, ch4-3-SN38, ch11-4-SN38, positive control antibody Sacituzumab-SN38, as well as naked antibodies h32-12, ch4-3, ch11-4, positive control antibody Sacituzumab, and negative isotype control antibody NC-IgG1, and each was 10 µg/ml.

As shown in Table 17 and Table 18, h23-12 naked and h23-12 labeled with SN38 thereby forming an ADC had similar internalization percentages, which were similar to that of the control antibody; and ch4-3 and ch11-4 when labeled with SN38 to form ADCs had higher internalization percentages than when they were naked.

TABLE 17

Internalization percentages of anti-human Trop-2 antibodies mediated by Trop-2 on the surface of NCI-N87 cells

| | Internalization percentage, 1 h | |
|---|---|---|
| Antibody | Naked | Labeled with SN38 |
| h23-12 | 54.04% | 51.09% |
| ch4-3 | 50.16% | 64.56% |
| Sacituzumab | 49.33% | 47.49% |
| NC-IgG1 | −95.03% | |

TABLE 18

Internalization percentages of anti-human Trop-2 antibodies mediated by Trop-2 on the surface of BXPC-3 cells

| | Internalization percentage, 1 h | |
|---|---|---|
| Antibody | Naked | Labeled with SN38 |
| h23-12 | 32.44% | 20.12% |
| ch4-3 | 30.70% | 57.66% |
| ch11-4 | 15.50% | 51.14% |
| Sacituzumab | 37.39% | 32.71% |
| NC-IgG1 | −62.97% | |

Example 16 Detection of Cell Killing Activity of Anti-Trop-2-ADCs

BxPC-3 human pancreatic cancer cells were inoculated at $2 \times 10^3$/well into 96-well cell culture plates, and cultured overnight in an incubator at 37° C., 5% $CO_2$. Afterwards, samples of SN38-labeled anti-Trop-2 antibodies (with each concentration provided in two parallel wells) at different concentrations were added into the plates according to Table 19, and blank wells with cells only (without any treatment) were set. The cells were incubated for 3 h in an incubator at 37° C., 5% $CO_2$ and then culture medium was replaced with fresh complete medium. Next day the treatment was repeated as the previous day; after 4 consecutive days of the treatment, cell killing activity of the SN38-labeled anti-Trop-2 antibodies was detected using Cell Counting Kit-8 (CCK-8).

TABLE 19

Anti-Trop-2-ADCs and actual concentrations thereof

| Name | Actual concentration (µg/ml) | | | | | | | | | | | |
|---|---|---|---|---|---|---|---|---|---|---|---|---|
| h23-12-SN38 | 100 | 33.33 | 11.11 | 3.704 | 1.852 | 0.926 | 0.463 | 0.231 | 0.077 | 0.026 | 0.009 | 0.003 |
| Sacituzumab-SN38 | 100 | 33.33 | 11.11 | 3.704 | 1.852 | 0.926 | 0.463 | 0.231 | 0.077 | 0.026 | 0.009 | 0.003 |
| Tocilizumab-SN38 (negative control ADC) | 100 | 33.33 | 11.11 | 3.704 | 1.852 | 0.926 | 0.463 | 0.231 | 0.077 | 0.026 | 0.009 | 0.003 |
| Ch4-3-SN38 | 100 | 33.33 | 11.11 | 3.704 | 1.852 | 0.926 | 0.463 | 0.231 | 0.077 | 0.026 | 0.009 | 0.003 |
| Ch11-4-SN38 | 100 | 33.33 | 11.11 | 3.704 | 1.852 | 0.926 | 0.463 | 0.231 | 0.077 | 0.026 | 0.009 | 0.003 |

Figure 10:
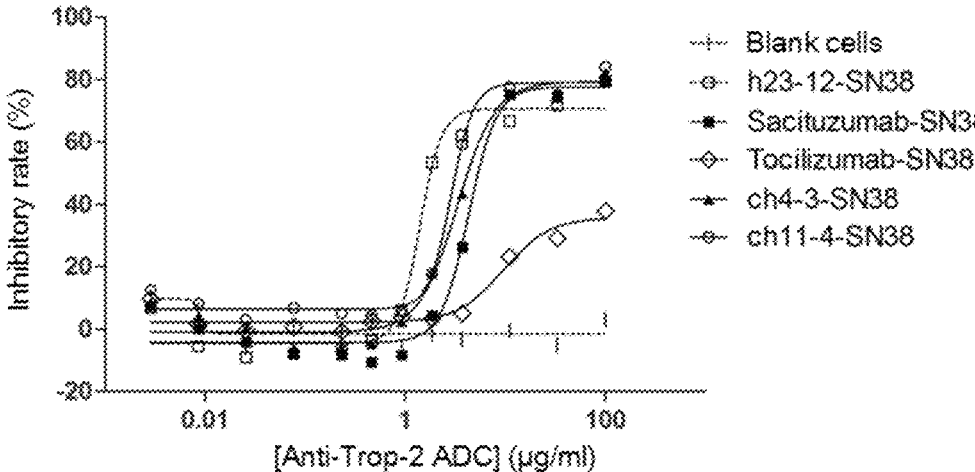
FIG. 10 shows the inhibitory rates of anti-Trop-2-ADCs on cell growth.

The results showed (FIG. 10, and Table 20) that each anti-Trop-2 ADC specifically killed target cells and had no significant difference in killing activity from control antibody Sacituzumab-SN38.

TABLE 20

Inhibitory activity of anti-Trop-2 ADCs on cell growth

| Name | $IC_{50}$ (µg/ml) |
|---|---|
| Blank cells | / |
| h23-12-SN38 | 1.409 |
| Sacituzumab-SN38 | 4.311 |
| ch4-3-SN38 | 3.299 |
| ch11-4-SN38 | 2.879 |

Example 17 Pharmacodynamic Evaluation of Anti-Trop-2-ADCs in N87 Subcutaneous Xenograft Tumor Model Five weeks old female BALB/c nude mice were subcutaneously inoculated with $3 \times 10^6$ human gastric cancer cells (NCI-N87), and randomly grouped with 6 mice per group when tumors grew to around 150 mm³. Grouping as well as administration dosage and frequency for each group are shown in Table 21. Each group was injected intravenously twice a week, and at the same time, tumor volume and body weight of each mouse were measured. When a mouse lost weight more than 15%, or when an animal had a tumor volume exceeding 3000 mm³, or when a whole group of animals had an average tumor volume exceeding 2000 mm³, the experiment was stopped, and the mouse/mice was/were euthanized.

TABLE 21

Grouping as well as administration dosage and frequency for the nude mice

| Group | Drug | Administration dosage | Administration frequency |
|---|---|---|---|
| 1 | h23-12-SN38 | 10 mg/kg | Biw |
| 2 | | 2 mg/kg | Biw |

TABLE 21-continued

Grouping as well as administration dosage and frequency for the nude mice

| Group | Drug | Administration dosage | Administration frequency |
|---|---|---|---|
| 3 | | 0.4 mg/kg | Biw |
| 4 | Sacituzumab-SN38 | 10 mg/kg | Biw |
| 5 | | 2 mg/kg | Biw |
| 6 | ch4-3-SN38 | 10 mg/kg | Biw |
| 7 | | 2 mg/kg | Biw |

TABLE 21-continued

Grouping as well as administration dosage and frequency for the nude mice

| Group | Drug | Administration dosage | Administration frequency |
|---|---|---|---|
| 8 | Negative control, hIgG1 | 10 mg/kg | Biw |
| 9 | Control ADC, hIgG1-SN38 | 10 mg/kg | Biw |

Figure 11:
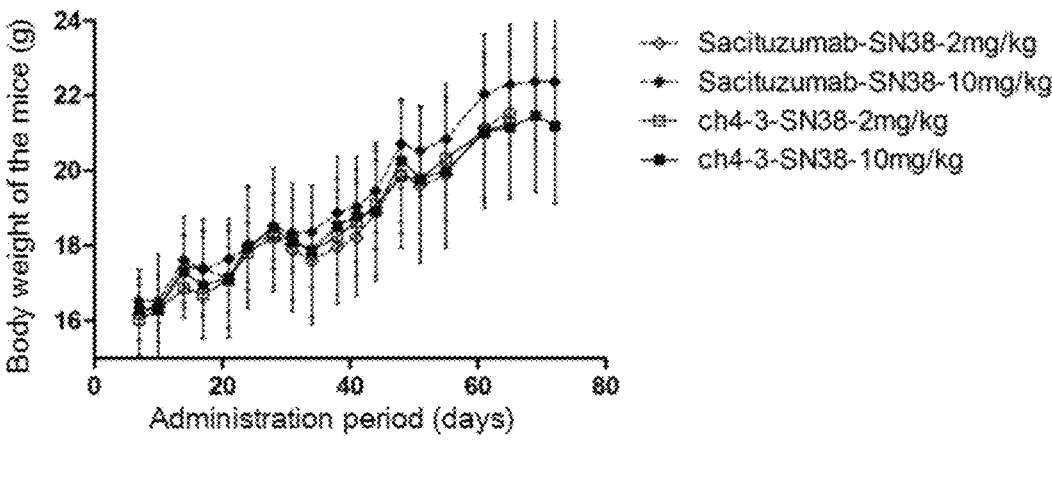
FIG. 11 shows the curves of changes in body weight of BALB/c nu mice bearing tumors in a mouse model of N87 gastric cancer, in which panel 11A: after the administration of ch4-3-SN38; panel 11B: after the administration of h23-12-SN38; panel 11C: after the administration of isotype control antibody; panel 11D: after the high dosage administration of ch4-3-SN38 and h23-12-SN38.
Figure 11:
Figure 11:
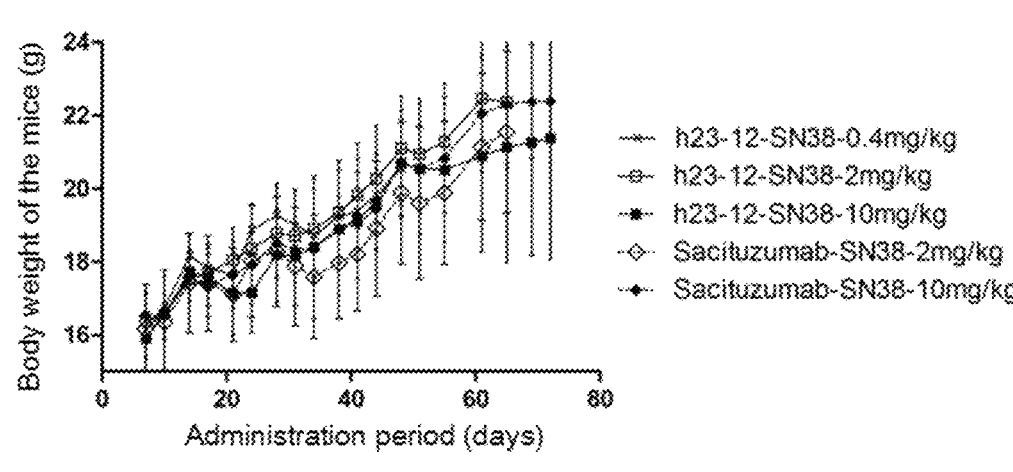

As shown in FIG. 11 and FIG. 12, the anti-Trop-2-ADCs had dose-dependent inhibitory effects on tumor growth, and no difference in efficacy was observed between the ADCs at high dosage (10 mg/kg). No significant toxic effect of the small molecule SN38 in the ADCs was observed, and the body weight of the animals in each experiment group steadily increased without significant difference from controls.

Example 18 Pharmacodynamic Evaluation of Co-Administration of Anti-Trop-2 Antibody and Anti-CD47 Antibody in SKOV3 Subcutaneous Xenograft Tumor Model Five weeks old female BALB/c nude mice were subcutaneously inoculated with $3 \times 10^6$ SKOV3 human ovarian cancer cells into the right flank of each mouse, and randomly grouped with 6 mice per group when tumors grew to around 150 mm³. Grouping as well as administration dosage and frequency for each group are shown in Table 22. Each group was injected intravenously twice a week, 5 times in total, and at the same time, tumor volume and body weight of each mouse were measured. States of the mice were observed, and after the last administration, the mice were euthanized. The anti-CD47 antibody used is described in patent application publication US2015/0183874A1, i.e. humanized 5F9, version 2.

TABLE 22

| | Grouping as well as administration dosage and frequency for the nude mice | | |
| --- | --- | --- | --- |
| Group | Drug | Administration dosage | Administration frequency |
| 1 | anti-CD47 antibody | 10 mg/kg | Biw |
| 2 | h23-12 | 2 mg/kg | Biw |
| 3 | h23-12 + anti-CD47 antibody | 2 mg/kg + 10 mg/kg | Biw |
| 4 | Negative control hIgG4 | 2 mg/kg | Biw |

Figure 13:
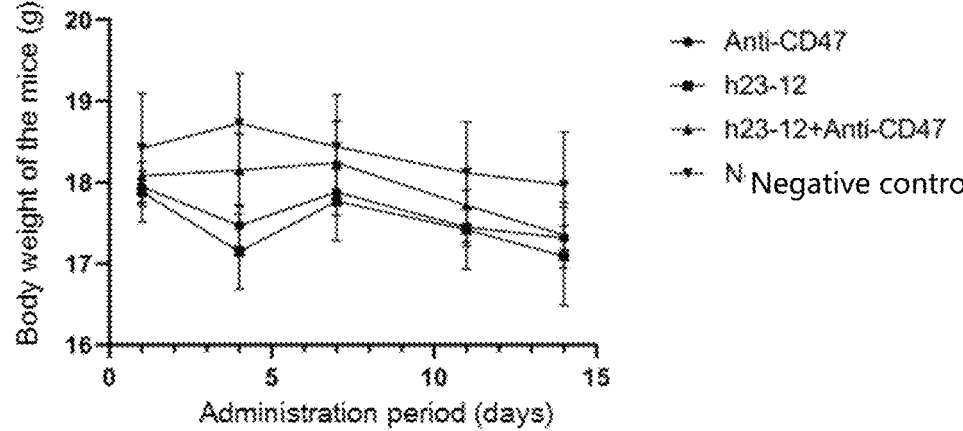
FIG. 13 shows the curves of changes in body weight of mice in SKOV3 subcutaneous xenograft mouse model with the co-administration of anti-Trop-2 antibody and anti-CD47 antibody.
Figure 14:
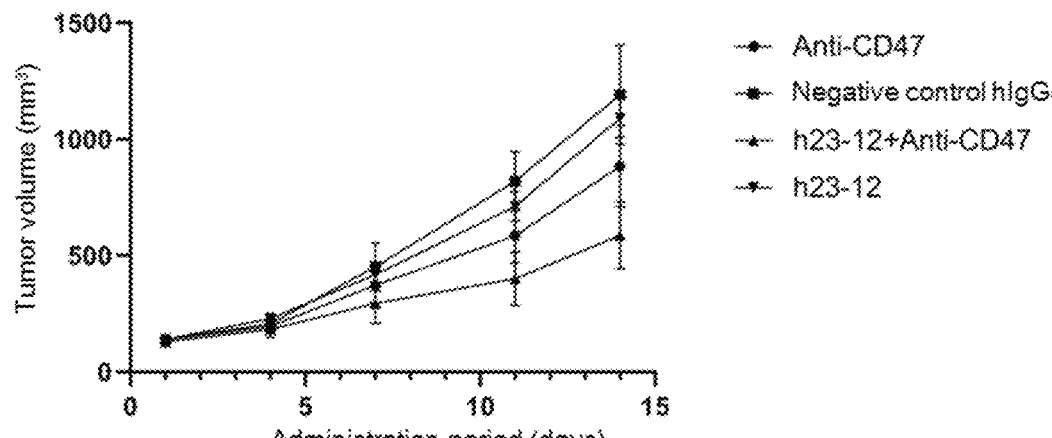
FIG. 14 shows the curves of changes in tumor volume of mice in SKOV3 subcutaneous xenograft mouse model with the co-administration of anti-Trop-2 antibody and anti-CD47 antibody.

As shown in FIG. 13 and FIG. 14, the co-administration group of h23-12+anti-CD47 antibody showed a certain inhibitory activity on tumor compared with the negative control hIgG4, and the group of anti-CD47 antibody and group of h23-12 showed no significant inhibitory effects on tumor. Therefore, it can be seen the anti-Trop-2 antibody of the present disclosure and the anti-CD47 antibody can synergistically promote phagocytosis of tumor cells by macrophages, and have a synergistic inhibitory effect on tumor.

Example 19 Pharmacodynamic Evaluation of Anti-Trop-2-ADCs in N87 Subcutaneous Xenograft Tumor Model Five weeks old female BALB/c nude mice were subcutaneously inoculated with $3 \times 10^6$ human gastric cancer cells (NCI-N87), and randomly grouped with 6 mice per group when tumors grew to around 100 mm³. Grouping as well as administration dosage and frequency for each group are shown in Table 23. Each group was injected intravenously twice a week, and at the same time, tumor volume and body weight of each mouse were measured. When a mouse lost weight more than 15%, or when an animal had a tumor volume exceeding 3000 mm³, or when a whole group of animals had an average tumor volume exceeding 2000 mm³, the experiment was stopped, and the mouse/mice was/were euthanized.

TABLE 23

| | Grouping as well as administration dosage and frequency for the nude mice | | |
| --- | --- | --- | --- |
| Group | Drug | Administration dosage | Administration frequency |
| 1 | ch3-11-SN38 | 5 mg/kg | Biw × 6 |
| 2 | ch11-4-SN38 | 5 mg/kg | Biw × 6 |
| 3 | Sacituzumab-SN38 | 5 mg/kg | Biw × 6 |
| 4 | Negative control, hIgG1 | 5 mg/kg | Biw × 6 |
| 5 | Control ADC, hIgG1-SN38 | 5 mg/kg | Biw × 6 |

Figure 15:
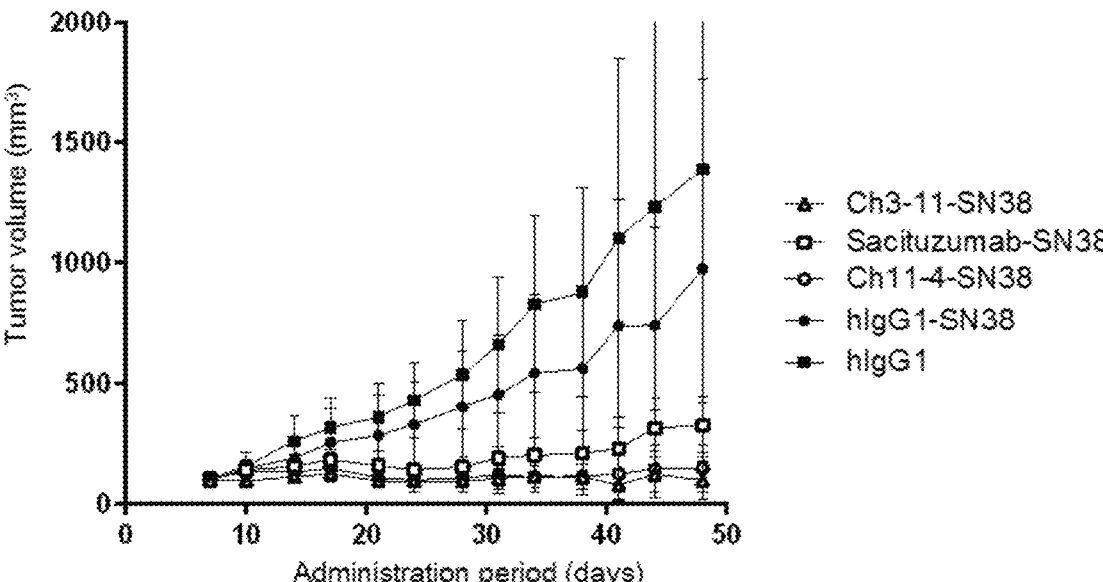
FIG. 15 shows the curves of changes in tumor volume of BALB/c nu mice bearing tumors in a subcutaneous xenograft mouse model of NCI-N87 gastric cancer.
Figure 16:
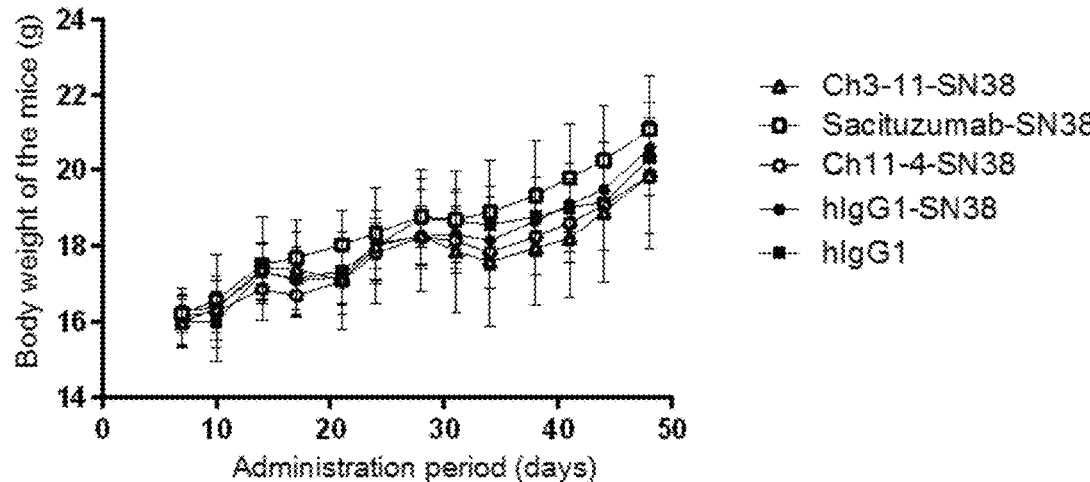
FIG. 16 shows the curves of changes in body weight of BALB/c nu mice bearing tumors in a subcutaneous xenograft mouse model of NCI-N87 gastric cancer.

As shown in FIG. 15 and FIG. 16, the anti-Trop-2-ADCs had dose-dependent inhibitory effects on tumor growth, and ADCs ch3-11-SN38 and ch11-4-SN38 at dosage of 5 mg/kg had a slight better efficacy than Sacituzumab-SN38; and no significant toxic effect of the small molecule SN38 in the ADCs was observed.

The above description of the embodiments of the present invention is not intended to limit the present invention, and those skilled in the art may make various changes and modifications to the present invention without departing from the spirit of the present invention, which should fall within the scope of the appended claims.

What is claimed is:

1. An anti-Trop-2 antibody or fragment thereof comprising a heavy chain variable region (VH) and a light chain variable region (VL), wherein the heavy chain variable region (VH) and the light chain variable region (VL) comprise a combination of CDRs (HCDR1, HCDR2, HCDR3; and LCDR1, LCDR2, LCDR3) wherein:
   the heavy chain variable region comprises HCDR1 having the amino acid sequence as shown in SEQ ID NO: 65, HCDR2 having the amino acid sequence as shown in SEQ ID NO: 72, and HCDR3 having the amino acid sequence as shown in SEQ ID NO: 81; and
   the light chain variable region comprises LCDR1 having the amino acid sequence as shown in SEQ ID NO: 91, LCDR2 having the amino acid sequence as shown in SEQ ID NO: 99, and LCDR3 having the amino acid sequence as shown in SEQ ID NO: 105.

2. The antibody or fragment thereof according to claim 1, wherein the heavy chain variable region comprises the amino acid sequence as shown in SEQ ID NO: 14 and the light chain variable region comprises the amino acid sequence as shown in SEQ ID NO: 33.

3. The antibody or fragment thereof according to claim 2, wherein the antibody or fragment thereof is a monoclonal antibody, a single chain antibody, a diabody, a fully or partially humanized antibody, or a chimeric antibody; alternatively, the antibody or fragment thereof is scFv, BsFv, dsFv, (dsFv)₂, Fab, Fab', F(ab')₂, or Fv.

4. The antibody or fragment thereof according to claim 3, wherein the antibody is a murine, chimeric, or humanized monoclonal antibody.

5. An isolated nucleic acid molecule comprising a nucleotide sequence encoding the antibody or fragment thereof according to claim 1.

6. An isolated vector comprising the nucleic acid molecule according to claim 5.

7. An isolated host cell comprising the nucleic acid molecule according to claim 5, or transformed or transfected with the nucleic acid molecule.

8. A pharmaceutical composition comprising the antibody or fragment thereof according to claim 1, and optionally a pharmaceutically acceptable excipient.

9. The pharmaceutical composition according to claim 8, wherein the pharmaceutical composition comprises a further antibody-based drug.

10. A kit comprising the antibody or fragment thereof according to claim 1.

11. A fusion protein comprising the antibody or fragment thereof according to claim 1.

12. A conjugate comprising the antibody or fragment thereof according to claim 1 and a drug conjugated thereto, wherein the drug is a cytotoxic agent.

13. The conjugate according to claim 12, wherein the conjugate is an antibody drug conjugate (ADC) represented by the formula: (the antibody or fragment thereof)-(linker)-(a cytotoxic agent).

14. A method for manufacturing an antibody drug conjugate (ADC) comprising conjugating the antibody or fragment thereof according to claim 1 to a cytotoxic agent via a linker.

15. A method for preventing and/or treating a disease, including administering to a subject in need thereof the antibody or fragment thereof according to claim 1 or the conjugate according to claim 12, and optionally other drug, wherein the disease is selected from among gastric cancer, pancreatic cancer, intestinal cancer, ovarian cancer, squamous lung cancer, non-small cell lung cancer, small cell lung cancer, urothelial cancer, triple negative breast cancer, or cervical cancer.

16. The antibody or fragment thereof according to claim 4, wherein the heavy chain constant region of the monoclonal antibody is of IgG1 or IgG4 subtype and the light chain constant region of the monoclonal antibody is of kappa type.

17. The pharmaceutical composition according to claim 9, wherein the further antibody-based drug is an antibody against macrophage-related immune checkpoint.

18. The pharmaceutical composition according to claim 9, wherein the further antibody-based drug is an anti-CD47 antibody.

19. The conjugate according to claim 13, wherein the cytotoxic agent is a tubulin inhibitor or a DNA replication inhibitor.

20. The conjugate according to claim 19, wherein the tubulin inhibitor is paclitaxel or docetaxel; and the DNA replication inhibitor is irinotecan or its active metabolite SN-38.

21. The method according to claim 14, wherein the cytotoxic agent is a tubulin inhibitor or a DNA replication inhibitor.

22. The antibody or fragment thereof according to claim 1, wherein the heavy chain variable region comprises an amino acid sequence having at least 90% identity to the amino acid sequence as shown in SEQ ID NO: 14 and the light chain variable region comprises an amino acid sequence having at least 90% identity to the amino acid sequence as shown in SEQ ID NO: 33.

23. A method for treating a disease, including administering to a subject in need thereof the antibody or fragment thereof according to claim 1, and optionally other drug, wherein the disease is selected from among gastric cancer, pancreatic cancer, intestinal cancer, ovarian cancer, squamous lung cancer, non-small cell lung cancer, small cell lung cancer, urothelial cancer, triple negative breast cancer, or cervical cancer.

\* \* \* \* \*

SEQUENCE LISTING

```
<160> NUMBER OF SEQ ID NOS: 60

<210> SEQ ID NO 1
<211> LENGTH: 123
<212> TYPE: PRT
<213> ORGANISM: Artificial
<220> FEATURE:
<223> OTHER INFORMATION: heavy chain variable region

<400> SEQUENCE: 1

Gln Val Gln Leu Gln Gln Pro Gly Ala Glu Leu Val Lys Pro Gly Ser
1               5                   10                  15

Ser Val Lys Leu Ser Cys Lys Ala Ser Gly Tyr Thr Phe Thr Ser Tyr
            20                  25                  30

Trp Met Tyr Trp Val Lys Gln Arg Pro Gly Gln Gly Leu Glu Trp Ile
        35                  40                  45

Gly Glu Ile Asn Pro Ser Asn Gly Arg Thr Asn Tyr Asn Glu Lys Phe
    50                  55                  60

Lys Ser Lys Ala Thr Leu Thr Val Asp Lys Ser Ser Ser Thr Ala Tyr
65                  70                  75                  80

Met Gln Phe Ser Ser Leu Thr Ser Glu Asp Ser Ala Val Tyr Tyr Cys
                85                  90                  95

Thr Arg Glu Gly His Asn Tyr Asp Gly Ser Leu Gly Ala Met Asp His
            100                 105                 110

Trp Gly Gln Gly Thr Ser Val Thr Val Ser Ser
            115                 120
```

```
<210> SEQ ID NO 2
<211> LENGTH: 117
<212> TYPE: PRT
<213> ORGANISM: Artificial
<220> FEATURE:
<223> OTHER INFORMATION: heavy chain variable region

<400> SEQUENCE: 2

Gln Val Gln Leu Gln Gln Ser Gly Pro Glu Leu Val Lys Pro Gly Ala
1               5                   10                  15

Ser Val Lys Met Ser Cys Lys Ala Ser Gly Phe Thr Phe Thr Asp Tyr
            20                  25                  30

Val Ile Gly Trp Val Lys Gln Arg Thr Gly Gln Gly Leu Glu Trp Ile
        35                  40                  45

Gly Glu Ile Tyr Leu Gly Ser Gly Thr Ile Tyr Tyr Thr Glu Lys Phe
    50                  55                  60

Lys Gly Lys Ala Thr Leu Thr Ala Asp Thr Ser Ser Asn Thr Ala Tyr
65                  70                  75                  80

Met Gln Leu Ser Ser Leu Thr Ser Glu Asp Ser Ala Val Tyr Phe Cys
                85                  90                  95

Ala Arg Gly Ser Ile Phe Pro Phe Asp Tyr Trp Gly Gln Gly Thr Thr
            100                 105                 110

Leu Thr Val Ser Ser
        115

<210> SEQ ID NO 3
<211> LENGTH: 117
<212> TYPE: PRT
<213> ORGANISM: Artificial
<220> FEATURE:
<223> OTHER INFORMATION: heavy chain variable region

<400> SEQUENCE: 3

Glu Val Gln Leu Val Gln Ser Gly Pro Glu Val Lys Lys Pro Gly Ala
1               5                   10                  15

Ser Val Lys Val Ser Cys Lys Ala Ser Gly Phe Thr Phe Thr Asp Tyr
            20                  25                  30

Val Ile Gly Trp Val Arg Gln Ala Pro Gly Gln Gly Leu Glu Trp Ile
        35                  40                  45

Gly Glu Ile Tyr Leu Gly Ser Gly Thr Ile Tyr Tyr Thr Glu Lys Phe
    50                  55                  60

Lys Gly Arg Val Thr Met Thr Ala Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Ser Ile Phe Pro Phe Asp Tyr Trp Gly Gln Gly Thr Leu
            100                 105                 110

Val Thr Val Ser Ser
        115

<210> SEQ ID NO 4
<211> LENGTH: 117
<212> TYPE: PRT
<213> ORGANISM: Artificial
<220> FEATURE:
<223> OTHER INFORMATION: heavy chain variable region

<400> SEQUENCE: 4

Glu Val Gln Leu Val Gln Ser Gly Pro Glu Val Lys Lys Pro Gly Ala
1               5                   10                  15
```

-continued

```
Ser Val Lys Val Ser Cys Lys Ala Ser Gly Phe Thr Phe Thr Asp Tyr
            20                  25                  30

Val Ile Gly Trp Val Arg Gln Ala Pro Gly Gln Gly Leu Glu Trp Ile
            35                  40                  45

Gly Glu Ile Tyr Leu Gly Ser Gly Thr Ile Tyr Tyr Ala Glu Lys Phe
    50                  55                  60

Lys Gly Arg Val Thr Met Thr Ala Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Ser Ile Phe Pro Phe Asp Tyr Trp Gly Gln Gly Thr Leu
            100                 105                 110

Val Thr Val Ser Ser
            115

<210> SEQ ID NO 5
<211> LENGTH: 117
<212> TYPE: PRT
<213> ORGANISM: Artificial
<220> FEATURE:
<223> OTHER INFORMATION: heavy chain variable region

<400> SEQUENCE: 5

Gln Val Gln Leu Gln Gln Pro Gly Ala Glu Leu Val Arg Pro Gly Ala
1               5                   10                  15

Ser Val Asn Leu Ser Cys Lys Ala Ser Gly Tyr Thr Phe Thr Ser Tyr
            20                  25                  30

Trp Ile Asn Trp Val Lys Gln Arg Pro Gly Gln Gly Leu Glu Trp Ile
            35                  40                  45

Gly Asn Ile Tyr Pro Ser Asn Ser Tyr Thr Asn Tyr Asn Gln Lys Phe
    50                  55                  60

Lys Asp Thr Ala Thr Leu Thr Val Asp Lys Ser Ser Ser Thr Ala Tyr
65                  70                  75                  80

Met Gln Leu Ser Ser Pro Thr Ser Glu Asp Ser Ala Val Tyr Phe Cys
                85                  90                  95

Ser Ser Tyr Arg Ser Asp Gly Phe Ala Tyr Trp Gly Gln Gly Thr Leu
            100                 105                 110

Val Thr Val Ser Ala
            115

<210> SEQ ID NO 6
<211> LENGTH: 117
<212> TYPE: PRT
<213> ORGANISM: Artificial
<220> FEATURE:
<223> OTHER INFORMATION: heavy chain variable region

<400> SEQUENCE: 6

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Ile Asn Trp Val Arg Gln Ala Pro Gly Gln Gly Leu Glu Trp Met
            35                  40                  45

Gly Asn Ile Tyr Pro Ser Asn Ser Tyr Thr Asn Tyr Asn Gln Lys Phe
    50                  55                  60

Lys Asp Arg Val Thr Met Thr Arg Asp Thr Ser Thr Ser Thr Val Tyr
```

```
65                  70                  75                  80

Met Glu Leu Ser Ser Leu Arg Ser Glu Asp Thr Ala Val Tyr Tyr Cys
                85                  90                  95

Ala Arg Tyr Arg Ser Asp Gly Phe Ala Tyr Trp Gly Gln Gly Thr Leu
               100                 105                 110

Val Thr Val Ser Ser
               115

<210> SEQ ID NO 7
<211> LENGTH: 117
<212> TYPE: PRT
<213> ORGANISM: Artificial
<220> FEATURE:
<223> OTHER INFORMATION: heavy chain variable region

<400> SEQUENCE: 7

Glu Val Gln Leu Val Gln Ser Gly Ala Glu Val Lys Lys Pro Gly Ala
1                5                  10                  15

Ser Val Lys Val Ser Cys Lys Ala Ser Gly Tyr Thr Phe Thr Ser Tyr
               20                  25                  30

Trp Ile Asn Trp Val Arg Gln Ala Pro Gly Gln Gly Leu Glu Trp Met
              35                  40                  45

Gly Asn Ile Tyr Pro Ser Asn Ser Tyr Thr Asn Tyr Asn Gln Lys Phe
     50                  55                  60

Lys Asp Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ser Ser Tyr Arg Ser Asp Gly Phe Ala Tyr Trp Gly Gln Gly Thr Leu
               100                 105                 110

Val Thr Val Ser Ser
               115

<210> SEQ ID NO 8
<211> LENGTH: 117
<212> TYPE: PRT
<213> ORGANISM: Artificial
<220> FEATURE:
<223> OTHER INFORMATION: heavy chain variable region

<400> SEQUENCE: 8

Glu Val Gln Leu Val Gln Ser Gly Ala Glu Val Lys Lys Pro Gly Ala
1                5                  10                  15

Ser Val Lys Val Ser Cys Lys Ala Ser Gly Tyr Thr Phe Thr Ser Tyr
               20                  25                  30

Trp Ile Asn Trp Val Arg Gln Ala Pro Gly Gln Gly Leu Glu Trp Met
              35                  40                  45

Gly Asn Ile Tyr Pro Ser Asn Ser Tyr Thr Asn Tyr Asn Gln Lys Phe
     50                  55                  60

Lys Asp Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ser Ser Tyr Arg Ser Glu Gly Phe Ala Tyr Trp Gly Gln Gly Thr Leu
               100                 105                 110

Val Thr Val Ser Ser
               115
```

-continued

```
<210> SEQ ID NO 9
<211> LENGTH: 117
<212> TYPE: PRT
<213> ORGANISM: Artificial
<220> FEATURE:
<223> OTHER INFORMATION: heavy chain variable region

<400> SEQUENCE: 9

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Ile Asn Trp Val Arg Gln Ala Pro Gly Gln Gly Leu Glu Trp Met
        35                  40                  45

Gly Asn Ile Tyr Pro Ser Asn Ser Tyr Thr Asn Tyr Asn Gln Lys Phe
    50                  55                  60

Lys Asp Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ser Ser Tyr Arg Ser Gly Gly Phe Ala Tyr Trp Gly Gln Gly Thr Leu
            100                 105                 110

Val Thr Val Ser Ser
        115

<210> SEQ ID NO 10
<211> LENGTH: 117
<212> TYPE: PRT
<213> ORGANISM: Artificial
<220> FEATURE:
<223> OTHER INFORMATION: heavy chain variable region

<400> SEQUENCE: 10

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Ile Asn Trp Val Arg Gln Ala Pro Gly Gln Gly Leu Glu Trp Met
        35                  40                  45

Gly Asn Ile Tyr Pro Ser Asn Ser Tyr Thr Asn Tyr Asn Gln Lys Phe
    50                  55                  60

Lys Asp Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ser Ser Tyr Arg Ser Asp Ala Phe Ala Tyr Trp Gly Gln Gly Thr Leu
            100                 105                 110

Val Thr Val Ser Ser
        115

<210> SEQ ID NO 11
<211> LENGTH: 115
<212> TYPE: PRT
<213> ORGANISM: Artificial
<220> FEATURE:
<223> OTHER INFORMATION: heavy chain variable region

<400> SEQUENCE: 11

Glu Val Lys Leu Val Glu Ser Gly Gly Val Leu Val Lys Pro Gly Gly
```

```
1               5                   10                  15
Ser Leu Lys Leu Ser Cys Ala Ala Ser Gly Phe Thr Phe Ser Asp Ser
            20                  25                  30

Ala Met Ser Trp Val Arg Gln Thr Pro Glu Lys Arg Leu Glu Trp Val
            35                  40                  45

Ala Ser Ile Ser Arg Gly Asp Asp Thr Tyr Tyr Pro Asp Ser Val Lys
    50                  55                  60

Gly Arg Ile Thr Ile Ser Arg Asp Phe Ala Arg Asn Ile Leu Tyr Leu
65                  70                  75                  80

Gln Met Thr Ser Leu Arg Ser Glu Asp Thr Ala Met Tyr Tyr Cys Thr
                85                  90                  95

Arg Asp Arg Phe Gly Phe Ala Tyr Trp Gly Gln Gly Thr Leu Val Thr
            100                 105                 110

Val Ser Ala
        115
```

<210> SEQ ID NO 12
<211> LENGTH: 119
<212> TYPE: PRT
<213> ORGANISM: Artificial
<220> FEATURE:
<223> OTHER INFORMATION: heavy chain variable region

<400> SEQUENCE: 12

```
Gln Val Gln Leu Gln Gln Pro Gly Ala Glu Leu Val Lys Pro Gly Ala
1               5                   10                  15

Ser Val Lys Leu Ser Cys Lys Ala Asp Gly Tyr Ile Phe Thr Ser Tyr
            20                  25                  30

Trp Met His Trp Val Lys Gln Arg Pro Gly Gln Gly Leu Glu Trp Ile
        35                  40                  45

Gly Glu Ile Thr Pro Ser Asp Asn Tyr Thr Ser Tyr Asn Gln Lys Phe
    50                  55                  60

Lys Gly Lys Ala Thr Leu Thr Val Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Thr Arg Gly His Gly Asn Tyr Val Ser Phe Asp Tyr Trp Gly Gln Gly
            100                 105                 110

Thr Thr Leu Thr Val Ser Ser
        115
```

<210> SEQ ID NO 13
<211> LENGTH: 119
<212> TYPE: PRT
<213> ORGANISM: Artificial
<220> FEATURE:
<223> OTHER INFORMATION: heavy chain variable region

<400> SEQUENCE: 13

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Met His Trp Val Arg Gln Ala Pro Gly Gln Gly Leu Glu Trp Met
        35                  40                  45

Gly Glu Ile Thr Pro Ser Asp Asn Tyr Thr Ser Tyr Asn Gln Lys Phe
    50                  55                  60
```

```
Lys Gly Arg Val Thr Ile Thr Arg Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly His Gly Asn Tyr Val Ser Phe Asp Tyr Trp Gly Gln Gly
            100                 105                 110

Thr Leu Val Thr Val Ser Ser
            115

<210> SEQ ID NO 14
<211> LENGTH: 119
<212> TYPE: PRT
<213> ORGANISM: Artificial
<220> FEATURE:
<223> OTHER INFORMATION: heavy chain variable region

<400> SEQUENCE: 14

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Trp Met His Trp Val Arg Gln Ala Pro Gly Gln Gly Leu Glu Trp Met
            35                  40                  45

Gly Glu Ile Thr Pro Ser Asp Asn Tyr Gly Ser Tyr Asn Gln Lys Phe
        50                  55                  60

Lys Gly Arg Val Thr Ile Thr Arg Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly His Gly Asn Tyr Val Ser Phe Asp Tyr Trp Gly Gln Gly
            100                 105                 110

Thr Leu Val Thr Val Ser Ser
            115

<210> SEQ ID NO 15
<211> LENGTH: 119
<212> TYPE: PRT
<213> ORGANISM: Artificial
<220> FEATURE:
<223> OTHER INFORMATION: heavy chain variable region

<400> SEQUENCE: 15

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Trp Met His Trp Val Arg Gln Ala Pro Gly Gln Gly Leu Glu Trp Met
            35                  40                  45

Gly Glu Ile Thr Pro Gly Asp Asn Tyr Thr Ser Tyr Asn Gln Lys Phe
        50                  55                  60

Lys Gly Arg Val Thr Ile Thr Arg Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly His Gly Asn Tyr Val Ser Phe Asp Tyr Trp Gly Gln Gly
            100                 105                 110

Thr Leu Val Thr Val Ser Ser
            115
```

-continued

```
<210> SEQ ID NO 16
<211> LENGTH: 119
<212> TYPE: PRT
<213> ORGANISM: Artificial
<220> FEATURE:
<223> OTHER INFORMATION: heavy chain variable region

<400> SEQUENCE: 16

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Met His Trp Val Arg Gln Ala Pro Gly Gln Gly Leu Glu Trp Met
        35                  40                  45

Gly Glu Ile Thr Pro Ser Asp Asn Tyr Thr Ser Tyr Asn Gln Lys Phe
    50                  55                  60

Lys Gly Arg Val Thr Ile Thr Arg Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Glu Gly Asn Tyr Val Ser Phe Asp Tyr Trp Gly Gln Gly
            100                 105                 110

Thr Leu Val Thr Val Ser Ser
        115

<210> SEQ ID NO 17
<211> LENGTH: 119
<212> TYPE: PRT
<213> ORGANISM: Artificial
<220> FEATURE:
<223> OTHER INFORMATION: heavy chain variable region

<400> SEQUENCE: 17

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Met His Trp Val Arg Gln Ala Pro Gly Gln Gly Leu Glu Trp Met
        35                  40                  45

Gly Glu Ile Thr Pro Ser Asp Asn Tyr Thr Ser Tyr Asn Gln Lys Phe
    50                  55                  60

Lys Gly Arg Val Thr Ile Thr Arg Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gln Gly Asn Tyr Val Ser Phe Asp Tyr Trp Gly Gln Gly
            100                 105                 110

Thr Leu Val Thr Val Ser Ser
        115

<210> SEQ ID NO 18
<211> LENGTH: 112
<212> TYPE: PRT
<213> ORGANISM: Artificial
<220> FEATURE:
<223> OTHER INFORMATION: light chain variable region

<400> SEQUENCE: 18
```

-continued

```
Asp Val Val Val Thr Gln Thr Pro Leu Ser Leu Pro Val Ser Phe Gly
1               5                   10                  15

Asp Gln Val Ser Ile Ser Cys Arg Ser Ser Gln Ser Leu Thr Asn Ser
            20                  25                  30

Tyr Gly Asn Thr Phe Leu Ser Trp Tyr Leu His Lys Pro Gly Gln Ser
        35                  40                  45

Pro Gln Leu Leu Leu Tyr Gly Ile Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Asn Thr Ile Lys Pro Glu Asp Leu Gly Met Tyr Tyr Cys Phe Gln Ser
                85                  90                  95

Thr His Gln Pro Tyr Thr Phe Gly Gly Gly Thr Lys Leu Glu Ile Lys
            100                 105                 110
```

```
<210> SEQ ID NO 19
<211> LENGTH: 106
<212> TYPE: PRT
<213> ORGANISM: Artificial
<220> FEATURE:
<223> OTHER INFORMATION: light chain variable region

<400> SEQUENCE: 19

Gln Ile Val Leu Thr Gln Ser Pro Ala Ile Met Ser Ala Ser Pro Gly
1               5                   10                  15

Glu Lys Val Thr Met Thr Cys Ser Ala Ser Ser Ser Val Ser Tyr Met
            20                  25                  30

Tyr Trp Tyr Gln Gln Lys Pro Gly Ser Ser Pro Arg Leu Leu Ile Tyr
        35                  40                  45

Asp Thr Ser Thr Leu Ala Ser Gly Val Pro Val Arg Phe Ser Gly Ser
    50                  55                  60

Gly Ser Gly Thr Ser Tyr Ser Leu Thr Ile Ser Arg Met Glu Ala Glu
65                  70                  75                  80

Asp Ala Ala Thr Tyr Tyr Cys Gln Gln Trp Ser Ser Tyr Pro Tyr Thr
                85                  90                  95

Phe Gly Gly Gly Thr Lys Leu Glu Ile Lys
            100                 105
```

```
<210> SEQ ID NO 20
<211> LENGTH: 106
<212> TYPE: PRT
<213> ORGANISM: Artificial
<220> FEATURE:
<223> OTHER INFORMATION: light chain variable region

<400> SEQUENCE: 20

Asp Ile Gln Leu Thr Gln Ser Pro Ser Ser Leu Ser Ala Ser Val Gly
1               5                   10                  15

Asp Arg Val Thr Ile Thr Cys Ser Ala Ser Ser Ser Val Ser Tyr Met
            20                  25                  30

Tyr Trp Tyr Gln Gln Lys Pro Gly Lys Ala Pro Lys Leu Leu Ile Tyr
        35                  40                  45

Asp Thr Ser Thr Leu Ala Ser Gly Val Pro Ser Arg Phe Ser Gly Ser
    50                  55                  60

Gly Ser Gly Thr Asp Phe Thr Leu Thr Ile Ser Ser Leu Gln Pro Glu
65                  70                  75                  80

Asp Phe Ala Thr Tyr Tyr Cys Gln Gln Trp Ser Ser Tyr Pro Tyr Thr
                85                  90                  95
```

```
Phe Gly Gln Gly Thr Lys Leu Glu Ile Lys
            100                 105

<210> SEQ ID NO 21
<211> LENGTH: 106
<212> TYPE: PRT
<213> ORGANISM: Artificial
<220> FEATURE:
<223> OTHER INFORMATION: light chain variable region

<400> SEQUENCE: 21

Asp Ile Gln Leu Thr Gln Ser Pro Ser Ser Leu Ser Ala Ser Val Gly
1               5                   10                  15

Asp Arg Val Thr Ile Thr Cys Arg Ala Ser Ser Ser Val Ser Tyr Met
            20                  25                  30

Tyr Trp Tyr Gln Gln Lys Pro Gly Lys Ala Pro Lys Leu Leu Ile Tyr
        35                  40                  45

Asp Thr Ser Thr Leu Ala Ser Gly Val Pro Ser Arg Phe Ser Gly Ser
    50                  55                  60

Gly Ser Gly Thr Asp Phe Thr Leu Thr Ile Ser Ser Leu Gln Pro Glu
65                  70                  75                  80

Asp Phe Ala Thr Tyr Tyr Cys Gln Gln Trp Ser Ser Tyr Pro Tyr Thr
                85                  90                  95

Phe Gly Gln Gly Thr Lys Leu Glu Ile Lys
            100                 105

<210> SEQ ID NO 22
<211> LENGTH: 106
<212> TYPE: PRT
<213> ORGANISM: Artificial
<220> FEATURE:
<223> OTHER INFORMATION: light chain variable region

<400> SEQUENCE: 22

Asp Ile Gln Leu Thr Gln Ser Pro Ser Ser Leu Ser Ala Ser Val Gly
1               5                   10                  15

Asp Arg Val Thr Ile Thr Cys Ser Ala Ser Ser Ser Val Ser Tyr Met
            20                  25                  30

Tyr Trp Tyr Gln Gln Lys Pro Gly Lys Ala Pro Lys Leu Leu Ile Tyr
        35                  40                  45

Asp Ala Ser Thr Leu Ala Ser Gly Val Pro Ser Arg Phe Ser Gly Ser
    50                  55                  60

Gly Ser Gly Thr Asp Phe Thr Leu Thr Ile Ser Ser Leu Gln Pro Glu
65                  70                  75                  80

Asp Phe Ala Thr Tyr Tyr Cys Gln Gln Trp Ser Ser Tyr Pro Tyr Thr
                85                  90                  95

Phe Gly Gln Gly Thr Lys Leu Glu Ile Lys
            100                 105

<210> SEQ ID NO 23
<211> LENGTH: 106
<212> TYPE: PRT
<213> ORGANISM: Artificial
<220> FEATURE:
<223> OTHER INFORMATION: light chain variable region

<400> SEQUENCE: 23

Asp Ile Gln Leu Thr Gln Ser Pro Ser Ser Leu Ser Ala Ser Val Gly
1               5                   10                  15
```

```
Asp Arg Val Thr Ile Thr Cys Ser Ala Ser Ser Ser Val Ser Tyr Met
            20                  25                  30

Tyr Trp Tyr Gln Gln Lys Pro Gly Lys Ala Pro Lys Leu Leu Ile Tyr
        35                  40                  45

Asp Thr Ser Thr Leu Gln Ser Gly Val Pro Ser Arg Phe Ser Gly Ser
    50                  55                  60

Gly Ser Gly Thr Asp Phe Thr Leu Thr Ile Ser Ser Leu Gln Pro Glu
65                  70                  75                  80

Asp Phe Ala Thr Tyr Tyr Cys Gln Gln Trp Ser Ser Tyr Pro Tyr Thr
                85                  90                  95

Phe Gly Gln Gly Thr Lys Leu Glu Ile Lys
            100                 105

<210> SEQ ID NO 24
<211> LENGTH: 107
<212> TYPE: PRT
<213> ORGANISM: Artificial
<220> FEATURE:
<223> OTHER INFORMATION: light chain variable region

<400> SEQUENCE: 24

Asp Ile Leu Leu Thr Gln Ser Pro Ala Ile Leu Ser Val Ser Pro Gly
1               5                   10                  15

Glu Lys Val Ser Phe Ser Cys Arg Ala Ser Gln Asn Ile Gly Thr Ser
            20                  25                  30

Ile His Trp Tyr Gln Gln Arg Thr Asn Gly Ser Pro Arg Leu Leu Ile
        35                  40                  45

Glu Phe Ala Ser Glu Ser Ile Ser Gly Ile Pro Ser Arg Phe Ser Gly
    50                  55                  60

Ser Gly Ser Gly Thr Asp Phe Thr Leu Thr Ile Asn Ser Val Glu Ser
65                  70                  75                  80

Glu Asp Ile Ala Asp Tyr Tyr Cys Gln Gln Ser Asn Ser Trp Pro Phe
                85                  90                  95

Thr Phe Gly Gly Gly Thr Lys Leu Glu Ile Lys
            100                 105

<210> SEQ ID NO 25
<211> LENGTH: 107
<212> TYPE: PRT
<213> ORGANISM: Artificial
<220> FEATURE:
<223> OTHER INFORMATION: light chain variable region

<400> SEQUENCE: 25

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Asn Ile Gly Thr Ser
            20                  25                  30

Ile His Trp Tyr Gln Gln Lys Pro Gly Gln Ala Pro Arg Leu Leu Ile
        35                  40                  45

Tyr Phe Ala Ser Glu Ser Ile Ser Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Ser Asn Ser Trp Pro Phe
                85                  90                  95

Thr Phe Gly Gly Gly Thr Lys Val Glu Ile Lys
            100                 105
```

-continued

```
<210> SEQ ID NO 26
<211> LENGTH: 107
<212> TYPE: PRT
<213> ORGANISM: Artificial
<220> FEATURE:
<223> OTHER INFORMATION: light chain variable region

<400> SEQUENCE: 26

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Asn Ile Gly Thr Ser
            20                  25                  30

Ile His Trp Tyr Gln Gln Lys Pro Gly Gln Ala Pro Arg Leu Leu Ile
        35                  40                  45

Glu Phe Ala Ser Glu Ser Ile Ser Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Ser Asn Ser Trp Pro Phe
                85                  90                  95

Thr Phe Gly Gly Gly Thr Lys Val Glu Ile Lys
            100                 105

<210> SEQ ID NO 27
<211> LENGTH: 107
<212> TYPE: PRT
<213> ORGANISM: Artificial
<220> FEATURE:
<223> OTHER INFORMATION: light chain variable region

<400> SEQUENCE: 27

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Asn Ile Gly Thr Ser
            20                  25                  30

Ile Glu Trp Tyr Gln Gln Lys Pro Gly Gln Ala Pro Arg Leu Leu Ile
        35                  40                  45

Glu Phe Ala Ser Glu Ser Ile Ser Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Ser Asn Ser Trp Pro Phe
                85                  90                  95

Thr Phe Gly Gly Gly Thr Lys Val Glu Ile Lys
            100                 105

<210> SEQ ID NO 28
<211> LENGTH: 107
<212> TYPE: PRT
<213> ORGANISM: Artificial
<220> FEATURE:
<223> OTHER INFORMATION: light chain variable region

<400> SEQUENCE: 28

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Asn Ile Gly Thr Ser
            20                  25                  30
```

```
Ile Ser Trp Tyr Gln Gln Lys Pro Gly Gln Ala Pro Arg Leu Leu Ile
        35              40              45

Glu Phe Ala Ser Glu Ser Ile Ser Gly Ile Pro Ala Arg Phe Ser Gly
    50              55              60

Ser Gly Ser Gly Thr Asp Phe Thr Leu Thr Ile Ser Ser Leu Glu Pro
65              70              75              80

Glu Asp Phe Ala Val Tyr Tyr Cys Gln Gln Ser Asn Ser Trp Pro Phe
                85              90              95

Thr Phe Gly Gly Gly Thr Lys Val Glu Ile Lys
            100             105

<210> SEQ ID NO 29
<211> LENGTH: 107
<212> TYPE: PRT
<213> ORGANISM: Artificial
<220> FEATURE:
<223> OTHER INFORMATION: light chain variable region

<400> SEQUENCE: 29

Glu Ile Val Leu Thr Gln Ser Pro Ala Thr Leu Ser Leu Ser Pro Gly
1               5               10              15

Glu Arg Ala Thr Leu Ser Cys Arg Ala Ser Gln Asn Ile Gly Thr Ser
            20              25              30

Ile Ala Trp Tyr Gln Gln Lys Pro Gly Gln Ala Pro Arg Leu Leu Ile
        35              40              45

Glu Phe Ala Ser Glu Ser Ile Ser Gly Ile Pro Ala Arg Phe Ser Gly
    50              55              60

Ser Gly Ser Gly Thr Asp Phe Thr Leu Thr Ile Ser Ser Leu Glu Pro
65              70              75              80

Glu Asp Phe Ala Val Tyr Tyr Cys Gln Gln Ser Asn Ser Trp Pro Phe
                85              90              95

Thr Phe Gly Gly Gly Thr Lys Val Glu Ile Lys
            100             105

<210> SEQ ID NO 30
<211> LENGTH: 112
<212> TYPE: PRT
<213> ORGANISM: Artificial
<220> FEATURE:
<223> OTHER INFORMATION: light chain variable region

<400> SEQUENCE: 30

Asp Ile Val Met Thr Gln Ser Pro Leu Thr Leu Ser Val Thr Ile Gly
1               5               10              15

Gln Pro Ala Ser Ile Ser Cys Lys Ser Gly Gln Ser Leu Leu Asp Ser
            20              25              30

Asp Gly Lys Thr Tyr Phe Asn Trp Leu Leu Gln Arg Pro Gly Gln Ser
        35              40              45

Pro Lys Arg Leu Ile Tyr Leu Val Ser Met Leu Asp Ser Gly Val Pro
    50              55              60

Asp Arg Phe Thr Gly Ser Gly Ser Gly Thr Asp Phe Thr Leu Lys Ile
65              70              75              80

Ser Arg Val Glu Thr Glu Asp Leu Gly Val Tyr Tyr Cys Trp Gln Gly
                85              90              95

Thr His Phe Pro Phe Thr Phe Gly Ser Gly Thr Lys Leu Glu Ile Lys
            100             105             110

<210> SEQ ID NO 31
```

```
<211> LENGTH: 108
<212> TYPE: PRT
<213> ORGANISM: Artificial
<220> FEATURE:
<223> OTHER INFORMATION: light chain variable region

<400> SEQUENCE: 31

Asp Ile Gln Met Thr Gln Ile Thr Ser Ser Leu Ser Ala Ser Leu Gly
1               5                   10                  15

Asp Arg Val Thr Ile Thr Cys Arg Ala Ser Gln Asp Ile Ser Asn Tyr
            20                  25                  30

Leu Asn Trp Tyr Gln Gln Lys Pro Asp Gly Thr Val Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Tyr Thr Leu Pro Pro
                85                  90                  95

Tyr Thr Phe Gly Gly Gly Thr Lys Leu Glu Ile Lys
                100                 105

<210> SEQ ID NO 32
<211> LENGTH: 114
<212> TYPE: PRT
<213> ORGANISM: Artificial
<220> FEATURE:
<223> OTHER INFORMATION: light chain variable region

<400> SEQUENCE: 32

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Phe Cys Gln Gln Gly Tyr Thr Leu Pro Pro
                85                  90                  95

Tyr Thr Phe Gly Gln Gly Thr Lys Leu Glu Ile Lys Arg Thr Val Ala
                100                 105                 110

Ala Pro

<210> SEQ ID NO 33
<211> LENGTH: 108
<212> TYPE: PRT
<213> ORGANISM: Artificial
<220> FEATURE:
<223> OTHER INFORMATION: light chain variable region

<400> SEQUENCE: 33

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Asn Trp Tyr Gln Gln Lys Pro Gly Lys Ala Pro Lys Leu Leu Ile
```

-continued

```
        35              40              45
Tyr Tyr Thr Ser Arg Leu Glu Ser Gly Val Pro Ser Arg Phe Ser Gly
    50              55              60
Ser Gly Ser Gly Thr Asp Phe Thr Leu Thr Ile Ser Ser Leu Gln Pro
65              70              75              80
Glu Asp Phe Ala Thr Tyr Phe Cys Gln Gln Gly Tyr Thr Leu Pro Pro
                85              90              95
Tyr Thr Phe Gly Gln Gly Thr Lys Leu Glu Ile Lys
            100             105
```

<210> SEQ ID NO 34
<211> LENGTH: 114
<212> TYPE: PRT
<213> ORGANISM: Artificial
<220> FEATURE:
<223> OTHER INFORMATION: light chain variable region

<400> SEQUENCE: 34

```
Asp Ile Gln Met Thr Gln Ser Pro Ser Ser Leu Ser Ala Ser Val Gly
1               5               10              15
Asp Arg Val Thr Ile Thr Cys Arg Ala Ser Gln Asp Ile Ser Asn Tyr
            20              25              30
Leu Asn Trp Tyr Gln Gln Lys Pro Gly Lys Ala Pro Lys Leu Leu Ile
        35              40              45
Tyr Tyr Thr Ser Arg Leu Gln Ser Gly Val Pro Ser Arg Phe Ser Gly
    50              55              60
Ser Gly Ser Gly Thr Asp Phe Thr Leu Thr Ile Ser Ser Leu Gln Pro
65              70              75              80
Glu Asp Phe Ala Thr Tyr Phe Cys Gln Gln Gly Tyr Thr Leu Pro Pro
                85              90              95
Tyr Thr Phe Gly Gln Gly Thr Lys Leu Glu Ile Lys Arg Thr Val Ala
            100             105             110
Ala Pro
```

<210> SEQ ID NO 35
<211> LENGTH: 114
<212> TYPE: PRT
<213> ORGANISM: Artificial
<220> FEATURE:
<223> OTHER INFORMATION: light chain variable region

<400> SEQUENCE: 35

```
Asp Ile Gln Met Thr Gln Ser Pro Ser Ser Leu Ser Ala Ser Val Gly
1               5               10              15
Asp Arg Val Thr Ile Thr Cys Arg Ala Ser Gln Asp Ile Ser Asn Tyr
            20              25              30
Leu Asn Trp Tyr Gln Gln Lys Pro Gly Lys Ala Pro Lys Leu Leu Ile
        35              40              45
Tyr Tyr Thr Ser Arg Leu His Ser Gly Val Pro Ser Arg Phe Ser Gly
    50              55              60
Ser Gly Ser Gly Thr Asp Phe Thr Leu Thr Ile Ser Ser Leu Gln Pro
65              70              75              80
Glu Asp Phe Ala Thr Tyr Phe Cys Gln Gln Tyr Tyr Thr Leu Pro Pro
                85              90              95
Tyr Thr Phe Gly Gln Gly Thr Lys Leu Glu Ile Lys Arg Thr Val Ala
            100             105             110
Ala Pro
```

<210> SEQ ID NO 36
<211> LENGTH: 114
<212> TYPE: PRT
<213> ORGANISM: Artificial
<220> FEATURE:
<223> OTHER INFORMATION: light chain variable region

<400> SEQUENCE: 36

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Phe Cys Gln Gln Gly Tyr Ser Leu Pro Pro
                85                  90                  95

Tyr Thr Phe Gly Gln Gly Thr Lys Leu Glu Ile Lys Arg Thr Val Ala
            100                 105                 110

Ala Pro
```

<210> SEQ ID NO 37
<211> LENGTH: 330
<212> TYPE: PRT
<213> ORGANISM: Artificial
<220> FEATURE:
<223> OTHER INFORMATION: heavy chain constant region

<400> SEQUENCE: 37

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190
```

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
        210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
                275                 280                 285

Leu Tyr Ser Lys Leu Thr Val Asp Lys Ser Arg Trp Gln Gln Gly Asn
        290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 38
<211> LENGTH: 107
<212> TYPE: PRT
<213> ORGANISM: Artificial
<220> FEATURE:
<223> OTHER INFORMATION: light chain constant region

<400> SEQUENCE: 38

Arg Thr Val Ala Ala Pro Ser Val Phe Ile Phe Pro Pro Ser Asp Glu
1                   5                   10                  15

Gln Leu Lys Ser Gly Thr Ala Ser Val Val Cys Leu Leu Asn Asn Phe
                20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
        50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
                100                 105

<210> SEQ ID NO 39
<211> LENGTH: 451
<212> TYPE: PRT
<213> ORGANISM: Artificial
<220> FEATURE:
<223> OTHER INFORMATION: Sacituzumab, heavy chain

<400> SEQUENCE: 39

Gln Val Gln Leu Gln Gln Ser Gly Ser Glu Leu Lys Lys Pro Gly Ala
1                   5                   10                  15

Ser Val Lys Val Ser Cys Lys Ala Ser Gly Tyr Thr Phe Thr Asn Tyr
                20                  25                  30

Gly Met Asn Trp Val Lys Gln Ala Pro Gly Gln Gly Leu Lys Trp Met
        35                  40                  45

Gly Trp Ile Asn Thr Tyr Thr Gly Glu Pro Thr Tyr Thr Asp Asp Phe

-continued

```
            50                  55                  60

Lys Gly Arg Phe Ala Phe Ser Leu Asp Thr Ser Val Ser Thr Ala Tyr
65                  70                  75                  80

Leu Gln Ile Ser Ser Leu Lys Ala Asp Asp Thr Ala Val Tyr Phe Cys
                85                  90                  95

Ala Arg Gly Gly Phe Gly Ser Ser Tyr Trp Tyr Phe Asp Val Trp Gly
                100                 105                 110

Gln Gly Ser Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
        130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
                180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Arg Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450
```

<210> SEQ ID NO 40

<211> LENGTH: 214
<212> TYPE: PRT
<213> ORGANISM: Artificial
<220> FEATURE:
<223> OTHER INFORMATION: Sacituzumab, light chain

<400> SEQUENCE: 40

```
Asp Ile Gln Leu Thr Gln Ser Pro Ser Ser Leu Ser Ala Ser Val Gly
1               5                   10                  15

Asp Arg Val Ser Ile Thr Cys Lys Ala Ser Gln Asp Val Ser Ile Ala
            20                  25                  30

Val Ala Trp Tyr Gln Gln Lys Pro Gly Lys Ala Pro Lys Leu Leu Ile
        35                  40                  45

Tyr Ser Ala Ser Tyr Arg Tyr Thr Gly Val Pro Asp Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Val Tyr Tyr Cys Gln Gln His Tyr Ile Thr Pro Leu
                85                  90                  95

Thr Phe Gly Ala Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
    210
```

<210> SEQ ID NO 41
<211> LENGTH: 369
<212> TYPE: DNA
<213> ORGANISM: Artificial
<220> FEATURE:
<223> OTHER INFORMATION: heavy chain variable region

<400> SEQUENCE: 41

```
caggtccaac tgcagcagcc tgggctgaa ctggtgaagc ctgggtcttc agtgaagctg      60
tcctgcaagg cttctggcta caccttcact agttactgga tgtactgggt gaagcagagg     120
cctggacagg gccttgagtg gattggagag attaatccta gtaacggtcg tactaattac     180
aatgagaagt tcaagagcaa ggccacactg actgtagaca atcgtccag cacagcctac      240 atgcaattca gcagcctgac atctgaggac tctgcggtct attactgtac aagagaaggc     300
cataattacg atggttccct cggggctatg gaccactggg gtcaaggaac ctcagtcacc     360
gtctcctca                                                            369
```

<210> SEQ ID NO 42
<211> LENGTH: 336
<212> TYPE: DNA
<213> ORGANISM: Artificial

```
<220> FEATURE:
<223> OTHER INFORMATION: light chain variable region

<400> SEQUENCE: 42
gatgttgtgg tgactcaaac tccactctcc ctgcctgtca gctttggaga tcaggtttct      60
atctcttgca ggtctagtca gagtcttaca aacagttatg ggaacacctt tttgtcttgg     120
tacctgcaca agcctggcca gtctccacag ctcctcctct atgggatttc caacagattt     180 tctgggggtgc cagacaggtt cagtggcagt ggttcaggga cagatttcac actcaagatc     240
aacacaataa agcctgagga cctgggaatg tattactgct ttcaaagtac acatcagccg     300
tacacgttcg gagggggggac caagctggaa ataaaa                               336

<210> SEQ ID NO 43
<211> LENGTH: 351
<212> TYPE: DNA
<213> ORGANISM: Artificial
<220> FEATURE:
<223> OTHER INFORMATION: heavy chain variable region

<400> SEQUENCE: 43
caggttcagc tgcagcagtc tggacctgag ctggtgaagc ctgggggcttc agtgaagatg      60 tcctgcaagg cttctggatt cacattcact gactatgtta taggctgggt gaagcagaga     120
actggacagg gccttgagtg gattggagag atttatcttg gaagtggtac tatttactac     180
actgagaagt tcaagggcaa ggccacactg actgcagaca tcctccaa cacagcctac       240 atgcagctca gcagcctgac gtctgaagac tctgcggtct atttctgtgc aaggggatct     300
attttcccct ttgactactg gggccaaggc accactctca cagtctcctc a               351

<210> SEQ ID NO 44
<211> LENGTH: 318
<212> TYPE: DNA
<213> ORGANISM: Artificial
<220> FEATURE:
<223> OTHER INFORMATION: light chain variable region

<400> SEQUENCE: 44
caaattgttc tcacccagtc tccagcaatc atgtctgcat ctccagggga gaaggtcacc      60
atgacctgca gtgccagctc aagtgtaagt tacatgtact ggtaccagca gaagccagga     120
tcctccccca gactcctgat ttatgacaca tccaccctgg cttctggagt ccctgttcgc     180
ttcagtggca gtgggtctgg gacctcttac tctctcacaa tcagccgaat ggaggctgaa     240
gatgctgcca cttactactg ccagcagtgg agtagttacc cttacacgtt cggaggggggg     300 accaagctgg aaataaaa                                                    318

<210> SEQ ID NO 45
<211> LENGTH: 351
<212> TYPE: DNA
<213> ORGANISM: Artificial
<220> FEATURE:
<223> OTHER INFORMATION: heavy chain variable region

<400> SEQUENCE: 45
gaggtgcagc tggtgcagtc tggacccgag gtgaagaagc ctggagcctc cgtgaaggtg      60
tcctgcaagg cctccggctt caccttcacc gactacgtga tcggctgggt gcgacaggct     120
cctggccagg gactggagtg gatcggcgag atctacctgg ctccggcac catctactac       180 accgagaagt tcaagggacg ggtgaccatg acagccgaca cctccacctc caccgcctac     240
```
atggagctgt cctccctgcg gtccgaggac accgccgtgt actactgcgc tcgaggctcc          300
atcttcccct tcgactactg gggccagggc accctggtga ccgtgtcctc t                  351

```
<210> SEQ ID NO 46
<211> LENGTH: 318
<212> TYPE: DNA
<213> ORGANISM: Artificial
<220> FEATURE:
<223> OTHER INFORMATION: light chain variable region

<400> SEQUENCE: 46
```
gacatccagc tgacccagtc tccctcctcc ctgtctgcct ccgtgggcga cagggtgacc           60
atcacctgct ctgcctcctc ctccgtgtcc tacatgtact ggtaccagca gaagcctggc          120
aaggctccca agctgctgat ctacgacacc tccaccctgg cctctggcgt gccctccagg          180
ttctctggct ccggatctgg caccgacttc accctgacca tctcctccct gcagcccgag          240
gacttcgcca cctactactg ccagcagtgg tcctcctacc cctacacctt cggacagggc          300
accaagctgg agatcaag                                                         318

```
<210> SEQ ID NO 47
<211> LENGTH: 351
<212> TYPE: DNA
<213> ORGANISM: Artificial
<220> FEATURE:
<223> OTHER INFORMATION: heavy chain variable region

<400> SEQUENCE: 47
```
caggtccaac tgcagcagcc tggggctgag ctggtgaggc ctggggcttc agtgaacctg           60
tcctgcaagg cttctggcta caccttcacc agctactgga taaactgggt gaagcagagg          120
cctggacaag gccttgagtg gatcggaaat atttatcctt ctaatagtta tactaactac          180
aatcaaaagt tcaaggacac ggccacattg actgtagaca atcctccag cacagcctac           240 atgcagctca gcagcccgac atctgaggac tctgcggtct atttctgttc aagttatagg          300
tccgacgggt ttgcttactg gggccaaggg actcttgtca ctgtctctgc a                  351

```
<210> SEQ ID NO 48
<211> LENGTH: 321
<212> TYPE: DNA
<213> ORGANISM: Artificial
<220> FEATURE:
<223> OTHER INFORMATION: light chain variable region

<400> SEQUENCE: 48
```
gacatcttgc tgactcagtc tccagccatc ctgtctgtga gtccaggaga aaaagtcagt           60
ttctcctgca gggccagtca gaacattggc acaagcatac actggtatca gcaaagaaca          120
aatggttctc caaggcttct catagaattt gcttctgagt ctatctctgg gatcccttcc          180
aggtttagtg gcagtggatc agggacagat tttactctta ccatcaacag tgtggagtct          240
gaagatattg cagattatta ctgtcaacaa agtaatagct ggccgttcac gttcggaggg          300
gggaccaagc tggaaataaa a                                                    321

```
<210> SEQ ID NO 49
<211> LENGTH: 351
<212> TYPE: DNA
<213> ORGANISM: Artificial
<220> FEATURE:
<223> OTHER INFORMATION: heavy chain variable region

<400> SEQUENCE: 49
```

-continued

```
caggtgcagc tggtgcagtc tggagccgag gtgaagaagc ctggagcctc cgtgaaggtg        60
tcctgcaagg cctccggcta caccttcacc tcctactgga tcaactgggt gcggcaggct       120
cctggccagg gactggagtg gatgggcaac atctacccat ccaactccta caccaactac       180
aaccagaagt tcaaggacag ggtgaccatg accagagaca cctccacctc caccgtgtac       240
atggagctgt cctccctgcg gtccgaggac acagccgtgt actactgcgc tcggtaccgg       300
tctgacggct cgcctactg gggacagggc accctggtga ccgtgtcctc c                351
```

```
<210> SEQ ID NO 50
<211> LENGTH: 321
<212> TYPE: DNA
<213> ORGANISM: Artificial
<220> FEATURE:
<223> OTHER INFORMATION: light chain variable region

<400> SEQUENCE: 50
```

```
gagatcgtgc tgacccagtc tcctgccacc ctgtccctgt ctcctggcga gagagccacc        60
ctgtcctgca gagcctccca gaacatcggc acctccatcc actggtacca gcagaagcct       120
ggccaggctc ctcggctgct gatctacttc gcctccgagt ccatctctgg catccctgct       180
cggttctctg gctccggatc tggcaccgac ttcaccctga ccatctcctc cctggagcct       240
gaggacttcg ccgtgtacta ctgccagcag tccaactcct ggcccttcac cttcggaggt       300
ggcaccaagg tggagatcaa g                                                 321
```

```
<210> SEQ ID NO 51
<211> LENGTH: 345
<212> TYPE: DNA
<213> ORGANISM: Artificial
<220> FEATURE:
<223> OTHER INFORMATION: heavy chain variable region

<400> SEQUENCE: 51
```

```
gaggtgaagc tggtggagtc tgggggagtc ttagtgaagc ctggagggtc cctgaaactc        60
tcctgtgcag cctctggatt cactttcagt gactctgcca tgtcttgggt tcgccagact       120
ccagagaaga ggctggagtg ggtcgcatcc attagtcgtg gtgatgacac atattatcca       180
gacagtgtga agggccgaat caccatttcc agagattttg ccagaaacat cctgtatttg       240
caaatgacca gtctgaggtc tgaggacacg gccatgtatt actgtacaag agatcggttc       300
gggtttgctt actggggcca agggactctg gtcactgtct ctgca                       345
```

```
<210> SEQ ID NO 52
<211> LENGTH: 336
<212> TYPE: DNA
<213> ORGANISM: Artificial
<220> FEATURE:
<223> OTHER INFORMATION: light chain variable region

<400> SEQUENCE: 52
```

```
gacattgtga tgacccagtc tccactcact ttgtcggtta ccattggaca acctgcctcc        60
atctcttgca gtcaggtca gagcctctta gatagtgatg gaaagacata ttttaattgg       120
ttgttacaga ggccaggcca gtctccaaag cgcctaatct atctggtgtc tatgctggac       180
tctggagtcc ctgacaggtt cactggcagt ggatcaggga cagatttcac actgaaaatc       240
agcagagtgg agactgagga tttgggagtt tattattgct ggcaaggtac acattttcca       300
ttcacgttcg gctcggggac aaagttggaa ataaag                                 336
```

<210> SEQ ID NO 53
<211> LENGTH: 357
<212> TYPE: DNA
<213> ORGANISM: Artificial
<220> FEATURE:
<223> OTHER INFORMATION: heavy chain variable region

<400> SEQUENCE: 53
caggtccaac tgcagcagcc tgggggctgag cttgtgaagc ctgggggcttc agtgaagctg      60 tcctgtaagg ctgatggcta catcttcacc agttactgga tgcactgggt gaaacagagg     120
cctggacaag gccttgagtg gatcggagag attactcctt ctgataatta tacttcctac     180
aatcaaaagt tcaagggcaa ggccacattg actgtagaca atcctccag cacagcctac      240 atgcagctca gcagcctgac gtctgaggac tctgcggtct attactgtac aagaggccac     300
ggtaactacg tcagctttga ctactggggc caaggcacca ctctcacagt ctcctca        357

<210> SEQ ID NO 54
<211> LENGTH: 324
<212> TYPE: DNA
<213> ORGANISM: Artificial
<220> FEATURE:
<223> OTHER INFORMATION: light chain variable region

<400> SEQUENCE: 54
gacatccaga tgacacagat tacatcctcc ctgtctgcct ctctgggaga cagagtcacc      60
atcacttgca gggcaagtca ggacattagc aattatttaa actggtatca gcagaaacca     120
gatggaactg ttaaactcct gatctactac acatcaagat tacactcagg agtcccctca     180
aggttcagtg gcagtgggtc tggaacagat tattctctca ccattagcaa cctggagcaa     240
gaagatattg ccacttactt ttgccaacag ggttatacgc ttcctccgta cacgttcgga     300
gggggaccca agctggaaat aaaa                                              324

<210> SEQ ID NO 55
<211> LENGTH: 357
<212> TYPE: DNA
<213> ORGANISM: Artificial
<220> FEATURE:
<223> OTHER INFORMATION: heavy chain variable region

<400> SEQUENCE: 55
caggtgcagc tggtgcagtc cggagccgag gtgaagaagc ctggagcctc cgtgaaggtg      60
tcctgcaagg cctccggcta caccttcacc tcctactgga tgcactgggt gcggcaggct     120
cctggccagg gactggagtg gatgggcgag atcacaccct ccgacaacta cacctcctac     180
aaccagaagt tcaagggacg ggtgaccatc accaggggaca cctccaccctc caccgcctac    240 atggagctgt cctccctgcg gtccgaggac accgccgtgt actactgcgc tcgaggccac     300
ggcaactacg tgtccttcga ctactgggga caggcacccc tggtgaccgt gtcctcc         357

<210> SEQ ID NO 56
<211> LENGTH: 324
<212> TYPE: DNA
<213> ORGANISM: Artificial
<220> FEATURE:
<223> OTHER INFORMATION: light chain variable region

<400> SEQUENCE: 56
gacatccaga tgacccagtc tccctcctcc ctgtctgcct ccgtgggaga ccgggtgacc      60
atcacctgca gagcctccca ggacatctcc aactacctga actggtacca gcagaagcct     120

-continued

```
ggcaaggctc ccaagctgct gatctactac acctccaggc tgcactccgg agtgccctcc      180
cggttctccg gctctggctc cggaaccgac ttcaccctga ccatctcctc cctgcagccc      240
gaggacttcg ccacctactt ctgccagcag ggctacaccc tgcctcccta caccttcggc      300
cagggcacca agctggagat caag                                           324

<210> SEQ ID NO 57
<211> LENGTH: 357
<212> TYPE: DNA
<213> ORGANISM: Artificial
<220> FEATURE:
<223> OTHER INFORMATION: heavy chain variable region

<400> SEQUENCE: 57
caggtgcagc tggtgcagtc cggagccgag gtgaagaagc ctggagcctc cgtgaaggtg       60
tcctgcaagg cctccggcta caccttcacc tcctactgga tgcactgggt gcggcaggct      120
cctggccagg gactggagtg gatgggcgag atcacaccct ccgacaacta cggctcctac      180
aaccagaagt tcaagggacg ggtgaccatc accagggaca cctccacctc caccgcctac      240
atggagctgt cctccctgcg gtccgaggac accgccgtgt actactgcgc tcgaggccac      300
ggcaactacg tgtccttcga ctactgggga cagggcaccc tggtgaccgt gtcctcc        357

<210> SEQ ID NO 58
<211> LENGTH: 324
<212> TYPE: DNA
<213> ORGANISM: Artificial
<220> FEATURE:
<223> OTHER INFORMATION: light chain variable region

<400> SEQUENCE: 58
gacatccaga tgacccagtc tccctcctcc ctgtctgcct ccgtgggaga ccgggtgacc       60
atcacctgca gagcctccca ggacatctcc aactacctga actggtacca gcagaagcct      120
ggcaaggctc ccaagctgct gatctactac acctccaggc tggagtccgg agtgccctcc      180
cggttctccg gctctggctc cggaaccgac ttcaccctga ccatctcctc cctgcagccc      240
gaggacttcg ccacctactt ctgccagcag ggctacaccc tgcctcccta caccttcggc      300
cagggcacca agctggagat caag                                           324

<210> SEQ ID NO 59
<211> LENGTH: 990
<212> TYPE: DNA
<213> ORGANISM: Artificial
<220> FEATURE:
<223> OTHER INFORMATION: heavy chain constant region

<400> SEQUENCE: 59
gctagcacca agggcccatc ggtcttcccc ctggcaccct cctccaagag cacctctggg       60
ggcacagcgg ccctgggctg cctggtcaag gactacttcc ccgaaccggt gacggtgtcg      120
tggaactcag gcgccctgac cagcggcgtg cacaccttcc cggctgtcct acagtcctca      180
ggactctact ccctcagcag cgtggtgacc gtgccctcca gcagcttggg cacccagacc      240
tacatctgca acgtgaatca caagcccagc aacaccaagg tggacaagag agttgagccc      300
aaatcttgtg acaaaactca cacatgccca ccgtgcccag cacctgaact cctggggggga      360
```

-continued

```
ccgtcagtct tcctcttccc cccaaaaccc aaggacaccc tcatgatctc ccggacccct     420
gaggtcacat gcgtggtggt ggacgtgagc cacgaagacc ctgaggtcaa gttcaactgg     480
tacgtggacg gcgtggaggt gcataatgcc aagacaaagc cgcgggagga gcagtacaac     540
agcacgtacc gtgtggtcag cgtcctcacc gtcctgcacc aggactggct gaatggcaag     600
gagtacaagt gcaaggtctc caacaaagcc ctcccagccc ccatcgagaa aaccatctcc     660
aaagccaaag ggcagccccg agaaccacag gtgtacaccc tgcccccatc ccgggaggag     720
atgaccaaga accaggtcag cctgacctgc ctggtcaaag gcttctatcc cagcgacatc     780
gccgtggagt gggagagcaa tgggcagccg gagaacaact acaagaccac gcctcccgtg     840
ctggactccg acggctcctt cttcctctat agcaagctca ccgtggacaa gagcaggtgg     900
cagcagggga acgtcttctc atgctccgtg atgcatgagg ctctgcacaa ccactacacg     960
cagaagagcc tctccctgtc cccgggtaaa                                        990

<210> SEQ ID NO 60
<211> LENGTH: 321
<212> TYPE: DNA
<213> ORGANISM: Artificial
<220> FEATURE:
<223> OTHER INFORMATION: light chain constant region

<400> SEQUENCE: 60
agaaccgtgg cggcgccatc tgtcttcatc ttcccgccat ctgatgagca gttgaaatct      60
ggtaccgcta gcgttgtgtg cctgctgaat aacttctatc ccagagaggc caaagtacag     120
tggaaggtgg ataacgccct ccaatcgggt aactcccagg agagtgtcac agagcaggac     180
agcaaggaca gcacctacag cctcagcagc accctgacgc tgagcaaagc agactacgag     240
aaacacaaag tctacgcctg cgaagtcacc catcagggcc tgagctcgcc cgtcacaaag     300
agcttcaaca ggggagagtg t                                                 321
```